(12) United States Patent　　(10) Patent No.: US 8,628,547 B2
Weller et al.　　(45) Date of Patent: Jan. 14, 2014

(54) DEVICES AND METHODS FOR PLACEMENT OF PARTITIONS WITHIN A HOLLOW BODY ORGAN

(75) Inventors: Gary Weller, Los Gatos, CA (US); Alex T. Roth, Redwood City, CA (US); Christopher Julian, Los Gatos, CA (US); Jamy Gannoe, Redwood City, CA (US); Andrew H. Hancock, Fremont, CA (US); Craig Gerbi, Mountain View, CA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1587 days.

(21) Appl. No.: 10/797,303

(22) Filed: Mar. 9, 2004

(65) Prior Publication Data

US 2005/0203547 A1　　Sep. 15, 2005

(51) Int. Cl.
　　*A61B 17/08*　　(2006.01)
(52) U.S. Cl.
　　USPC ................... 606/151; 606/153; 227/175.1
(58) Field of Classification Search
　　USPC .................. 606/151, 153; 227/175.1
　　See application file for complete search history.

(56) References Cited

U.S. PATENT DOCUMENTS

| | | |
|---|---|---|
| 2,108,206 A | 2/1938 | Meeker |
| 2,508,690 A | 7/1948 | Schmerl |
| 3,372,443 A | 3/1968 | Daddona, Jr. |
| 3,395,710 A | 8/1968 | Stratton et al. |
| 3,986,493 A | 10/1976 | Hendren, III |
| 4,057,065 A | 11/1977 | Thow |
| 4,063,561 A | 12/1977 | McKenna |
| 4,133,315 A | 1/1979 | Berman et al. |
| 4,134,405 A | 1/1979 | Smit |
| 4,198,982 A | 4/1980 | Fortner et al. |
| 4,246,893 A | 1/1981 | Berson |
| 4,258,705 A | 3/1981 | Sorensen et al. |
| 4,311,146 A | 1/1982 | Wonder |

(Continued)

FOREIGN PATENT DOCUMENTS

| | | |
|---|---|---|
| AU | 2006230695 | 10/2006 |
| EP | 0 137 878 A1 | 4/1985 |

(Continued)

OTHER PUBLICATIONS

U.S. Appl. No. 10/417,790, filed Apr. 16, 2003, Gannoe et al.

(Continued)

*Primary Examiner* — Gary Jackson
*Assistant Examiner* — Diane Yabut
(74) *Attorney, Agent, or Firm* — Nutter McClennan & Fish LLP

(57) ABSTRACT

Devices and methods for tissue acquisition and fixation, or gastroplasty, are described. Generally, the devices of the system may be advanced in a minimally invasive manner within a patient's body, e.g., transorally, endoscopically, percutaneously, etc., to create one or several divisions or plications within the hollow body organ. Such divisions or plications can form restrictive barriers within a organ, or can be placed to form a pouch, or gastric lumen, smaller than the remaining stomach volume to essentially act as the active stomach such as the pouch resulting from a surgical Roux-En-Y gastric bypass procedure. Moreover, the system is configured such that once acquisition of the tissue by the gastroplasty device is accomplished, any manipulation of the acquired tissue is unnecessary as the device is able to automatically configure the acquired tissue into a desired configuration.

9 Claims, 52 Drawing Sheets

(56) References Cited

U.S. PATENT DOCUMENTS

| | | |
|---|---|---|
| 4,315,509 A | 2/1982 | Smit |
| 4,343,066 A | 8/1982 | Lance |
| 4,402,445 A | 9/1983 | Green |
| 4,416,267 A | 11/1983 | Garren et al. |
| 4,458,681 A | 7/1984 | Hopkins |
| 4,485,805 A | 12/1984 | Foster, Jr. |
| 4,501,264 A | 2/1985 | Rockey |
| 4,547,192 A | 10/1985 | Brodsky et al. |
| 4,558,699 A | 12/1985 | Bashour |
| 4,592,339 A | 6/1986 | Kuzmak et al. |
| 4,592,354 A | 6/1986 | Rothfuss |
| 4,598,699 A | 7/1986 | Garren et al. |
| 4,607,618 A | 8/1986 | Angelchik |
| 4,610,383 A | 9/1986 | Rothfuss et al. |
| 4,636,205 A | 1/1987 | Steer |
| 4,641,653 A | 2/1987 | Rockey |
| 4,643,169 A | 2/1987 | Koss et al. |
| 4,646,722 A | 3/1987 | Silverstein et al. |
| 4,648,383 A | 3/1987 | Angelchik |
| 4,671,287 A | 6/1987 | Fiddian-Green |
| 4,694,827 A | 9/1987 | Weiner et al. |
| 4,696,288 A | 9/1987 | Kuzmak et al. |
| 4,716,900 A | 1/1988 | Ravo et al. |
| 4,723,547 A | 2/1988 | Kullas et al. |
| 4,739,758 A | 4/1988 | Lai et al. |
| 4,744,363 A | 5/1988 | Hasson |
| 4,773,393 A | 9/1988 | Haber et al. |
| 4,790,294 A | 12/1988 | Allred, III et al. |
| 4,795,430 A | 1/1989 | Quinn et al. |
| 4,803,985 A | 2/1989 | Hill |
| 4,841,888 A | 6/1989 | Mills et al. |
| 4,892,244 A | 1/1990 | Fox |
| 4,899,747 A | 2/1990 | Garren et al. |
| 4,905,693 A | 3/1990 | Ravo |
| 4,925,446 A | 5/1990 | Garay et al. |
| 4,927,428 A | 5/1990 | Richards |
| 4,969,474 A | 11/1990 | Schwarz |
| 5,037,021 A | 8/1991 | Mills et al. |
| 5,059,193 A | 10/1991 | Kuslich |
| 5,080,663 A | 1/1992 | Mills et al. |
| 5,084,061 A | 1/1992 | Gau et al. |
| 5,112,310 A | 5/1992 | Grobe |
| 5,129,915 A | 7/1992 | Cantenys |
| 5,146,933 A | 9/1992 | Boyd |
| 5,156,609 A | 10/1992 | Nakao et al. |
| 5,171,233 A | 12/1992 | Amplatz et al. |
| 5,197,649 A | 3/1993 | Bessler et al. |
| 5,220,928 A | 6/1993 | Oddsen et al. |
| 5,222,961 A | 6/1993 | Nakao et al. |
| 5,226,429 A | 7/1993 | Kuzmak |
| 5,234,454 A | 8/1993 | Bangs |
| 5,246,456 A | 9/1993 | Wilkinson |
| 5,248,302 A | 9/1993 | Patrick et al. |
| 5,250,058 A | 10/1993 | Miller et al. |
| 5,250,075 A | 10/1993 | Badie |
| 5,254,126 A | 10/1993 | Filipi et al. |
| 5,259,366 A | 11/1993 | Reydel et al. |
| 5,259,399 A | 11/1993 | Brown |
| 5,261,920 A | 11/1993 | Main et al. |
| 5,263,629 A | 11/1993 | Trumbull et al. |
| 5,284,128 A | 2/1994 | Hart |
| 5,297,536 A | 3/1994 | Wilk |
| 5,301,658 A | 4/1994 | Zhu et al. |
| 5,306,300 A | 4/1994 | Berry |
| 5,309,896 A | 5/1994 | Moll et al. |
| 5,309,927 A | 5/1994 | Welch |
| 5,327,914 A | 7/1994 | Shlain |
| 5,330,486 A | 7/1994 | Wilk |
| 5,330,503 A | 7/1994 | Yoon |
| 5,331,975 A | 7/1994 | Bonutti |
| 5,334,209 A | 8/1994 | Yoon |
| 5,334,210 A | 8/1994 | Gianturco |
| 5,345,949 A | 9/1994 | Shlain |
| 5,346,501 A | 9/1994 | Regula et al. |
| 5,355,897 A | 10/1994 | Pietrafitta et al. |
| 5,358,496 A | 10/1994 | Ortiz |
| 5,376,095 A | 12/1994 | Ortiz |
| 5,382,231 A | 1/1995 | Shlain |
| 5,403,312 A | 4/1995 | Yates et al. |
| 5,403,326 A | 4/1995 | Harrison et al. |
| 5,411,508 A | 5/1995 | Bessler et al. |
| 5,433,721 A | 7/1995 | Hooven et al. |
| 5,437,291 A | 8/1995 | Pasricha et al. |
| 5,449,368 A | 9/1995 | Kuzmak |
| 5,452,837 A | 9/1995 | Williamson, IV et al. |
| 5,458,131 A | 10/1995 | Wilk |
| 5,462,559 A | 10/1995 | Ahmed |
| 5,465,894 A | 11/1995 | Clark et al. |
| 5,467,911 A | 11/1995 | Tsuruta et al. |
| 5,486,183 A | 1/1996 | Middleman et al. |
| 5,489,058 A | 2/1996 | Plyley et al. |
| 5,503,635 A | 4/1996 | Sauer et al. |
| 5,527,319 A | 6/1996 | Green et al. |
| 5,535,935 A | 7/1996 | Vidal et al. |
| 5,542,949 A | 8/1996 | Yoon |
| 5,549,621 A | 8/1996 | Bessler et al. |
| 5,551,622 A | 9/1996 | Yoon |
| 5,555,898 A | 9/1996 | Suzuki et al. |
| 5,558,665 A | 9/1996 | Kieturakis |
| 5,571,116 A | 11/1996 | Bolanos et al. |
| 5,577,654 A | 11/1996 | Bishop |
| 5,578,044 A | 11/1996 | Gordon et al. |
| 5,582,616 A | 12/1996 | Bolduc et al. |
| 5,584,861 A | 12/1996 | Swain et al. |
| 5,588,579 A | 12/1996 | Schnut et al. |
| 5,601,604 A | 2/1997 | Vincent |
| 5,603,443 A | 2/1997 | Clark et al. |
| 5,607,094 A | 3/1997 | Clark et al. |
| 5,624,381 A | 4/1997 | Kieturakis |
| 5,626,588 A | 5/1997 | Sauer et al. |
| 5,639,008 A | 6/1997 | Gallagher et al. |
| 5,649,937 A | 7/1997 | Bito et al. |
| 5,651,769 A | 7/1997 | Waxman et al. |
| 5,655,698 A | 8/1997 | Yoon |
| 5,662,664 A | 9/1997 | Gordon et al. |
| 5,662,667 A | 9/1997 | Knodel |
| 5,667,520 A | 9/1997 | Bonutti |
| 5,676,659 A | 10/1997 | McGurk |
| 5,676,674 A | 10/1997 | Bolanos |
| 5,681,263 A | 10/1997 | Flesch |
| 5,685,868 A | 11/1997 | Lundquist |
| 5,690,656 A | 11/1997 | Cope et al. |
| 5,697,943 A | 12/1997 | Sauer et al. |
| 5,707,382 A | 1/1998 | Sierocuk et al. |
| 5,722,990 A | 3/1998 | Sugarbaker et al. |
| 5,728,178 A | 3/1998 | Buffington et al. |
| 5,735,848 A | 4/1998 | Yates et al. |
| 5,749,893 A | 5/1998 | Vidal et al. |
| 5,755,730 A | 5/1998 | Swain et al. |
| 5,766,216 A | 6/1998 | Gangal et al. |
| 5,776,054 A | 7/1998 | Bobra |
| 5,782,397 A | 7/1998 | Koukline |
| 5,782,844 A | 7/1998 | Yoon et al. |
| 5,788,715 A | 8/1998 | Watson, Jr. et al. |
| 5,792,153 A | 8/1998 | Swain et al. |
| 5,797,931 A | 8/1998 | Bito et al. |
| 5,810,851 A | 9/1998 | Yoon |
| 5,810,855 A | 9/1998 | Rayburn et al. |
| 5,810,882 A | 9/1998 | Bolduc et al. |
| 5,816,471 A | 10/1998 | Plyley et al. |
| 5,820,584 A | 10/1998 | Crabb |
| 5,824,008 A | 10/1998 | Bolduc et al. |
| 5,827,298 A | 10/1998 | Hart et al. |
| 5,833,690 A | 11/1998 | Yates et al. |
| 5,836,311 A | 11/1998 | Borst et al. |
| 5,839,639 A | 11/1998 | Sauer et al. |
| 5,860,581 A | 1/1999 | Robertson et al. |
| 5,861,036 A | 1/1999 | Godin |
| 5,868,141 A | 2/1999 | Ellias |
| 5,868,760 A | 2/1999 | McGuckin, Jr. |
| 5,876,448 A | 3/1999 | Thompson et al. |
| 5,879,371 A | 3/1999 | Gardiner et al. |
| 5,887,594 A | 3/1999 | LoCicero, III |
| 5,888,196 A | 3/1999 | Bonutti |

(56) References Cited

U.S. PATENT DOCUMENTS

| | | |
|---|---|---|
| 5,897,534 A | 4/1999 | Heim et al. |
| 5,897,562 A | 4/1999 | Bolanos et al. |
| 5,904,147 A | 5/1999 | Conlan et al. |
| 5,906,625 A | 5/1999 | Bito et al. |
| 5,910,105 A | 6/1999 | Swain et al. |
| 5,910,149 A | 6/1999 | Kuzmak |
| 5,921,993 A | 7/1999 | Yoon |
| 5,927,284 A | 7/1999 | Borst et al. |
| 5,928,264 A | 7/1999 | Sugarbaker et al. |
| 5,935,107 A | 8/1999 | Taylor et al. |
| 5,938,669 A | 8/1999 | Klaiber et al. |
| 5,947,983 A | 9/1999 | Solar et al. |
| 5,964,772 A | 10/1999 | Bolduc et al. |
| 5,964,782 A | 10/1999 | Lafontaine et al. |
| 5,972,001 A | 10/1999 | Yoon |
| 5,972,002 A | 10/1999 | Bark et al. |
| 5,976,161 A | 11/1999 | Kirsch et al. |
| 5,980,537 A | 11/1999 | Ouchi |
| 5,993,464 A | 11/1999 | Knodel |
| 5,993,473 A | 11/1999 | Chan et al. |
| 6,015,378 A | 1/2000 | Borst et al. |
| 6,030,364 A | 2/2000 | Durgin et al. |
| 6,030,392 A | 2/2000 | Dakov |
| 6,042,538 A | 3/2000 | Puskas |
| 6,044,847 A | 4/2000 | Carter et al. |
| 6,067,991 A | 5/2000 | Forsell |
| 6,074,343 A | 6/2000 | Nathanson et al. |
| 6,083,241 A | 7/2000 | Longo et al. |
| 6,086,600 A | 7/2000 | Kortenbach |
| 6,113,609 A | 9/2000 | Adams |
| 6,119,913 A | 9/2000 | Adams et al. |
| 6,120,513 A | 9/2000 | Bailey et al. |
| 6,136,006 A | 10/2000 | Johnson et al. |
| 6,159,146 A | 12/2000 | El Gazayerli |
| 6,159,195 A | 12/2000 | Ha et al. |
| 6,165,183 A | 12/2000 | Kuehn et al. |
| 6,179,195 B1 | 1/2001 | Adams et al. |
| 6,186,942 B1 | 2/2001 | Sullivan et al. |
| 6,186,985 B1 | 2/2001 | Snow |
| 6,197,022 B1 | 3/2001 | Baker |
| 6,200,318 B1 | 3/2001 | Har-Shai et al. |
| 6,206,822 B1 | 3/2001 | Foley et al. |
| 6,206,893 B1 | 3/2001 | Klein et al. |
| 6,224,614 B1 | 5/2001 | Yoon |
| 6,231,561 B1 | 5/2001 | Frazier et al. |
| 6,248,058 B1 | 6/2001 | Silverman et al. |
| 6,254,642 B1 | 7/2001 | Taylor |
| 6,273,897 B1 | 8/2001 | Dalessandro et al. |
| 6,279,809 B1 | 8/2001 | Nicolo |
| 6,290,674 B1 | 9/2001 | Roue et al. |
| 6,293,923 B1 | 9/2001 | Yachia et al. |
| 6,302,917 B1 | 10/2001 | Dua et al. |
| 6,312,437 B1 | 11/2001 | Kortenbach |
| 6,328,689 B1 | 12/2001 | Gonzalez et al. |
| 6,338,345 B1 | 1/2002 | Johnson |
| 6,352,543 B1 | 3/2002 | Cole |
| 6,358,197 B1 | 3/2002 | Silverman et al. |
| 6,379,366 B1 | 4/2002 | Fleischman et al. |
| 6,387,104 B1 | 5/2002 | Pugsley, Jr. et al. |
| 6,398,795 B1 | 6/2002 | McAlister et al. |
| 6,416,535 B1 | 7/2002 | Lazarus |
| 6,423,087 B1 | 7/2002 | Sawada |
| 6,432,040 B1 | 8/2002 | Meah |
| 6,447,533 B1 | 9/2002 | Adams |
| 6,460,543 B1 | 10/2002 | Forsell |
| 6,475,136 B1 | 11/2002 | Forsell |
| 6,478,791 B1 | 11/2002 | Carter et al. |
| 6,491,707 B2 | 12/2002 | Makower et al. |
| 6,494,888 B1 | 12/2002 | Laufer et al. |
| 6,506,196 B1 | 1/2003 | Laufer |
| 6,535,764 B2 | 3/2003 | Imran et al. |
| 6,540,789 B1 | 4/2003 | Silverman et al. |
| 6,551,310 B1 | 4/2003 | Ganz et al. |
| 6,554,844 B2 | 4/2003 | Lee et al. |
| 6,558,400 B2 * | 5/2003 | Deem et al. .................. 606/151 |
| 6,561,969 B2 | 5/2003 | Frazier et al. |
| 6,572,629 B2 | 6/2003 | Kalloo et al. |
| 6,579,301 B1 | 6/2003 | Bales et al. |
| 6,592,596 B1 | 7/2003 | Geitz |
| 6,605,037 B1 | 8/2003 | Moll et al. |
| 6,626,899 B2 | 9/2003 | Houser et al. |
| 6,632,227 B2 | 10/2003 | Adams |
| 6,656,194 B1 | 12/2003 | Gannoe et al. |
| 6,663,598 B1 | 12/2003 | Carrillo, Jr. et al. |
| 6,663,639 B1 | 12/2003 | Laufer et al. |
| 6,663,640 B2 | 12/2003 | Kortenbach |
| 6,675,809 B2 | 1/2004 | Stack et al. |
| 6,682,520 B2 | 1/2004 | Ingenito |
| 6,689,062 B1 | 2/2004 | Mesallum |
| 6,692,485 B1 | 2/2004 | Brock et al. |
| 6,716,222 B2 | 4/2004 | McAlister et al. |
| 6,733,512 B2 | 5/2004 | McGhan |
| 6,736,822 B2 | 5/2004 | McClellan et al. |
| 6,740,098 B2 | 5/2004 | Abrams et al. |
| 6,740,121 B2 | 5/2004 | Geitz |
| 6,746,460 B2 | 6/2004 | Gannoe et al. |
| 6,746,489 B2 | 6/2004 | Dua et al. |
| 6,754,536 B2 | 6/2004 | Swoyer et al. |
| 6,755,849 B1 | 6/2004 | Gowda et al. |
| 6,755,869 B2 | 6/2004 | Geitz |
| 6,756,364 B2 | 6/2004 | Barbier et al. |
| 6,764,518 B2 | 7/2004 | Godin |
| 6,773,440 B2 | 8/2004 | Gannoe et al. |
| 6,773,441 B1 | 8/2004 | Laufer |
| 6,786,898 B2 | 9/2004 | Guenst |
| 6,790,214 B2 | 9/2004 | Kraemer et al. |
| 6,802,868 B2 | 10/2004 | Silverman et al. |
| 6,821,285 B2 | 11/2004 | Laufer et al. |
| 6,830,546 B1 | 12/2004 | Chin et al. |
| 6,835,199 B2 | 12/2004 | McGuckin, Jr. et al. |
| 6,835,200 B2 | 12/2004 | Laufer et al. |
| 6,837,848 B2 | 1/2005 | Bonner et al. |
| 6,840,423 B2 | 1/2005 | Adams et al. |
| 6,845,776 B2 | 1/2005 | Stack et al. |
| 6,896,682 B1 | 5/2005 | McClellan et al. |
| 6,916,332 B2 | 7/2005 | Adams |
| 6,926,722 B2 | 8/2005 | Geitz |
| 6,966,919 B2 | 11/2005 | Sixto, Jr. et al. |
| 6,981,978 B2 | 1/2006 | Gannoe |
| 6,991,643 B2 | 1/2006 | Saadat |
| 6,994,715 B2 | 2/2006 | Gannoe et al. |
| 7,020,531 B1 | 3/2006 | Colliou et al. |
| 7,025,791 B2 | 4/2006 | Levine et al. |
| 7,033,373 B2 | 4/2006 | de al Torre et al. |
| 7,033,378 B2 | 4/2006 | Smith et al. |
| 7,033,384 B2 | 4/2006 | Gannoe et al. |
| 7,037,343 B2 | 5/2006 | Imran |
| 7,037,344 B2 | 5/2006 | Kagan et al. |
| 7,063,715 B2 | 6/2006 | Onuki et al. |
| 7,074,229 B2 | 7/2006 | Adams et al. |
| 7,083,629 B2 | 8/2006 | Weller et al. |
| 7,083,630 B2 | 8/2006 | DeVries et al. |
| 7,087,011 B2 | 8/2006 | Cabiri et al. |
| 7,097,650 B2 | 8/2006 | Weller et al. |
| 2001/0014800 A1 | 8/2001 | Frazier et al. |
| 2001/0020190 A1 | 9/2001 | Taylor |
| 2001/0037127 A1 | 11/2001 | De Hoyos Garza |
| 2002/0022851 A1 | 2/2002 | Kalloo et al. |
| 2002/0035361 A1 | 3/2002 | Houser et al. |
| 2002/0040226 A1 | 4/2002 | Laufer et al. |
| 2002/0047036 A1 | 4/2002 | Sullivan et al. |
| 2002/0058967 A1 | 5/2002 | Jervis |
| 2002/0072761 A1 | 6/2002 | Abrams et al. |
| 2002/0077661 A1 | 6/2002 | Saadat |
| 2002/0078967 A1 | 6/2002 | Sixto, Jr. et al. |
| 2002/0082621 A1 * | 6/2002 | Schurr et al. .................. 606/151 |
| 2002/0143346 A1 | 10/2002 | McGuckin, Jr. et al. |
| 2002/0165589 A1 | 11/2002 | Imran et al. |
| 2002/0183768 A1 | 12/2002 | Deem et al. |
| 2002/0193816 A1 | 12/2002 | Laufer et al. |
| 2003/0040804 A1 | 2/2003 | Stack et al. |
| 2003/0040808 A1 | 2/2003 | Stack et al. |
| 2003/0065340 A1 | 4/2003 | Geitz |
| 2003/0065359 A1 | 4/2003 | Weller et al. |

(56) References Cited

U.S. PATENT DOCUMENTS

| | | |
|---|---|---|
| 2003/0093117 A1 | 5/2003 | Saadat |
| 2003/0109892 A1 | 6/2003 | Deem et al. |
| 2003/0109931 A1 | 6/2003 | Geitz |
| 2003/0109935 A1 | 6/2003 | Geitz |
| 2003/0120265 A1 | 6/2003 | Deem et al. |
| 2003/0120285 A1 | 6/2003 | Kortenbach |
| 2003/0120289 A1 | 6/2003 | McGuckin, Jr. et al. |
| 2003/0132267 A1* | 7/2003 | Adams et al. ............ 227/176.1 |
| 2003/0158563 A1 | 8/2003 | McClellan et al. |
| 2003/0158601 A1 | 8/2003 | Silverman et al. |
| 2003/0171760 A1 | 9/2003 | Gambale |
| 2003/0208209 A1* | 11/2003 | Gambale et al. ............ 606/144 |
| 2003/0216754 A1 | 11/2003 | Kraemer et al. |
| 2003/0225312 A1 | 12/2003 | Suzuki et al. |
| 2004/0006351 A1 | 1/2004 | Gannoe et al. |
| 2004/0009224 A1 | 1/2004 | Miller |
| 2004/0010271 A1 | 1/2004 | Kortenbach |
| 2004/0024386 A1 | 2/2004 | Deem et al. |
| 2004/0037865 A1 | 2/2004 | Miller |
| 2004/0039452 A1 | 2/2004 | Bessler |
| 2004/0044354 A1 | 3/2004 | Gannoe et al. |
| 2004/0049209 A1 | 3/2004 | Benchetrit |
| 2004/0059349 A1 | 3/2004 | Sixto, Jr. et al. |
| 2004/0059354 A1 | 3/2004 | Smith et al. |
| 2004/0059358 A1 | 3/2004 | Kortenbach et al. |
| 2004/0082963 A1 | 4/2004 | Gannoe et al. |
| 2004/0087977 A1 | 5/2004 | Nolan et al. |
| 2004/0088008 A1 | 5/2004 | Gannoe et al. |
| 2004/0089313 A1 | 5/2004 | Utley et al. |
| 2004/0092892 A1 | 5/2004 | Kagan et al. |
| 2004/0092974 A1 | 5/2004 | Gannoe et al. |
| 2004/0097989 A1 | 5/2004 | Molina Trigueros |
| 2004/0107004 A1 | 6/2004 | Levine et al. |
| 2004/0116949 A1 | 6/2004 | Ewers et al. |
| 2004/0122456 A1 | 6/2004 | Saadat et al. |
| 2004/0122473 A1 | 6/2004 | Ewers et al. |
| 2004/0122526 A1 | 6/2004 | Imran |
| 2004/0133147 A1 | 7/2004 | Woo |
| 2004/0133238 A1 | 7/2004 | Cerier |
| 2004/0138525 A1 | 7/2004 | Saadat |
| 2004/0138526 A1 | 7/2004 | Guenst |
| 2004/0138529 A1 | 7/2004 | Wiltshire et al. |
| 2004/0138531 A1 | 7/2004 | Bonner et al. |
| 2004/0138682 A1 | 7/2004 | Onuki et al. |
| 2004/0147958 A1 | 7/2004 | Lam et al. |
| 2004/0148021 A1 | 7/2004 | Cartledge et al. |
| 2004/0148034 A1 | 7/2004 | Kagan et al. |
| 2004/0158331 A1 | 8/2004 | Stack et al. |
| 2004/0162568 A1 | 8/2004 | Saadat et al. |
| 2004/0167546 A1 | 8/2004 | Saadat et al. |
| 2004/0172141 A1 | 9/2004 | Stack et al. |
| 2004/0181242 A1 | 9/2004 | Stack et al. |
| 2004/0193190 A1* | 9/2004 | Liddicoat et al. ............ 606/153 |
| 2004/0194157 A1 | 9/2004 | Meguid |
| 2004/0194790 A1 | 10/2004 | Laufer et al. |
| 2004/0210243 A1 | 10/2004 | Gannoe et al. |
| 2004/0215180 A1 | 10/2004 | Starkebaum et al. |
| 2004/0220682 A1 | 11/2004 | Levine et al. |
| 2004/0225183 A1 | 11/2004 | Michlitsch et al. |
| 2004/0225194 A1 | 11/2004 | Smith et al. |
| 2004/0225305 A1 | 11/2004 | Ewers et al. |
| 2004/0236357 A1 | 11/2004 | Kraemer et al. |
| 2004/0249362 A1 | 12/2004 | Levine et al. |
| 2005/0010162 A1 | 1/2005 | Utley et al. |
| 2005/0021681 A1 | 1/2005 | Oommen |
| 2005/0033328 A1 | 2/2005 | Laufer et al. |
| 2005/0038415 A1 | 2/2005 | Rohr et al. |
| 2005/0038462 A1 | 2/2005 | Lubock |
| 2005/0049718 A1 | 3/2005 | Dann et al. |
| 2005/0055038 A1* | 3/2005 | Kelleher et al. ............ 606/151 |
| 2005/0055039 A1 | 3/2005 | Burnett et al. |
| 2005/0075622 A1 | 4/2005 | Levine et al. |
| 2005/0075653 A1 | 4/2005 | Saadat et al. |
| 2005/0080438 A1 | 4/2005 | Weller et al. |
| 2005/0080444 A1 | 4/2005 | Kraemer et al. |
| 2005/0085787 A1 | 4/2005 | Laufer |
| 2005/0096673 A1 | 5/2005 | Stack et al. |
| 2005/0096750 A1 | 5/2005 | Kagan et al. |
| 2005/0119671 A1 | 6/2005 | Reydel et al. |
| 2005/0119674 A1 | 6/2005 | Gingras |
| 2005/0143760 A1 | 6/2005 | Imran |
| 2005/0148818 A1 | 7/2005 | Mesallum |
| 2005/0149067 A1 | 7/2005 | Takemoto et al. |
| 2005/0149114 A1 | 7/2005 | Cartledge et al. |
| 2005/0177176 A1 | 8/2005 | Gerbi et al. |
| 2005/0192599 A1* | 9/2005 | Demarais ............ 606/151 |
| 2005/0192601 A1 | 9/2005 | Demarais |
| 2005/0194038 A1 | 9/2005 | Brabec et al. |
| 2005/0194294 A1 | 9/2005 | Oexle et al. |
| 2005/0194312 A1 | 9/2005 | Niemeyer et al. |
| 2005/0195925 A1 | 9/2005 | Traber |
| 2005/0195944 A1 | 9/2005 | Bartels et al. |
| 2005/0196356 A1 | 9/2005 | Leinen et al. |
| 2005/0197540 A1 | 9/2005 | Liedtke |
| 2005/0197622 A1 | 9/2005 | Blumenthal et al. |
| 2005/0197684 A1 | 9/2005 | Koch |
| 2005/0198476 A1 | 9/2005 | Gazsi et al. |
| 2005/0203547 A1 | 9/2005 | Weller et al. |
| 2005/0203548 A1 | 9/2005 | Weller et al. |
| 2005/0228415 A1 | 10/2005 | Gertner |
| 2005/0228504 A1 | 10/2005 | Demarais |
| 2005/0256533 A1 | 11/2005 | Roth et al. |
| 2005/0256587 A1 | 11/2005 | Egan |
| 2006/0020247 A1 | 1/2006 | Kagan et al. |
| 2006/0020254 A1 | 1/2006 | Hoffmann |
| 2006/0020276 A1 | 1/2006 | Saadat et al. |
| 2006/0036267 A1 | 2/2006 | Saadat et al. |
| 2006/0106288 A1 | 5/2006 | Roth et al. |
| 2006/0111735 A1 | 5/2006 | Crainich |
| 2006/0122462 A1 | 6/2006 | Roth et al. |
| 2006/0142787 A1 | 6/2006 | Weller et al. |
| 2006/0151568 A1 | 7/2006 | Weller et al. |
| 2007/0167960 A1 | 7/2007 | Roth et al. |
| 2007/0233161 A1 | 10/2007 | Weller et al. |

FOREIGN PATENT DOCUMENTS

| | | |
|---|---|---|
| EP | 0 174 843 A1 | 3/1986 |
| EP | 0 246 999 A1 | 11/1987 |
| EP | 0 540 010 A2 | 5/1993 |
| EP | 0668057 A2 | 8/1995 |
| EP | 1728475 A2 | 6/2006 |
| JP | 63277063 A | 11/1988 |
| JP | 63279854 | 11/1988 |
| JP | 63302863 A | 12/1988 |
| JP | 01049572 A | 2/1989 |
| JP | 04297219 | 10/1992 |
| WO | WO 94/18893 A1 | 9/1994 |
| WO | WO 99/17662 A1 | 4/1999 |
| WO | WO 99/53827 A1 | 10/1999 |
| WO | WO 00/32137 A1 | 6/2000 |
| WO | WO 00/48656 A1 | 8/2000 |
| WO | WO 00/78227 A1 | 12/2000 |
| WO | WO 00/78229 A1 | 12/2000 |
| WO | WO 01/66018 A1 | 9/2001 |
| WO | WO 01/67964 A2 | 9/2001 |
| WO | WO 01/85034 A1 | 11/2001 |
| WO | WO 02/24080 A2 | 3/2002 |
| WO | WO 02/35980 A2 | 5/2002 |
| WO | WO 02/39880 A2 | 5/2002 |
| WO | WO 02/071951 A1 | 9/2002 |
| WO | WO 02/091961 A1 | 11/2002 |
| WO | WO 02/096327 A2 | 12/2002 |
| WO | WO 03/007796 A2 | 1/2003 |
| WO | WO 03/017882 A2 | 3/2003 |
| WO | WO 03/078721 A2 | 9/2003 |
| WO | 03086247 | 10/2003 |
| WO | WO 03/086247 A1 | 10/2003 |
| WO | WO 03/088844 A1 | 10/2003 |
| WO | WO 03/094785 A1 | 11/2003 |
| WO | 03099140 A1 | 12/2003 |
| WO | 03105563 A2 | 12/2003 |
| WO | 03105671 A2 | 12/2003 |
| WO | WO 03/099140 | 12/2003 |

(56) References Cited

FOREIGN PATENT DOCUMENTS

| WO | WO 03/105563 | 12/2003 |
| --- | --- | --- |
| WO | WO 03/105671 | 12/2003 |
| WO | WO 2004/009269 A2 | 1/2004 |
| WO | WO 2004/014237 A1 | 2/2004 |
| WO | 2004/019788 A2 | 3/2004 |
| WO | WO 2004/017863 A2 | 3/2004 |
| WO | WO 2004/019787 | 3/2004 |
| WO | WO 2004/019826 A1 | 3/2004 |
| WO | WO 2004/037064 A2 | 5/2004 |
| WO | WO 2004/049911 A2 | 6/2004 |
| WO | WO 2004/058102 A2 | 7/2004 |
| WO | WO 2004/060150 A1 | 7/2004 |
| WO | WO 2004/087014 A2 | 10/2004 |
| WO | 2004/110285 A1 | 12/2004 |
| WO | WO 2004/103189 A1 | 12/2004 |
| WO | WO 2005/023118 A1 | 3/2005 |
| WO | WO 2005/037152 A1 | 4/2005 |
| WO | WO 2005/058239 A2 | 6/2005 |
| WO | WO 2005/060882 A1 | 7/2005 |
| WO | 2005092210 A1 | 10/2005 |
| WO | WO 2006/078781 A1 | 7/2006 |
| WO | 2006112849 | 11/2006 |

OTHER PUBLICATIONS

U.S. Appl. No. 10/686,326, filed Oct. 14, 2003, Weller et al.

Benjamin, S.B., et al., *A Double-Blind Cross Over Study of the Garren-Edwards anti-Obesity Bubble* Abstract Submitted to A/S/G/E/ 1987, Georgetown University Hospital and Fairfax Hospital, Washington, D.C. and Fairfax, VA.

Benjamin, S.B., *Small Bowel Obstruction and the Garren-Edwards Bubble, Lessons to be Learned*? Abstracts Submitted to A/S/G/E 1987, Division of Gastroenterology, Department of Medicine, Georgetown University Hospital, Washington, D.C.

Boyle, Thomas M., M.D., et al., Small Intestinal Obstruction Secondary to Obturation by a Garren Gastric Bubble, *The American Journal of Gastroenterology*, vol. 82, No. 1, pp. 51-53, 1987.

Büchler, M.W., M.D. et al., A Technique for Gastroplasty as a Substitute for the Esophagus: Fundus Rotation Gastroplasty, *Journal of the American College of Surgeons*, vol. 182, pp. 241-245, Mar. 1996.

Cass, O.W., et al., *Long-Term Follow-Up of Patients With Percutaneous Endoscopic Gastrostomy (PEG)*, Abstracts Submitted to A/S/G/E 1987, Department of Medicine, Hennepin County Medical Center, Minneapolis, MN 55415.

Chang, Craig G. M.D., et al.. Gastro-Clip® Gastroplasty: A Very Long-Term Complication, *Obesity Surgery*, 14, © FD-Communications Inc . . . 2004.

Clark, Charlene, R.N., The Gastric Bubble: Medicine, Magic or Mania? *SGA Journal*, vol. 9, No. 2, pp. 45-47, Fall 1986.

Cummings, David E., M.D., et al., Plasma Ghrelin Levels After Diet-Induced Weight Loss or Gastric Bypass Surgery, *New England Journal of Medicine*, vol. 346, No. 21, pp. 1623-1630, May 23, 2002.

Davenport, Horace W., Ph.D., D.Sc., *Physiology of the Digestive Tract: An Introductory Text*, 3d Ed., Cover and Table of Contents.

DeMeester, Tom T., M.D., Evolving Concepts of Reflux: The Ups and Downs of the LES, *Canadian Journal of Gastroenterology*, vol. 16, No. 5, pp. 327-331, 2002.

De Waele, B., M.D., et al., Intragastric Balloons for Preoperative Weight Reduction, *Obesity Surgery*, vol. 10, pp. 58-60, 2000.

Edell, Steven L., et al., Radiographic Evaluation of the Garren Gastric Bubble, *American Journal of Radiology*, vol. 145, pp. 49-50, Jul. 1985.

Endo Gia Universal, Single UseStapler and Endo GIA Roticulator, Brochure, 8 pages, Undated.

Filipi, Charles J. M.D., et al., Transoral, Flexible Endoscopic Suturing for Treatment of GERD: A Multicenter Trial, *Gastrointestinal Endoscooy*,. vol. 53, No. 4, pp. 416-422, 2001.

Gray, Henry, R.R.S., *Anatomy of the Human Body*, The Digestive System, Thirtieth American Edition, pp. 1466-1467 (Undated).

Guidant, Internet, AXIUS™ Vacuum 2 Stabilizer Systems, Internet Website—www.guidant.com/products/axius_vacuum.shtml, 8 pages, visited May 27, 2003.

Gukovsky-Reicher, S., M.D. et al., Expandable Metal Esophageal Stents: Efficiacy and Safety. Review of Current Literature Data and of 53 Stents Placed at Harbor-UCLA Medical Center, www.medscape.com/viewarticle/423508_print pp. 1-20, Medscape General Medicine 4(1), 2003 © 2002 Medscape, downloaded Oct. 9, 2006.

Hepworth, Clive C. FRCS et al., Mechanical Endoscopic Methods of Haemostasis for Bleeding Peptic Ulcers: A Review, *Bailliere's Clinical Gastroenterology*, vol. 14, No. 3 pp. 467-476, 2000.

Ikeda, Y. et al., New Suturing Device for Transanal Endoscopic Microsurgery, *Blackwell Science Ltd.* p. 1290, 1997.

Johnson & Johnson Gateway Endopath 3mm, 5mm and 10 mm Diameter Endoscopic Instruments. Internet Website—www.inigateway.com/home.ihtml?loc=USENG&page=viewContent&parentId-0900 . . . , 3 pages, visited May 29, 2003.

Kirby, Donald F., Incomplete Small Bowel Obstruction by the Garren-Edwards Gastric Bubble Necessitating Surgical Intervention, *The American Journal of Gastroenterology*, vol. 82, No. 3, pp. 251-253, 1987.

Nieben, Ole Gyring, et al., Intragastric Balloon as an Artificial Bezoar for Treatment of Obesity, *The Lancet*, pp. 198-199, Jan. 23, 1982.

Percival, Walter L., M.D., "The Balloon Diet": A Noninvasive Treatment for Morbid Obesity. Preliminary Report of 1908 Patients, *The Canadian Journal of Surgery*, vol. 27, No. 2, pp. 135-136.

Power Medical Interventions Digital and Wireless Medical Technology, Product Innovation: SurgASSIST™, Internet Website—www/pmi2.com/access_flexibility.asp, 6 pages, visited May 29, 2003.

Snowden Pencer, Diamon-Flex Angled Snake Retractor (class 1, 878.4800), Appendix F.f, Undated.

Stoltenberg, P.H., et al., *Intragastric Balloon Therapy of Obesity: A Randomized Double-Blind Trial*, Abstracts of Papers 1985, Scott & White Clinic, Texas A&M College of Medicine, Temple, Texas.

Swain, C. Paul, M.D. et al., An Endoscopic Sewing Machine, *Gastrointestinal Edoscony*, vol. 32, No. 1 pp. 36-38 1986.

Swain, C. Paul, M.D., Endoscopic Sewing and Stapling Machines, *Endoscopy* pp. 205-210, © Georg Thieme Verlag Stuttgart, New York, 1997.

Swain, C. Paul, M.D. et al., An Endoscopic Stapling Device: The Development of a New Flexible Endoscopically Controlled Device for Placing Multiple Transmural Staples in Gastrointestinal Tissue, *Gastrointestinal Endoscopy*, vol. 35, No. 4, pp. 338-339, 1989.

Swain, C. Paul, M.D., Endoscopic Suturing. *Bailliere's Clinical Gastroenterology*, Bailliere's Tindall,, vol. 13 No. 1, pp. 97-108, 1999.

Taylor, T. Vincent, et al., Gastric Balloons for Obesity, *The Lancet*, Abstract, Mar. 27, 1982.

Vandenplas, Y., et al., Intragastric Balloons in Adolescents With Morbid Obesity, *European Journal of Gastroenterology & Hepatology*, vol. 11, No. 3, pp. 243-245, 1999.

Villar, Hugo V., M.D., et al., Mechanisms of Satiety and Gastric Emptying After Gastric Partitioning and Bypass, *Surgery*, pp. 229-236, Aug. 1981.

Wullstein, C., et al., Compression Anastomosis (AKA-2) in Colorectal Surgery: Results in 442 Consecutive Patients, *British Journal of Surgery 2000*, pp. 1071-1075.

U.S. Appl. No. 60/234,360.

Japanese Office Action issued Dec. 9, 2011 for Application No. 2008-548626 (4 Pages).

* cited by examiner

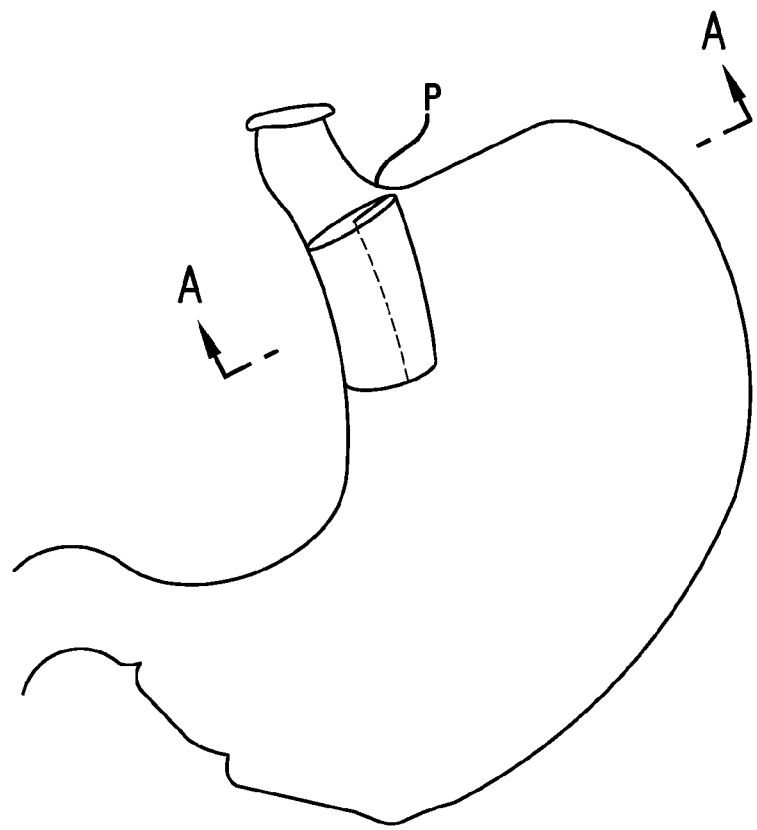
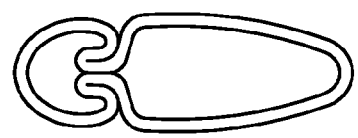
FIG. 5H

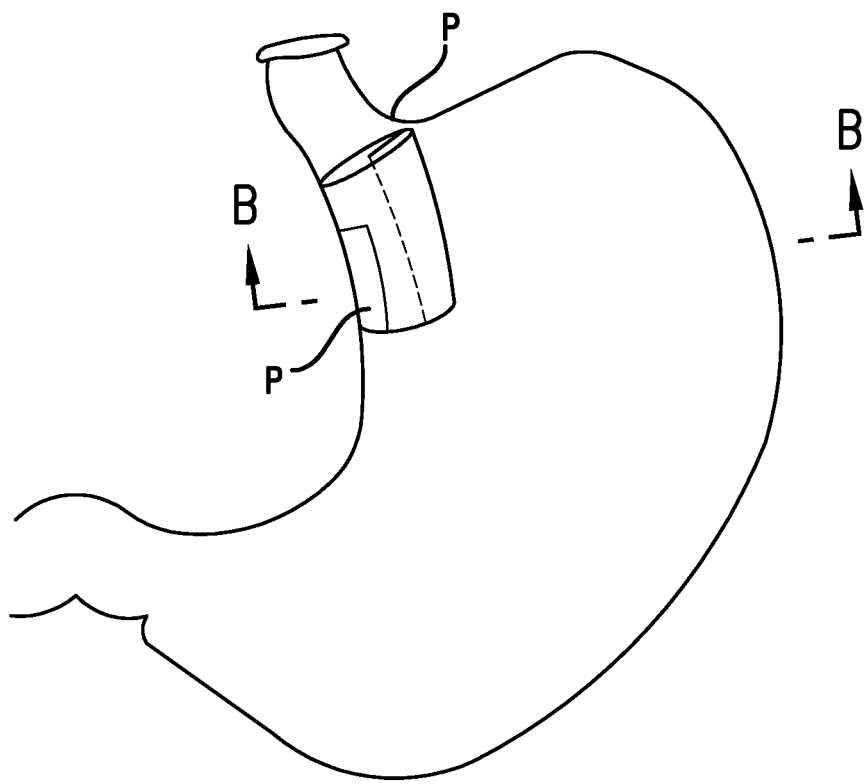
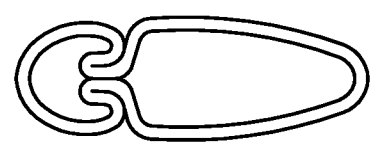
B-B
FIG. 51

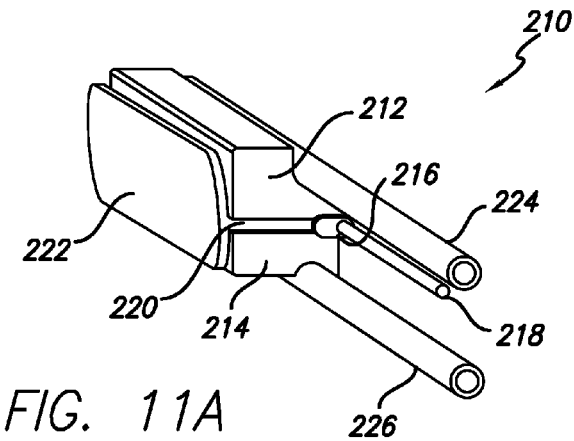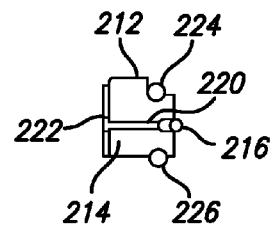
FIG. 11A    FIG. 11B
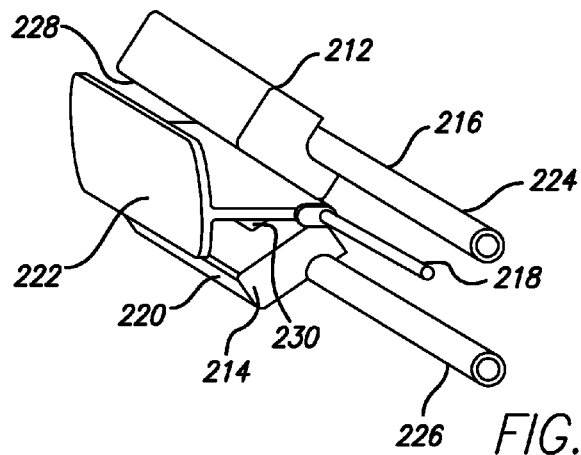
FIG. 11C
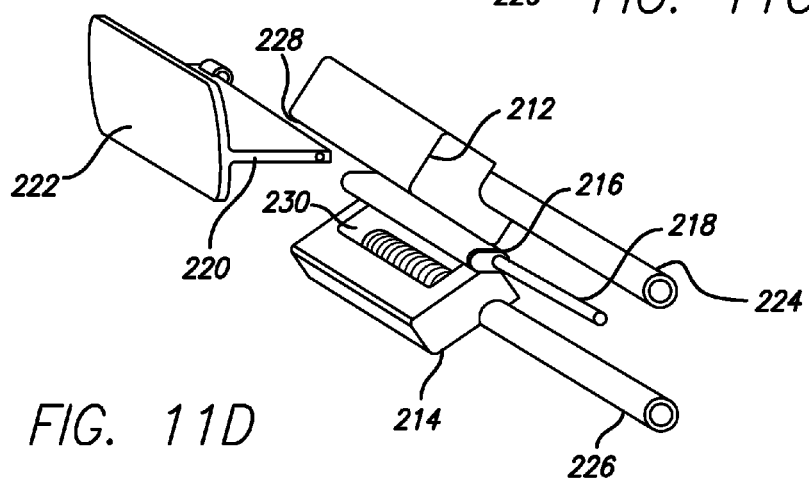
FIG. 11D

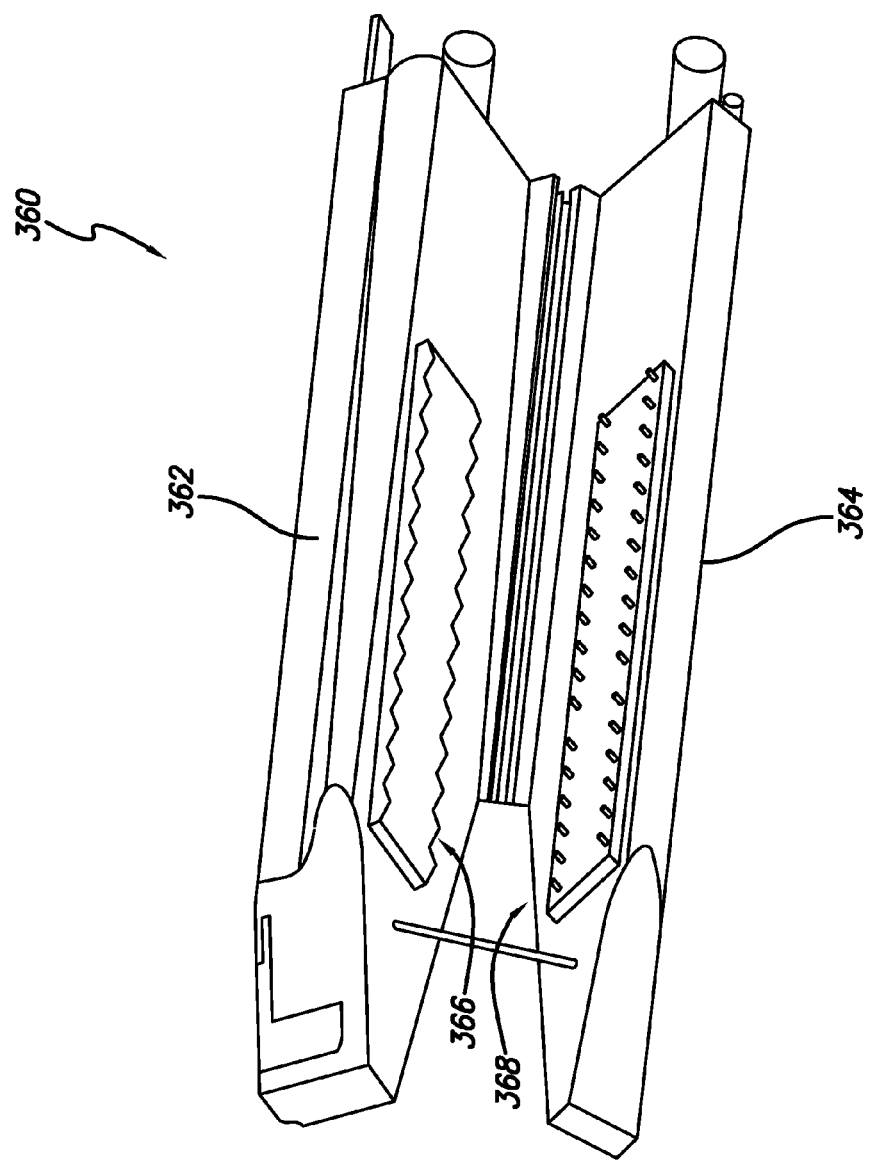

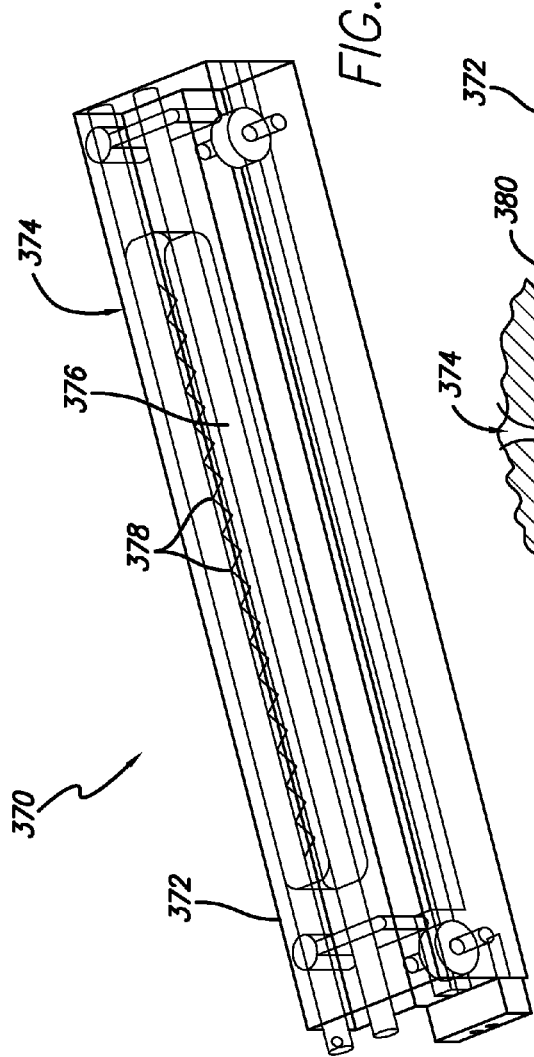
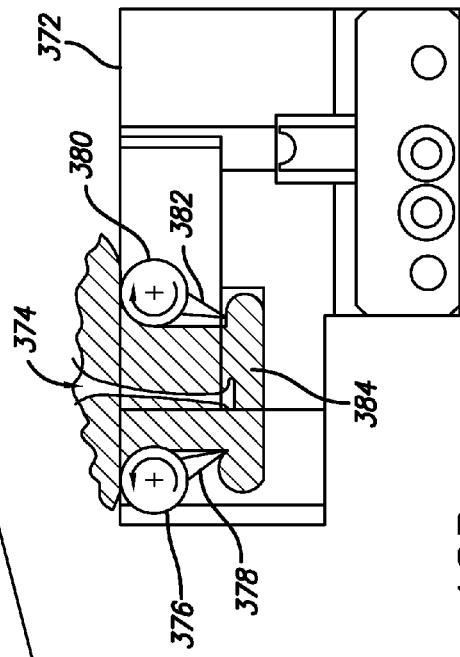
FIG. 18A
FIG. 18B

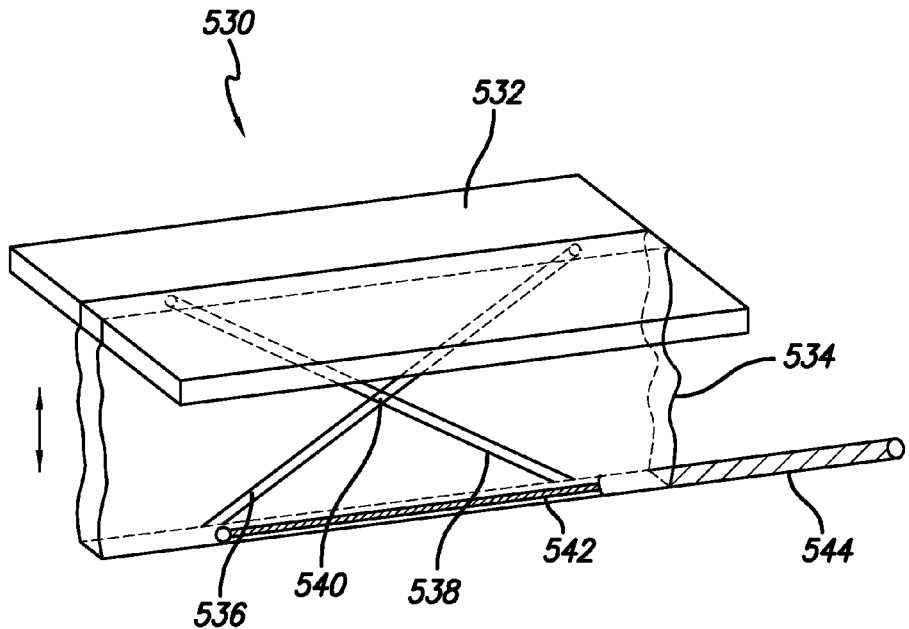
FIG. 25A
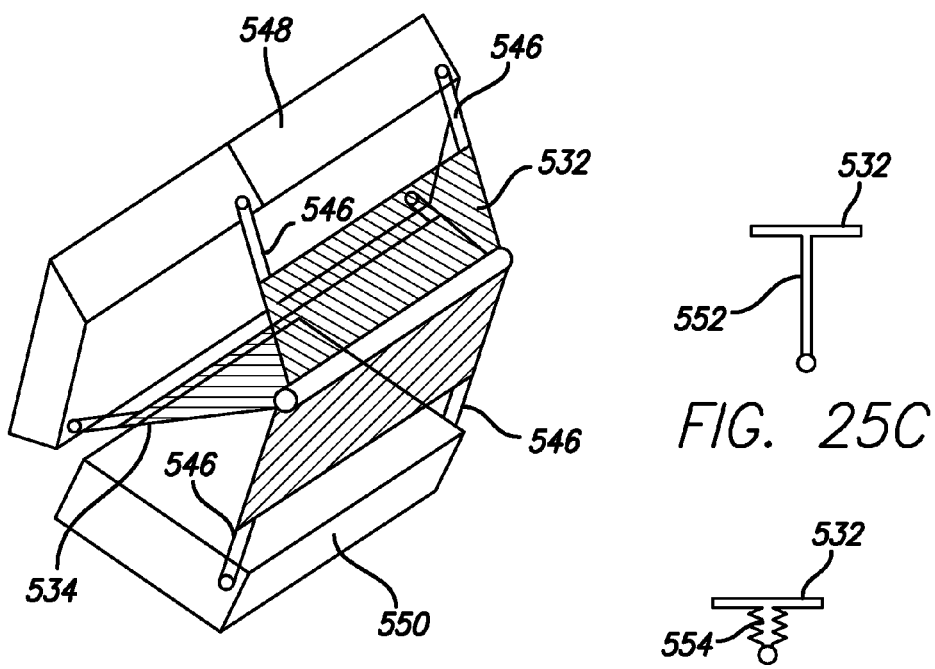
FIG. 25B
FIG. 25C
FIG. 25D

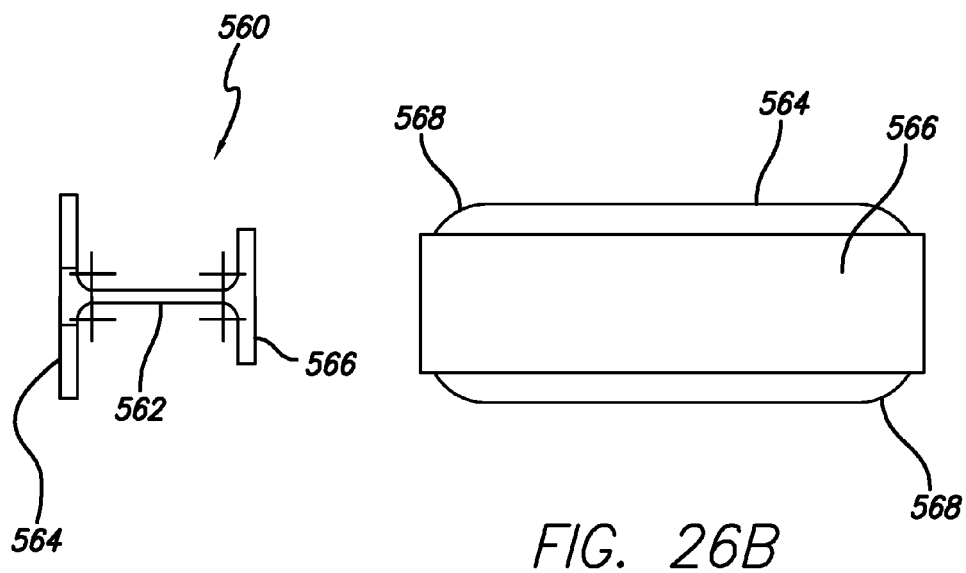
FIG. 26A
FIG. 26B
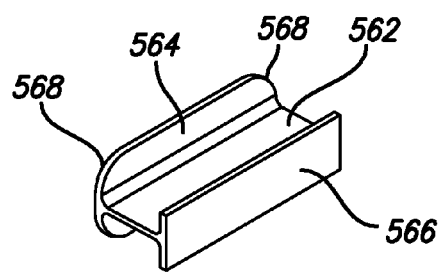
FIG. 26C

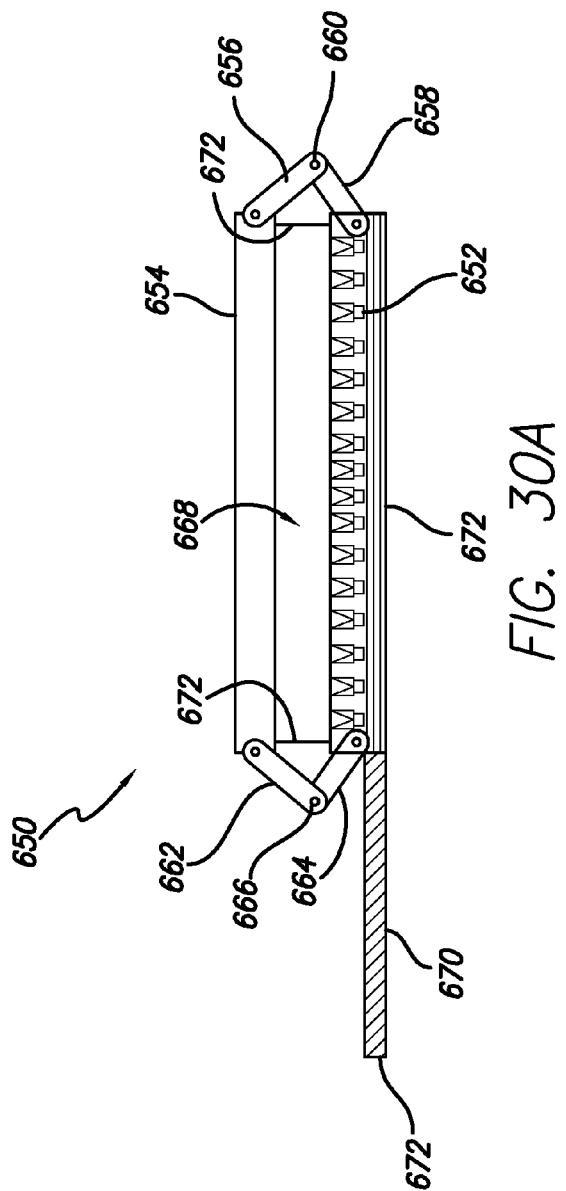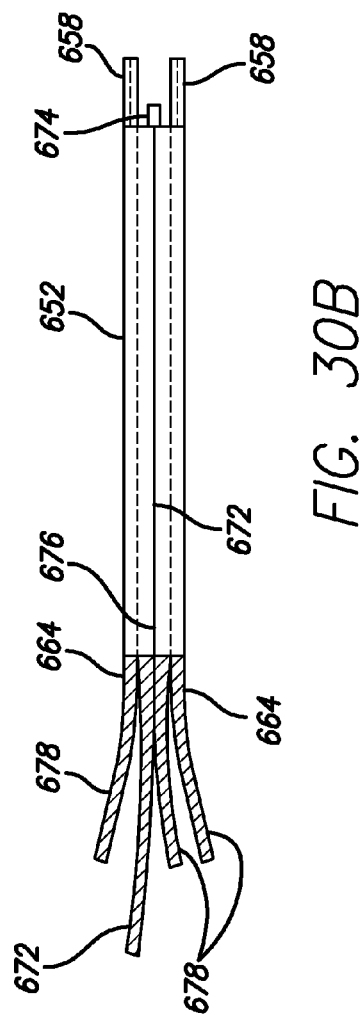
FIG. 30A
FIG. 30B

DEVICES AND METHODS FOR PLACEMENT OF PARTITIONS WITHIN A HOLLOW BODY ORGAN

FIELD OF THE INVENTION

The present invention relates generally to medical devices and methods. More particularly, it relates to devices and methods for creating a partition within a hollow body organ, particularly a stomach, intestinal tract, or other region of the gastrointestinal tract, and affixing the tissue.

BACKGROUND OF THE INVENTION

In cases of severe obesity, patients may currently undergo several types of surgery either to tie off or staple portions of the large or small intestine or stomach, and/or to bypass portions of the same to reduce the amount of food desired by the patient, and the amount absorbed by the gastrointestinal tract. The procedures currently available include laparoscopic banding, where a device is used to "tie off" or constrict a portion of the stomach, vertical banded gastroplasty (VBG), or a more invasive surgical procedure known as a Roux-En-Y gastric bypass to effect permanent surgical reduction of the stomach's volume and subsequent bypass of the intestine.

Typically, these stomach reduction procedures are performed surgically through an open incision and staples or sutures are applied externally to the stomach or hollow body organ. Such procedures can also be performed laparoscopically, through the use of smaller incisions, or ports, through trocars and other specialized devices. In the case of laparoscopic banding, an adjustable band is placed around the proximal section of the stomach reaching from the lesser curve of the stomach around to the greater curve, thereby creating a constriction or "waist" in a vertical manner between the esophagus and the pylorus. During a VBG, a small pouch (approximately 20 cc in volume) is constructed by forming a vertical partition from the gastroesophageal junction to midway down the lesser curvature of the stomach by externally applying staples, and optionally dividing or resecting a portion of the stomach, followed by creation of a stoma at the outlet of the partition to prevent dilation of the outlet channel and restrict intake. In a Roux-En-Y gastric bypass, the stomach is surgically divided into a smaller upper pouch connected to the esophageal inflow, and a lower portion, detached from the upper pouch but still connected to the intestinal tract for purposes of secreting digestive juices. A resected portion of the small intestine is then anastomosed using an end-to-side anastomosis to the upper pouch, thereby bypassing the majority of the intestine and reducing absorption of caloric intake and causing rapid "dumping" of highly caloric or "junk foods."

Although the outcome of these stomach reduction surgeries leads to patient weight loss because patients are physically forced to eat less due to the reduced size of their stomach, several limitations exist due to the invasiveness of the procedures, including time, use of general anesthesia, time and pain associated with the healing of the incisions, and other complications attendant to major surgery. In addition, these procedures are only available to a small segment of the obese population (morbid obesity, Body Mass Index≥40) due to their complications, leaving patients who are considered obese or moderately obese with few, if any, interventional options.

In addition to surgical procedures, certain tools exist for securing tissue such as the stapling devices used in the above-described surgical procedures and others such as in the treatment of gastroesophageal reflux disease (GERD). These devices include the GIA® device (Gastrointestinal Anastomosis device manufactured by Ethicon Endosurgery, Inc. and a similar product by USSC), and certain clamping and stapling devices as described in U.S. Pat. Nos. 5,403,326; 5,571,116; 5,676,674; 5,897,562; 6,494,888; and 6,506,196 for methods and devices for fundoplication of the stomach to the esophagus for the treatment of gastroesophageal reflux disease (GERD). In addition, certain tools, such as those described in U.S. Pat. Nos. 5,788,715 and 5,947,983, detail an endoscopic suturing device that is inserted through an endoscope and placed at the site where the esophagus and the stomach meet. Vacuum is then applied to acquire the adjacent tissue, and a series of stitches are placed to create a pleat in the sphincter to reduce the backflow of acid from the stomach up through the esophagus. These devices can also be used transorally for the endoscopic treatment of esophageal varices (dilated blood vessels within the wall of the esophagus).

There is a need for improved devices and procedures. In addition, because of the invasiveness of most of the surgeries used to treat obesity and other gastric disorders such as GERD, and the limited success of others, there remains a need for improved devices and methods for more effective, less invasive hollow organ restriction procedures.

BRIEF SUMMARY OF THE INVENTION

Devices for tissue acquisition and fixation, or gastroplasty, are described that may be utilized for creating a partition within a hollow body organ, such as the stomach, esophageal junction, and other portions of the gastrointestinal tract. Generally, the devices of the system may be advanced in a minimally invasive manner within a patient's body, e.g., transorally, endoscopically, percutaneously, etc., to create one or several divisions or plications within the hollow body organ. Such divisions or plications can form restrictive barriers within the organ, or can be placed to form a pouch, or gastric lumen, smaller than the remaining stomach volume to essentially act as the active stomach such as the pouch resulting from a surgical Roux-En-Y gastric bypass procedure. Examples of placing and/or creating divisions or plications may be seen in further detail in U.S. Pat. No. 6,558,400; U.S. patent application Ser. No. 10/188,547 filed Jul. 2, 2002; and U.S. patent application Ser. No. 10/417,790 filed Apr. 16, 2003, each of which is incorporated herein by reference in its entirety.

The devices may be advanced within a body through a variety of methods, e.g., transorally, transanally, endoscopically, percutaneously, etc., to create one or several divisions or plications within a hollow body organ, e.g., to create a gastric lumen or partition to reduce the effective active area of the stomach (e.g., that which receives the initial food volume), performed from within the stomach cavity. The creation of this smaller gastric lumen may be achieved in a minimally invasive procedure completely from within the stomach cavity. Moreover, the devices are configured such that once acquisition of the tissue is accomplished, manipulation of the acquired tissue is unnecessary as the devices are able to automatically configure the acquired tissue into a desired configuration.

The devices may generally comprise a first acquisition member and a second acquisition member in apposition to one another along a first longitudinal axis, wherein optionally, at least one of the acquisition members is adapted to adhere tissue thereto such that the tissue is positioned between the first and second acquisition members, and optionally wherein at least one of the acquisition members is movable relative to the first longitudinal axis between a delivery configuration and a deployment configuration. Moreover, the system may also comprise a septum, or separator, removably positioned between the first and second acquisition members, wherein at least one of the acquisition members is movable relative to the septum between a delivery configuration and a deployment configuration.

A handle may be located at a proximal end of an elongate body or member and used to manipulate the device advanced within the hollow body organ as well as control the opening and clamping of the acquisition members onto the tissue. The elongate body may be comprised of a series of links, or of an extrusion fabricated with various lumens to accommodate the various control mechanisms of the acquisition device. Similarly, the control mechanisms may be grouped together and sheathed in a thin skin sheath, such as a heat shrink. A working lumen may extend entirely through the elongate member and may be sized to provide access to the distal end for various surgical tools, such as an endoscope or other visualization device, or therapeutic devices such as snares, excisional tools, biopsy tools, etc. once the distal end of the assembly is positioned within the hollow body organ. The acquisition members may be joined to the elongate body via a passive or active hinge member, adaptable to position the assembly. The acquisition members may generally comprise a cartridge member placed longitudinally in apposition to an anvil member. The cartridge member may contain one or several fasteners, e.g., staples, clips, etc., which may be actuated via controls located proximally on the handle assembly. Moreover, the septum or barrier may be removably positioned between the cartridge member and anvil member and used to minimize or eliminate cross acquisition of the tissue into the cartridge member and/or anvil member.

Methods of placing a partition from within a hollow body organ using the devices disclosed herein generally comprise positioning a first acquisition member and a second acquisition member adjacent to a region of tissue within the hollow body organ, wherein the first and second acquisition members are in apposition to one another along a first longitudinal axis, adhering tissue from the region to each of the first and second acquisition members, and securing the adhered tissue between the first and second acquisition members. Such a method may also involve pivoting at least one of the acquisition members about the longitudinal axis to an open or closed configuration. Another method may also comprise removing a septum from between the first acquisition member and the second acquisition member.

While the device is in a delivery configuration, i.e., where the components of the distal working portion of the device (the cartridge member and anvil member) are disposed such that the cartridge and anvil are directly positioned into apposition about the septum. Once desirably positioned, one or both of the cartridge member and anvil member may be rotated about a pivot or translationally moved in parallel to one another. Then, portions of the stomach wall may be acquired by, or drawn within their respective openings. The configuration of the cartridge member and anvil member and the positioning of the device within the stomach are such that this tissue acquisition procedure also enables the devices to be self-adjusting with respect to the acquired tissue. Moreover, the devices are configured such that portions of the stomach wall are automatically positioned for fixation upon being acquired and the tissue becomes automatically adjusted or tensioned around the perimeter of the distal working portion of the device in the stomach and within the distal working portion inner volume, to achieve the desired resulting geometry (e.g., small gastric pouch or restrictive partition or baffle). Because of the manner in which the tissue is acquired, the tissue intimately surrounds the cartridge member and anvil member to define or calibrate the subsequent volume of the resulting gastric lumen. Thus, the gastric volume may be predetermined by adjusting the volume of the cartridge member and anvil member, or the use of accessory devices such as a scope or balloon. As a result, once the desired volume is known and incorporated in the device, the user can achieve a controlled acquisition and without intraprocedural adjustments or positioning requirements.

The septum may act effectively as a barrier between the openings to facilitate the acquisition of the tissue to their respective openings while minimizing or eliminating cross acquisition of the tissue into the cartridge member and/or anvil member. In other alternatives, the septum may be omitted from the device and acquisition of the tissue may be accomplished by sequentially activating vacuum forces within the openings. Once the tissue has been acquired, the septum may be removed from between the cartridge member and anvil member by translating the septum distally or proximally of the cartridge member and anvil member or left within the stomach for later removal.

BRIEF DESCRIPTION OF THE DRAWINGS

FIGS. 5H and 5I show perspective and cross sectional views of illustrative tissue configurations that may be formed with the gastroplasty devices and methods described herein.

FIGS. 11A and 11B show perspective and end views, respectively, of another variation of a suitable gastroplasty device.

FIGS. 11C and 11D show perspective views of a gastroplasty device with and without a septum, respectively.

FIG. 17 shows a perspective view of a device having an optional feature of projections or serrations which may be defined along the mating surfaces of the cartridge member and/or anvil member.

FIGS. 18A and 18B show perspective and cross-sectional end views, respectively, of another optional feature of one or more rotatable shafts which may be integrated into the device.

FIGS. 25A and 25B show perspective views of an alternative septum assembly having a collapsible septum member.

FIGS. 25C and 25D show end views of the septum of FIG. 25A in an expanded or extended configuration and in a collapsed configuration.

FIGS. 26A to 26C show end, bottom, and perspective views, respectively, of yet another alternative septum having radiused corners.

FIGS. 30A and 30B show side and edge views of an alternative gastroplasty device, utilizing linked pod members.

DETAILED DESCRIPTION OF THE INVENTION

Figure 1A:
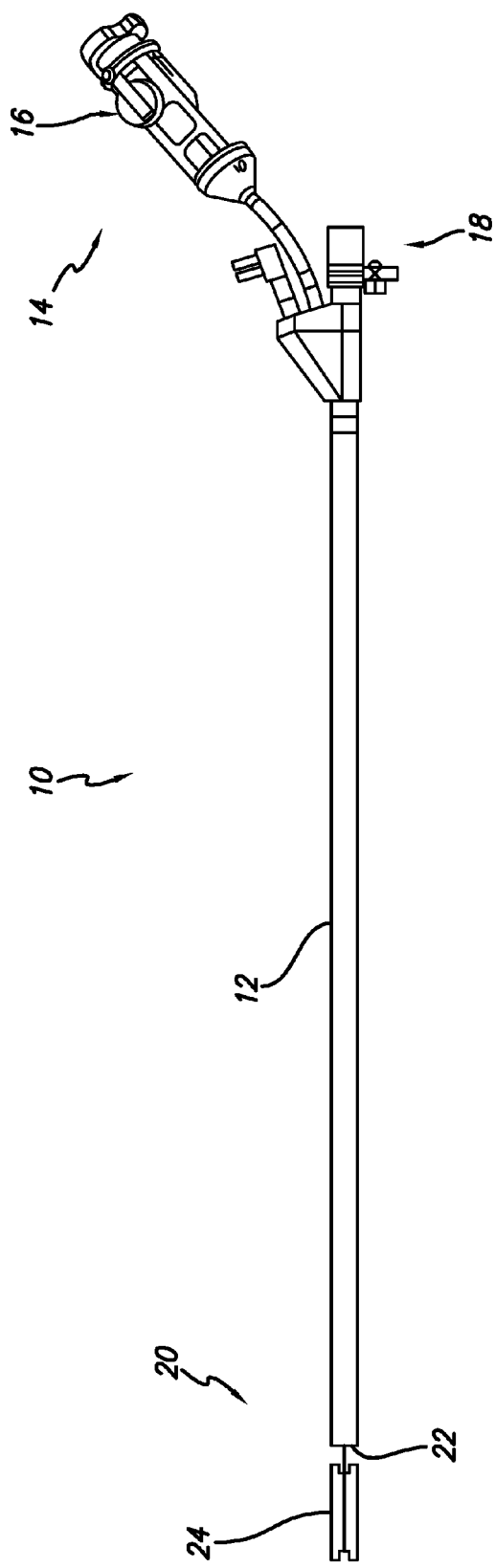
FIGS. 1A and 1B show side and detailed side views, respectively, of one variation of an exemplary gastroplasty device described herein.

Gastroplasty devices for tissue acquisition and fixation, and methods of using them are described. In general, the gastroplasty devices described herein may be utilized for creating a partition within a hollow body organ, such as the stomach, esophageal junction, and/or other portions of the gastrointestinal tract. The gastroplasty devices may be advanced within a body through a variety of methods, e.g., transorally, transanally, endoscopically, percutaneously, etc., to create one or several divisions or plications within the hollow body organ, e.g., to create a gastric lumen within the stomach. Further, the gastroplasty devices may be assisted through the use of laparoscopic guidance, in particular, visualization of the external surface of the hollow body organ to assist in placement of the device, or within the organ cavity to monitor the procedure. Similarly, the devices of the present invention may be used in conjunction with other laparoscopic procedures, or may further be modified by an additional step or procedure to enhance the geometry of the partition. For example, upon placement of a partition of the present invention, it may be desirable to perform a secondary step either transorally, or laparoscopically, to achieve the desired gastroplasty geometry, such as the placement of a single fold or plication within the gastric lumen or pouch as described in U.S. patent application Ser. No. 10/188,547, which was filed Jul. 2, 2002 and is incorporated by reference herein in its entirety, to further restrict the movement of food through the pouch, or the laparoscopic placement of a band, clip, ring or other hollow reinforcement member at the outlet of the gastric lumen such as is done in a VBG, or lap-band procedure to reinforce or narrow the outlet of the lumen.

The gastroplasty devices described here, allow for the creation of a smaller gastric lumen to be achieved in a minimally invasive surgical procedure completely from within the stomach cavity. Moreover, the devices described herein are configured such that once acquisition of the tissue is accomplished, any manipulation of the acquired tissue is unnecessary as the devices are able to automatically configure the acquired tissue into a desired configuration whereby the geometry of the devices regulates or prescribes the resulting tissue geometry at the time of acquisition. In operation, the perimeter of the device, and any openings therein, form the template or mold cavity around and into which tissue flows, thereby creating a tissue structure that reflects the geometry of the mold. That is, as the devices are configured such that portions of the stomach wall are automatically positioned for fixation upon being acquired, and the tissue becomes automatically adjusted or tensioned around the perimeter of the distal working portion of the device in the stomach and within the distal working portion inner volume, to achieve the desired resulting geometry (e.g., small gastric pouch or restrictive partition or baffle). Because of the manner in which the tissue is acquired, the tissue intimately surrounds the cartridge member and anvil member to define or calibrate the subsequent volume of the resulting gastric lumen. Thus, the gastric volume may be predetermined by adjusting the volume of the cartridge member and anvil member. As a result, once the desired volume is known and incorporated in the device, the user can achieve a controlled acquisition and without intraprocedural adjustments or positioning requirements. Subsequent manipulation of the tissue may be performed, if desired, to effect certain configurations; however, this manipulation may be omitted entirely.

Turning to the figures, FIG. 1A shows a side view of one variation of gastroplasty assembly 10. Assembly 10 may be generally comprised of an elongate tubular member 12 having handle assembly 16 connected at a proximal end 14. An integrated access assembly 18 may also be connected at proximal end 14 for providing access to working lumen 22 defined within elongate member 12. Elongate member 12 may have a circular or elliptical cross-sectional area. Alternatively, the cross-sectional area may take on any number of different cross-sectional configurations, e.g., hexagonal, octagonal, etc., provided that it presents an atraumatic surface to the tissue surfaces within the body. In addition, elongate member 12 may be curved, or may comprise a series of links as described in U.S. patent application Ser. No. 10/686,326, which was filed on Oct. 14, 2003, and is incorporated by reference in its entirety herein. In this way, a curved or flexible elongate member, or an elongate member comprising a series of links will help to increase the flexibility of the elongate member, and hence increase the ease in which the device is handled and operated. Working lumen 22 may extend entirely through tubular member 12 and may be sized to provide access to distal end 20 for various surgical tools or therapies once distal end 20 of assembly 10 is positioned within a hollow body organ, and in particular may be useful to place an endoscope or other visualization tool. Alternatively, a fiberscope or other type of visualization tool may be integrated within the elongate member. Examples of useful scopes may be the Olympus GIF P140, the Fujinon EG 25PE, and the like. Gastroplasty device 24 is typically positioned at the distal end of tubular member 12 and is also generally configured to be advanced atraumatically through the body of a patient and within a hollow body organ, e.g., esophagus, stomach, etc. Alternatively, an optional separate thin walled oversheath, may also be placed over the acquisition device, including the elongate member, to assist in placement, or may be placed over a guidewire or obturator down the esophagus prior to placement of the gastroplasty device and removed with the gastroplasty device once the procedure is complete. The liner may be made of a thin wall polymer such as polyolefin, polytetrafluoroethylene (PTFE), expanded PTFE (ePTFE), silicone and the like, having a wall thickness between 0.004" and 0.025". This liner can serve to guide the gastroplasty device, as well as help to limit trauma to the esophagus and other delicate structures.

Figure 1B:
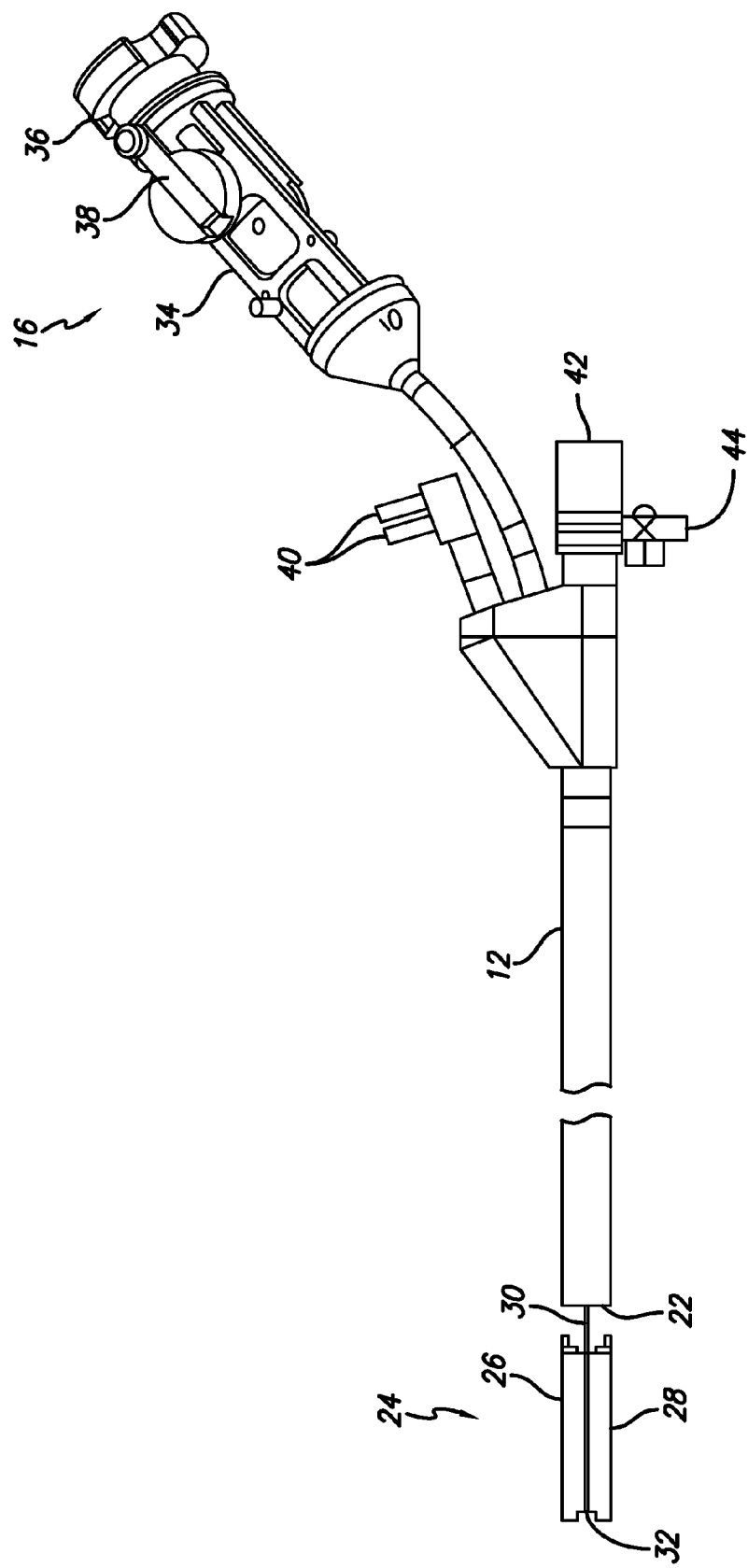

FIG. 1B shows a closer detail view of the gastroplasty assembly 10. As shown there, the device comprises a distal working portion, which comprises a cartridge member or pod 26 placed longitudinally in apposition to anvil member or pod 28. As described above, when the device is in use, the tissue of the stomach wall (including, in some instances, the muscular tissue layers) are adjusted or tensioned around the perimeter of the distal working portion, and within the distal working portion inner volume, to achieve a desired resulting geometry (e.g., small gastric pouch or restrictive partition or baffle). Thus, the gastric volume may be predetermined by adjusting the volume of the distal working portion, inner or outer profile. Cartridge member 26 may contain one or several fasteners, e.g., staples, clips, etc., which may be actuated via controls located proximally on handle assembly 16. A septum or barrier 32, described in further detail below, may be removably positioned between cartridge member 26 and anvil member 28 while connection member 30 may connect device 24 to tubular member 12.

Handle assembly 16 may be variously configured depending upon the desired functionality to be implemented on assembly 10. In this variation, handle assembly 16 may generally comprise handle 34 for use by the surgeon or physician in advancing, withdrawing, or articulating assembly 10. A control for articulating the device 24 between an open and closed configuration may be located on handle 34, shown as clamping control knob 36, while a separate control mechanism, shown here as fastener firing lever 38, may be utilized for deploying the fasteners located within cartridge member 28. Although specific types of controls are shown, these are intended only to be illustrative of the types of control mechanisms which may be utilized and are not intended to be limiting in scope.

Assembly 10 may further have one or several integrated vacuum ports 40 proximally located on elongate member 12 for fluid connection to one or several vacuum pumps (not shown). One or each of cartridge 26 or anvil 28 members may be fluidly connected through a common tube or channel or through individually corresponding tubes or channels through elongate member 12 to vacuum ports 40. Additionally, a scope seal housing 42 configured to provide access to the working lumen 22 may also be optionally provided near or at the proximal end of elongate member 12 for the insertion of various tools and devices through elongate member 12 for accessing the distal end of the assembly 10. An optional auxiliary port 44 may also be provided for allowing fluid communication via a channel or tubing through elongate member 12 between the proximal and distal ends of the assembly 10. Auxiliary port 44 may be utilized for various purposes, e.g., delivery of fluids or gases into the hollow body organ for transporting drugs or providing insufflation, etc. As noted above, the elongate body may be comprised of a series of links, similar to those described in U.S. patent application Ser. No. 10/686,326, or of an extrusion fabricated with various lumens to accommodate the various control wire and mechanisms of the acquisition device. Similarly, the control mechanisms may be grouped together with a flexible band, and then sheathed in a thin skin sheath, such as heat shrink. The elongate member may also be a combination of an extrusion and a thin wall sheath to allow for flexibility, and may utilize braided materials, e.g., stainless steel or superelastic materials such as Nickel-Titanium alloy, integrated in the wall of the sheath to prevent kinking and enhance torqueability.

Figure 2A:
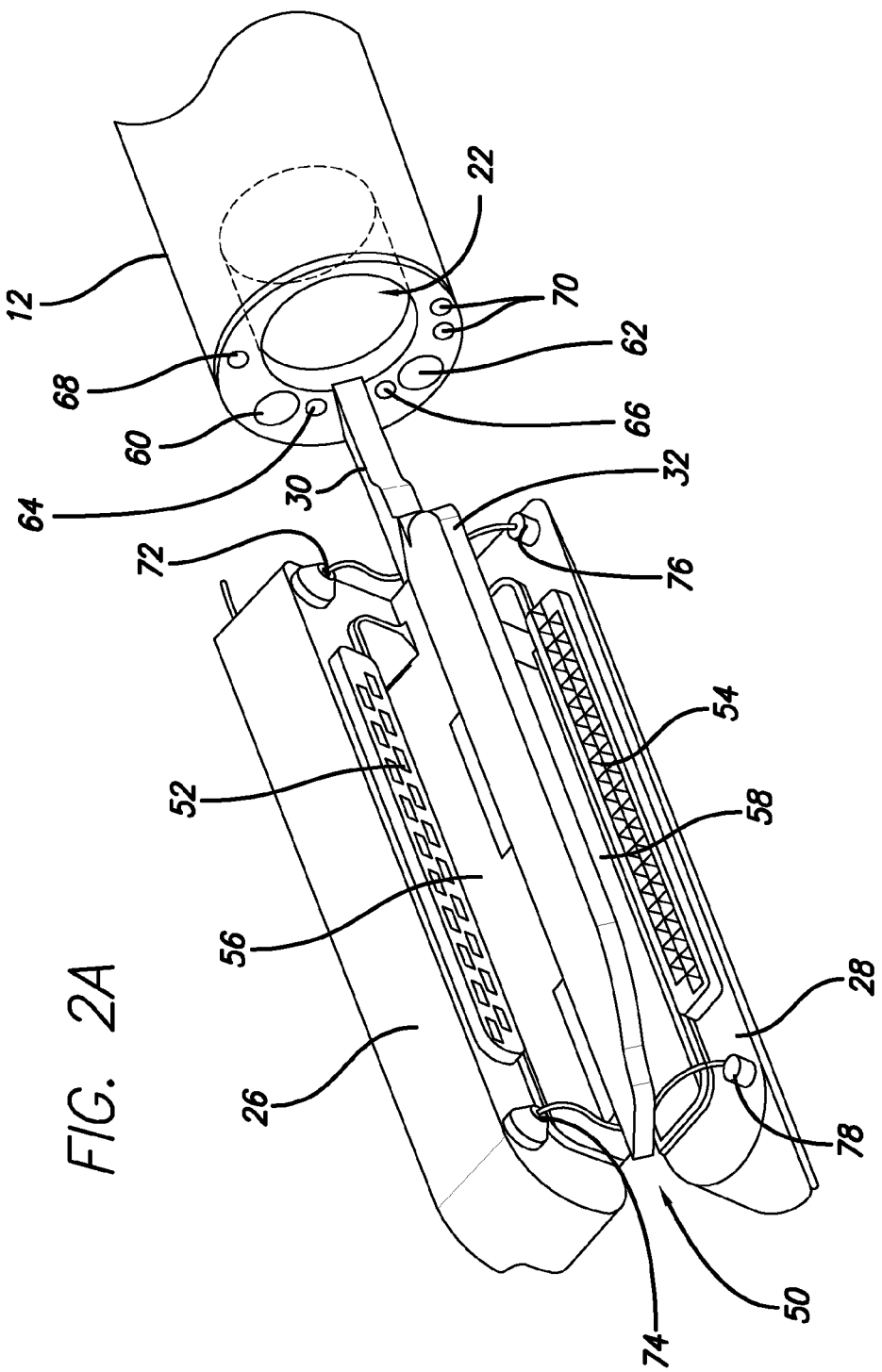
FIGS. 2A and 2B show perspective detailed views of an exemplary gastroplasty device described herein.

A detailed view of one variation of the gastroplasty devices described herein is shown in the perspective view of FIG. 2A. The cartridge member 26 and anvil member 28, as described above, may extend longitudinally from the distal end of elongate member 12 via connection member 30. The cartridge member 26 and anvil member 28 may be both or singularly articulatable relative to one another or relative to elongate member 12. A pivot 50 longitudinally positioned between cartridge member 26 and anvil member 28 may be configured to enable the device to be pivoted into an open configuration for the acquisition of tissue and a closed or deployment configuration for delivery or advancement of the device into the hollow body organ.

If both members 26, 28 are articulatable, they may be configured to be either simultaneously or sequentially articulatable. The cartridge member 26 may contain a cartridge 52 container fasteners along an outer edge of the member 26 while the anvil member 28 may have an anvil positioned along an outer edge of the member 26 such that the anvil corresponds to the number and position of fasteners within cartridge 52. One or both members 26, 28 may also define openings 56, 58, respectively, along a portion of the length or the entire length of each of the members 26, 28. One or both of these openings 56, 58 may be connected via tubing through vacuum lumens 60, 62, respectively, defined through elongate member 12 to the vacuum ports 40 located at the proximal end of member 12. Alternatively, a central vacuum lumen may supply both ports, or may bifurcate at the proximal or distal end of member 12. Elongate member 12 may also define various cable lumens 64, 66 for the passage of cables for controlling the opening and closing of members 26, 28 as well as additional cable lumen 68 for the passage of cables for actuating deployment of the fasteners from within cartridge 52. Moreover, cable lumen 70 may be used for the passage of cables used for controlling the clamping of the members 26, 28 towards one another.

Figure 2B:
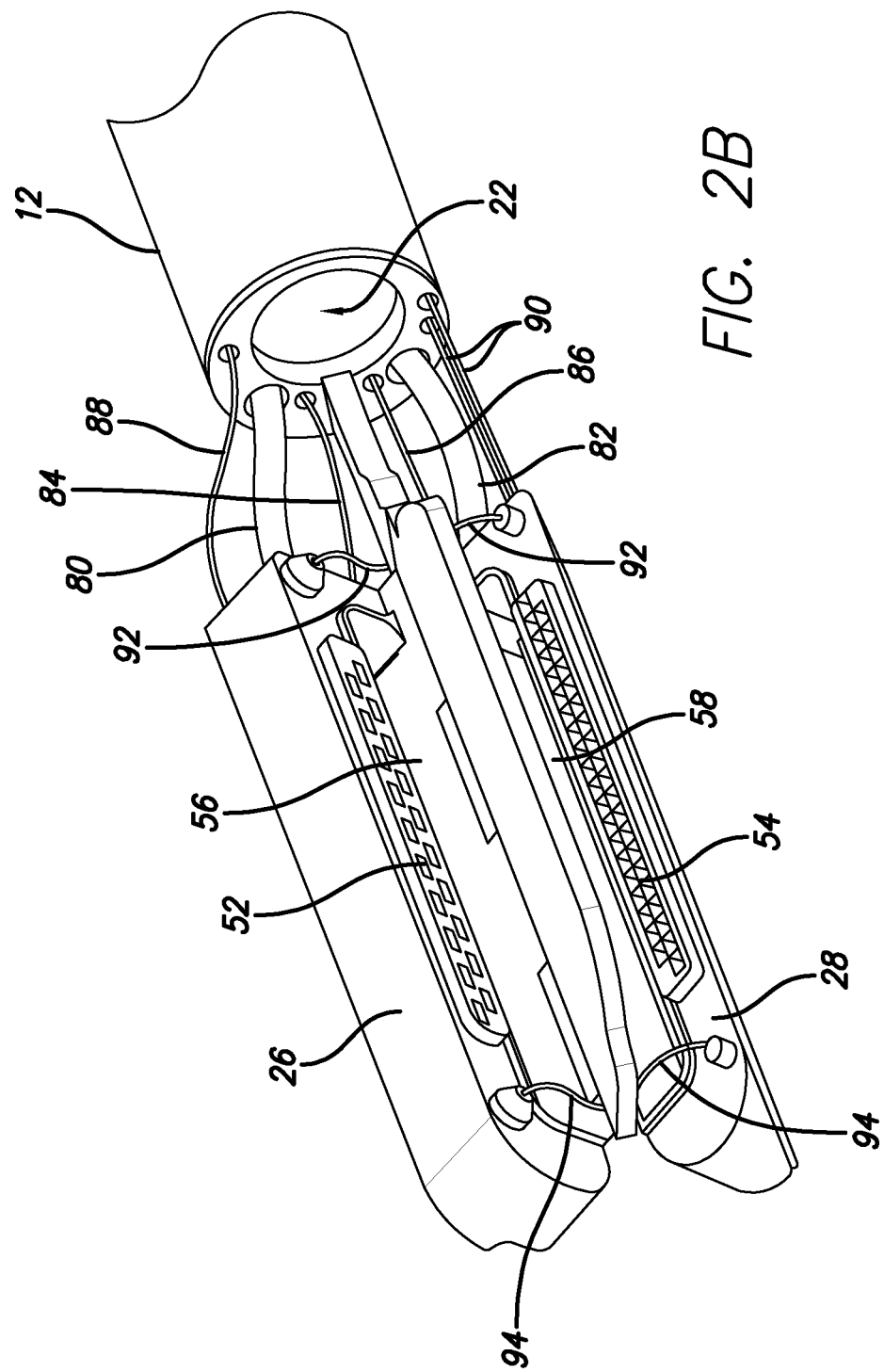

Each of the members 26, 28 may have openings 72, 74 and 76, 78, respectively, defined at the outer corners of each member opposite pivot 50 to allow for the routing and passage of clamping cables through the device for enabling cartridge member 26 and anvil member 28 to be clamped closed towards one another. FIG. 2B shows a perspective view of the acquisition and fixation device of FIG. 2A with the vacuum tubing and cables routed through the device. As shown, vacuum tubing 80, 82 may be routed through elongate member 12 into a proximal end of one or each of cartridge member 26 and/or anvil member 28 for fluid connection with respective openings 56, 58. Cables 84, 86 may be utilized for opening and closing the cartridge member 26 and anvil member 28 and cable 88, which may be routed into cartridge member 26, may be positioned and utilized, e.g., for pulling or pushing a wedge mechanism, to deploy fasteners out of cartridge 52. Moreover, clamping cables 90 may be passed through elongate member 12 and routed through cartridge member 26 and anvil member 28 such that cables 92, 94 are passed through openings 72, 74 and 76, 78 for clamping cartridge member 26 and anvil member 28 closed. Cables 84 and 86 may be replaced by torque shafts connected to handles at the proximal end of the device, to open and close the cartridge and anvil members.

Figure 3A:
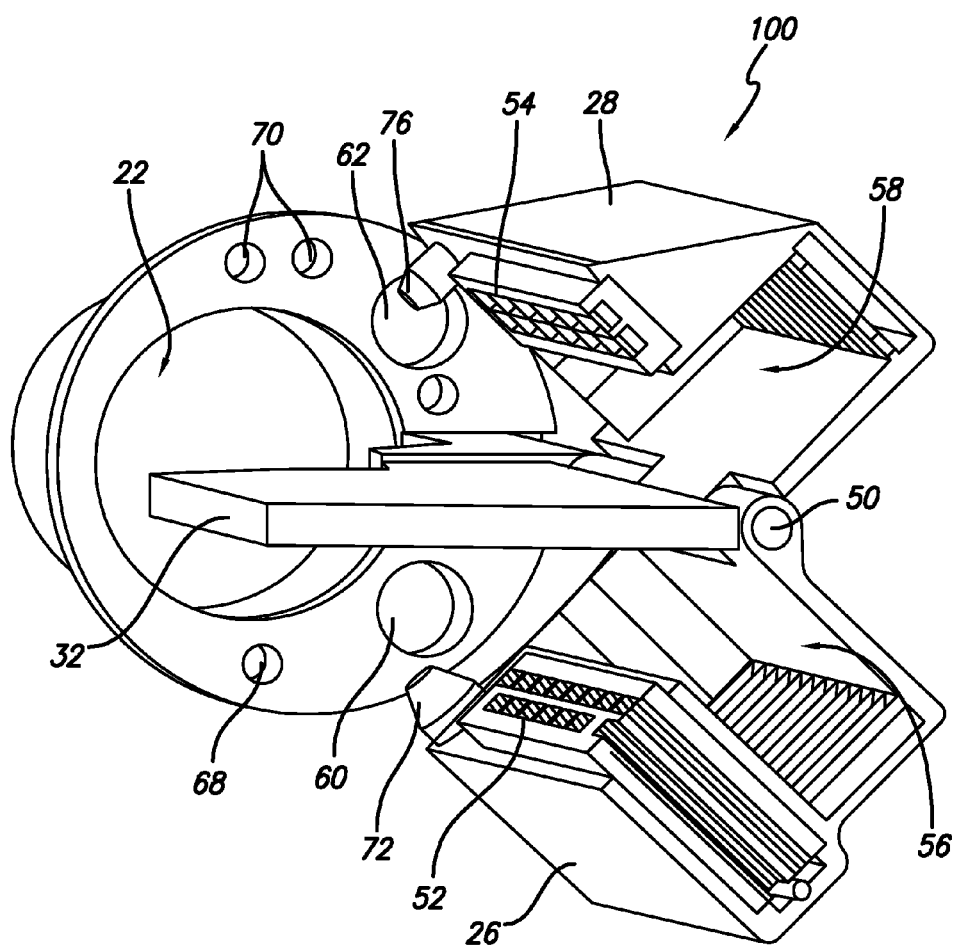
FIGS. 3A and 3B show perspective and end views, respectively, of a cross-sectioned portion of an exemplary gastroplasty device.
Figure 3B:
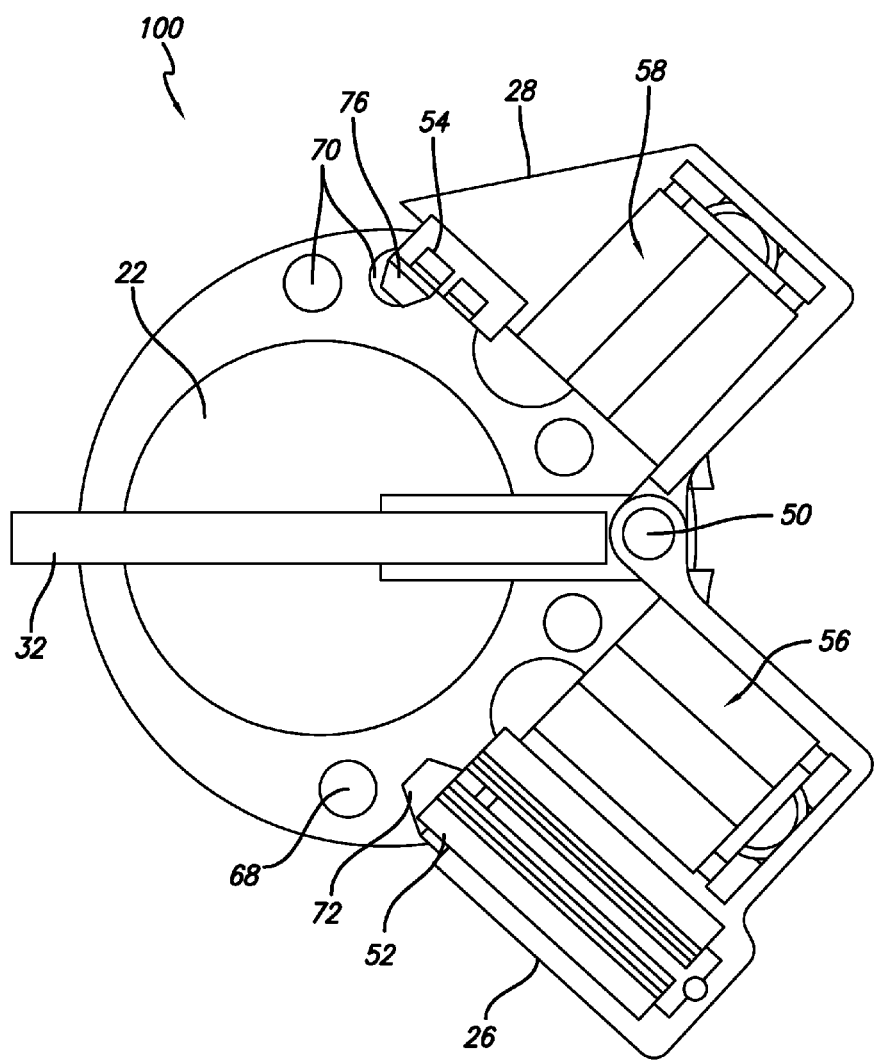

FIGS. 3A and 3B show perspective and end views, respectively, of a cross-sectioned portion 100 of a suitable gastroplasty device. As may be seen, septum 32 may be positioned to extend from pivot 50 effectively separating vacuum openings 56, 58 within cartridge member 26 and anvil member 28, respectively. Adjacent to opening 56 is fastener cartridge 52 and adjacent to opening 58 is anvil 54 positioned such that when septum 32 is removed or displaced, the articulation of cartridge member 26 and anvil member 28 towards one another about pivot 50 positions cartridge 52 in apposition to anvil 54. Alternatively, anvil member 28 cartridge member 26 may be non-movable or in a fixed position relative to the longitudinal axis of the device. In this configuration, fastener cartridge 52 and optionally anvil 54, may be actuated to eject from their respective housings to fasten the acquired tissue.

Figure 4A:
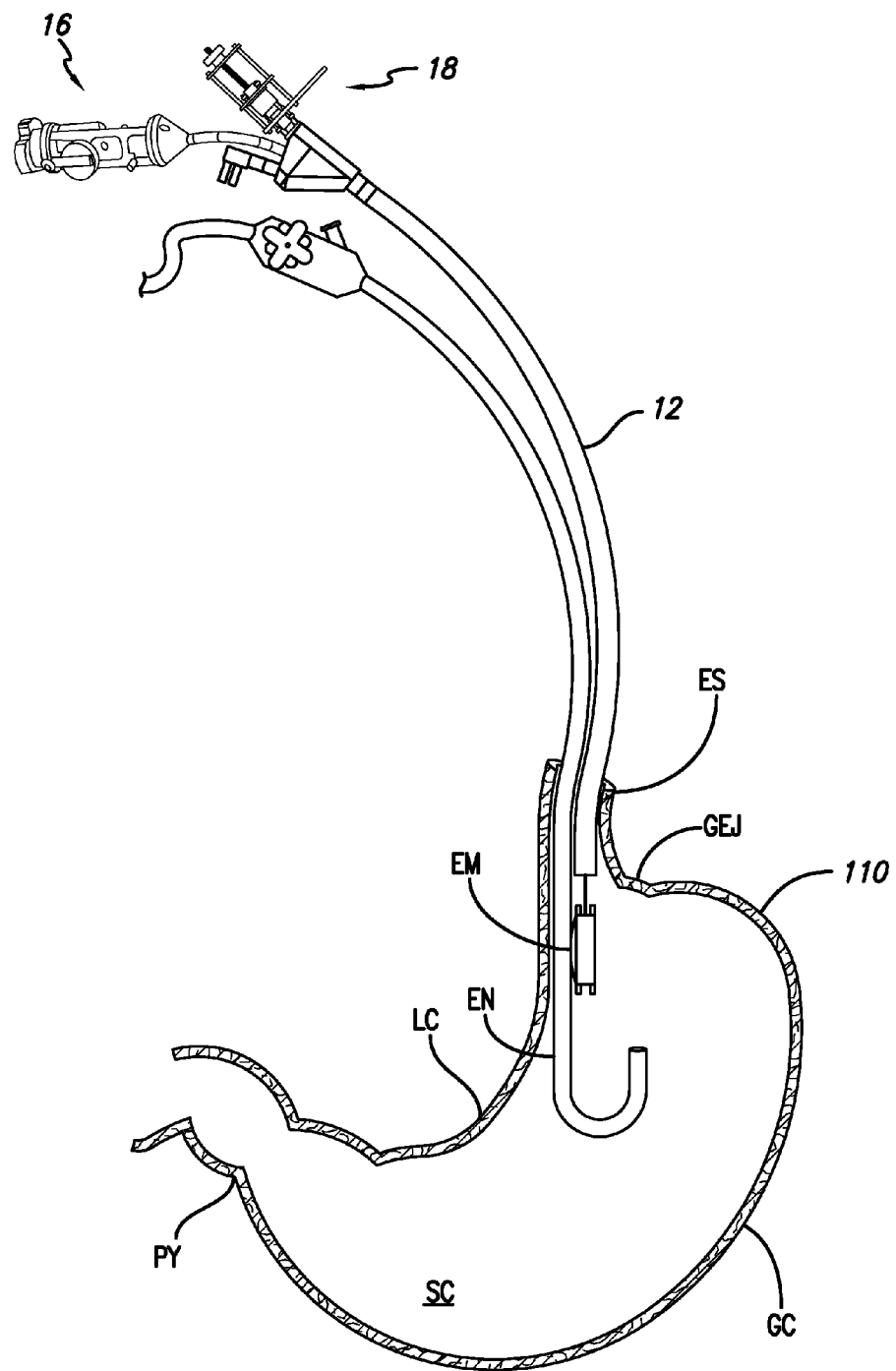
FIGS. 4A and 4B show representative illustrations of how a gastroplasty device may be advanced transorally through the esophagus of a patient and positioned within the stomach cavity of a stomach.
Figure 4B:
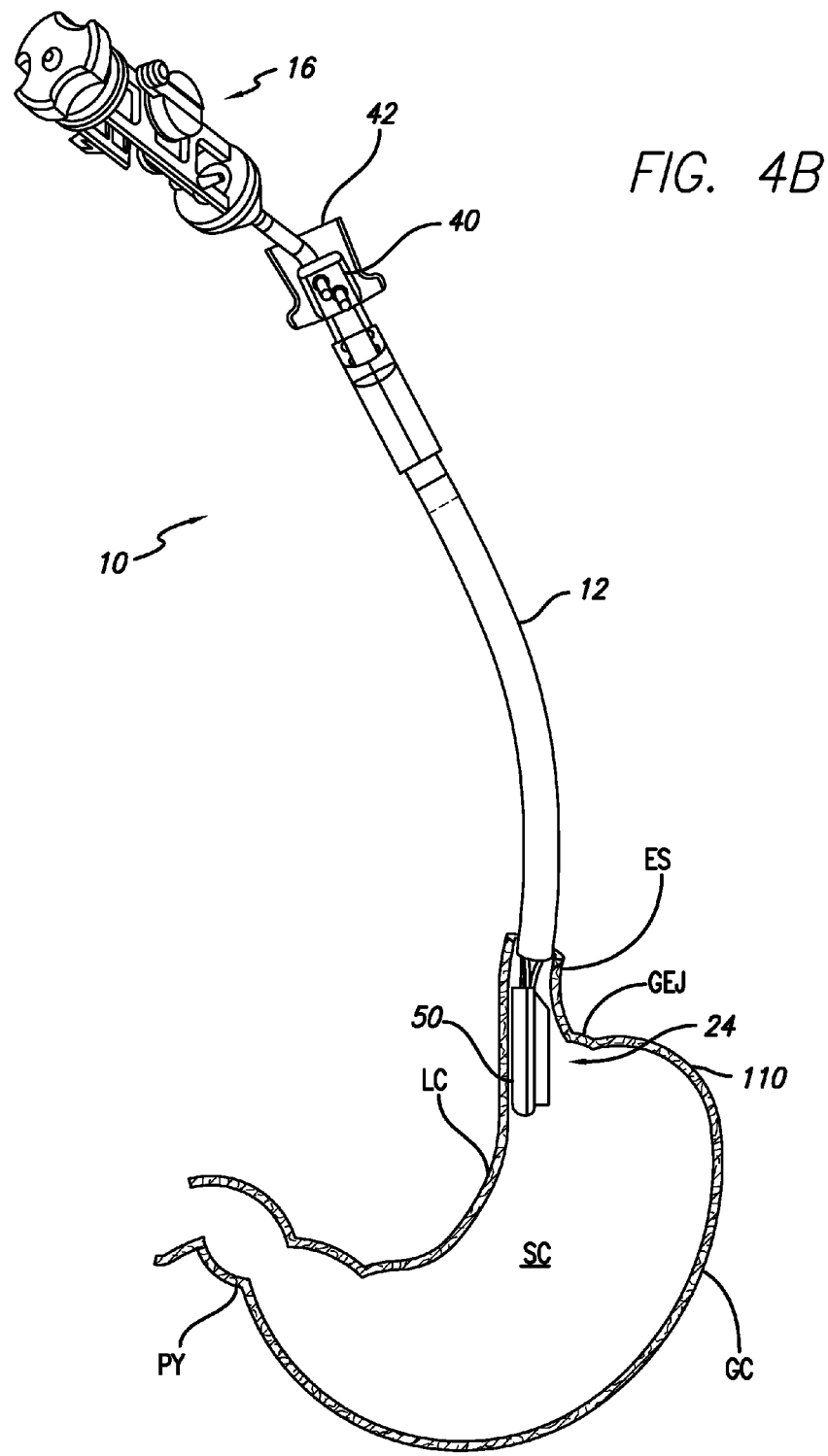

FIGS. 4A and 4B show representative illustrations of how gastroplasty device 24 may be advanced transorally through the esophagus ES of a patient and positioned within stomach cavity SC of stomach 110. Making reference now to FIG. 4A, device 24 may be articulated outside the patient via handle 16 so that the proximal portion of elongate member 12 may be positioned such that the spine of the device is placed against a portion of lesser curvature LC and opposite greater curvature GC. In this way, the device 24 extends between the gastroesophageal junction GEJ towards pylorus PY. In addition FIG. 4A depicts the use of a flexible endoscope EN alongside the device 10 to allow direct visualization of the procedure, including the fixation step whereby the scope can then be removed, leaving additional volume remaining in the smaller gastric pouch that may be helpful when removing or detaching the gastroplasty device 24 from the acquired tissue once it has been fixed. If no direct visualization is required, but additional removal volume is desired, an optional expandable balloon, or other expandable member EM may be used alongside the spine of the gastroplasty device, or may be integrated into the spine of the gastroplasty device using known techniques. FIG. 4B shows the positioning of gastroplasty device 10 without the aid of an endoscope, or other direct visualization technique.

Figure 5A:
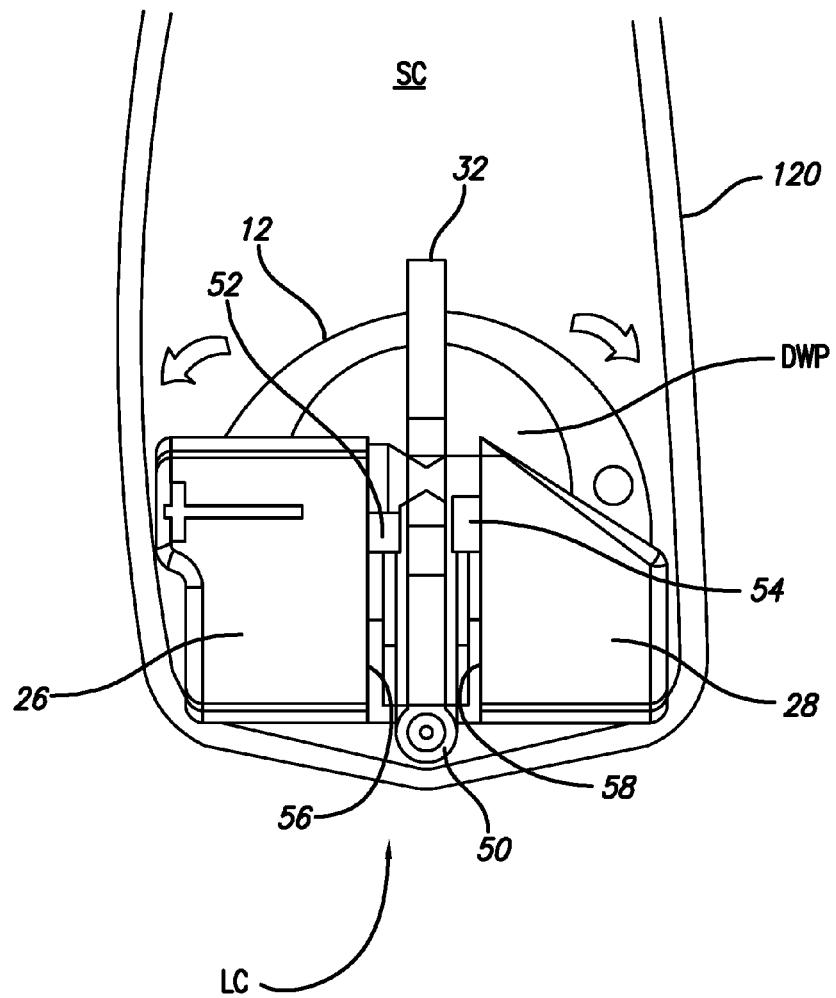
FIGS. 5A to 5D show end views of an example of how an exemplary gastroplasty device may be used to acquire and fasten tissue within a hollow body organ.
Figure 5B:
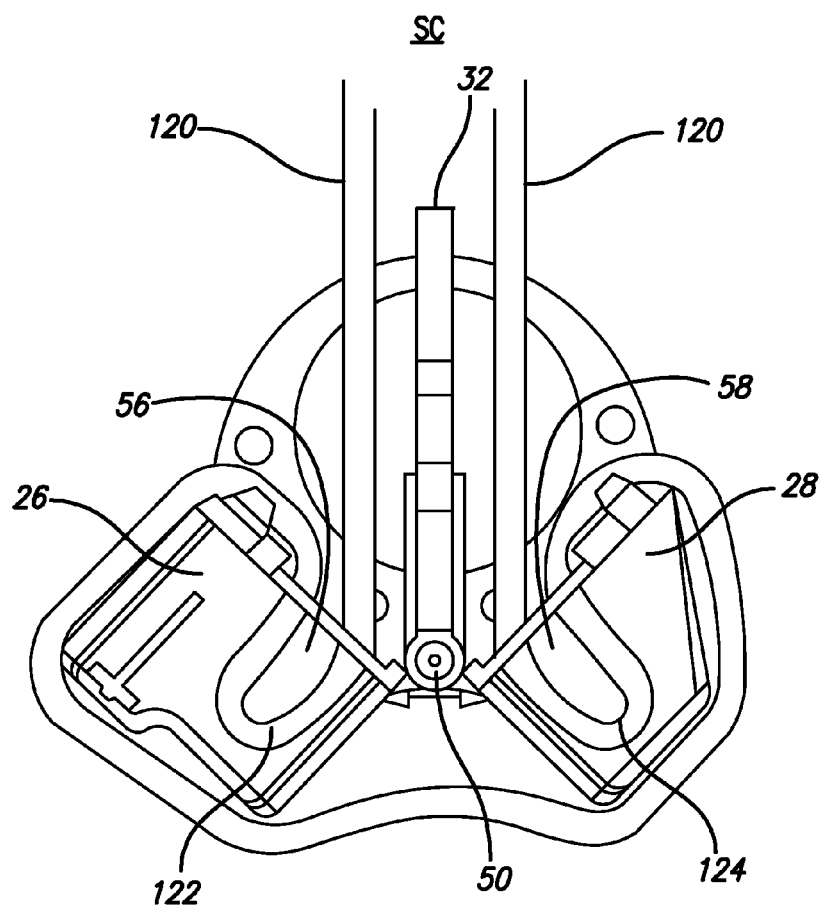

FIG. 5A shows an end view of device 24 positioned within stomach cavity SC with pivot 50 placed against stomach wall 120, for instance, against lesser curvature LC in one example of how the device 10 may be used to effect the creation of a gastric lumen or partition within stomach cavity SC. The device is advanced through the esophagus ES while in a deployment configuration, i.e., where the distal working portion of the device DWP is configured so that cartridge member 26 and anvil member 28 are closed such that openings 56, 58 and cartridge 52 and anvil 54 are directly positioned in apposition about septum 32. When desirably positioned, one or both of cartridge member 26 and anvil member 28 may be rotated about pivot 50 in the direction of the arrows shown. FIG. 5B shows cartridge member 26 and anvil member 28 rotated at an angle with a vacuum force activated within openings 56, 58. In certain embodiments where no pivoting or movement of the cartridge member 26 or anvil member 28 is necessary, the device is advanced in a static state. As seen, portions of the stomach wall 120 may be acquired and drawn within respective openings 56, 58. The configuration of cartridge member 26 and anvil member 28 and the positioning of the device 24 within stomach cavity SC are such that this tissue acquisition procedure also enables the device 24 to be self-adjusting with respect to the acquired tissue 122, 124. More particularly, the device 24 is configured such that portions of the stomach wall 120 are automatically positioned for fixation upon being acquired and the device 24 becomes automatically adjusted within stomach cavity SC relative to the stomach wall 120. Furthermore, because of the manner in which the tissue is acquired, the tissue intimately surrounds the cartridge member 26 and anvil member 28, i.e., the distal working portion of the device DWP, by being tensioned or held around the perimeter PT of the distal working portion of the device and within the inner volume IV of the distal working portion of the device to define the subsequent volume or resulting geometry RG resulting gastric lumen as shown by the diagonal and hatched lines respectively in FIGS. 5F and 5G. An illustrative depiction of a cross section of a resulting tissue geometry is provided in FIG. 5E. Other depictions of resulting tissue geometries are provided in FIGS. 5H and 5I. Shown there are front views of the distal working portion of the device, and cross sectional views (along lines A-A and B-B respectively) of the resulting tissue geometries. In FIG. 5H, the distal working portion has been configured to provide one plication P, whereas in FIG. 5I, the distal working portion has been configured to provide more than one plication. Multiple plications may be useful, for example, to help increase the ease in which the distal working portion of the device is removed from a patient after tissue has been acquired and fixed. Thus, as these Figs. illustrate, the gastric volume may be predetermined by adjusting the volume of the cartridge member 26 and anvil member 28, or geometry of the distal working portion of the device, e.g., the distal working portion of the device may be configured so that the gastric tissue has results in the geometries described, for example, in U.S. patent application Ser. No. 10/417,790, which was filed on Apr. 16, 2003 and is hereby incorporated by reference in its entirety.

Figure 5C:
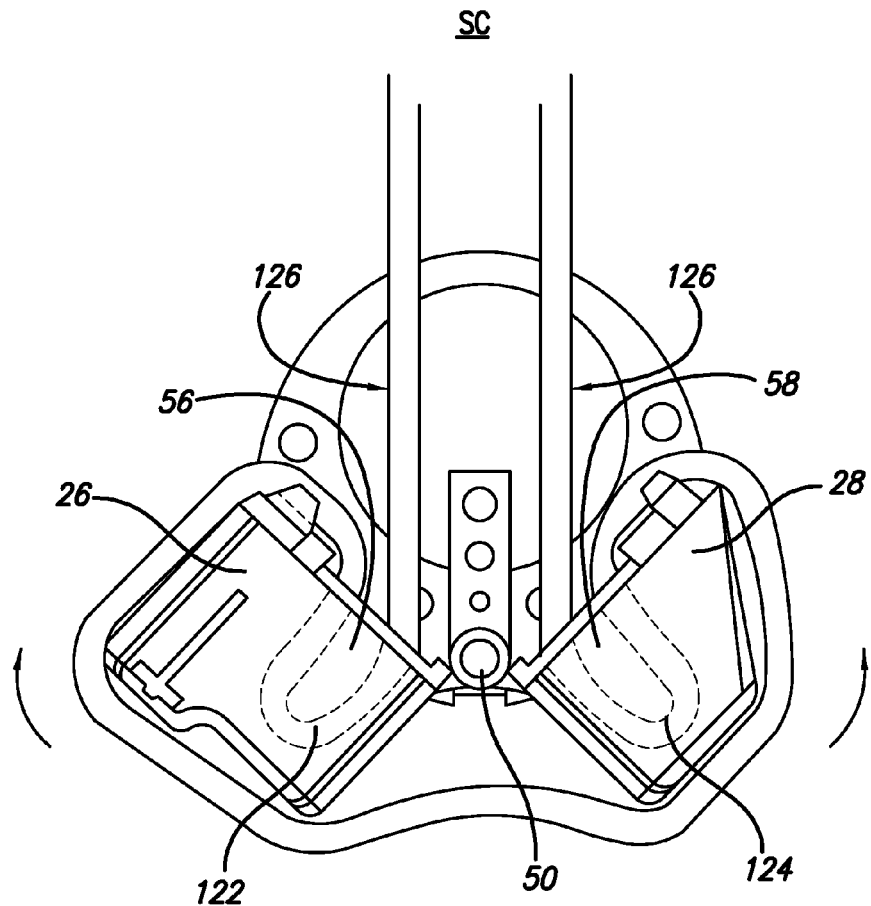

Optional septum 32 may act effectively as a barrier between openings 56, 58 to facilitate the acquisition of the tissue 122, 124 into their respective openings 56, 58 while minimizing or eliminating cross acquisition of the tissue into cartridge member 26 and/or anvil member 28. In another alternative, septum 32 may be omitted from the device 24 and acquisition of the tissue may be accomplished by sequentially activating vacuum forces within openings 56 and 58. That is, the cartridge and anvil members may be orient towards the tissue surface in a sequential fashion, acquiring the tissue adjacent thereto. However, when a septum is employed, it may be removed from between cartridge member 26 and anvil member 28 by translating the septum 32 distally, laterally, or proximally of cartridge member 26 and anvil member 28, after the tissue has been acquired. Alternatively, the septum may be left within stomach cavity SC for later removal, or as will be described in more detail below, may be left within the stomach cavity to biodegrade. FIG. 5C shows septum 32 having been removed so that cartridge member 26 and anvil member 28 may be pivoted from the open configuration back to its closed configuration in the direction of the arrows shown. Because the septum 32 has been removed, tissue region 126 may now be presented for clamping between cartridge 52 and anvil 54.

Figure 5D:
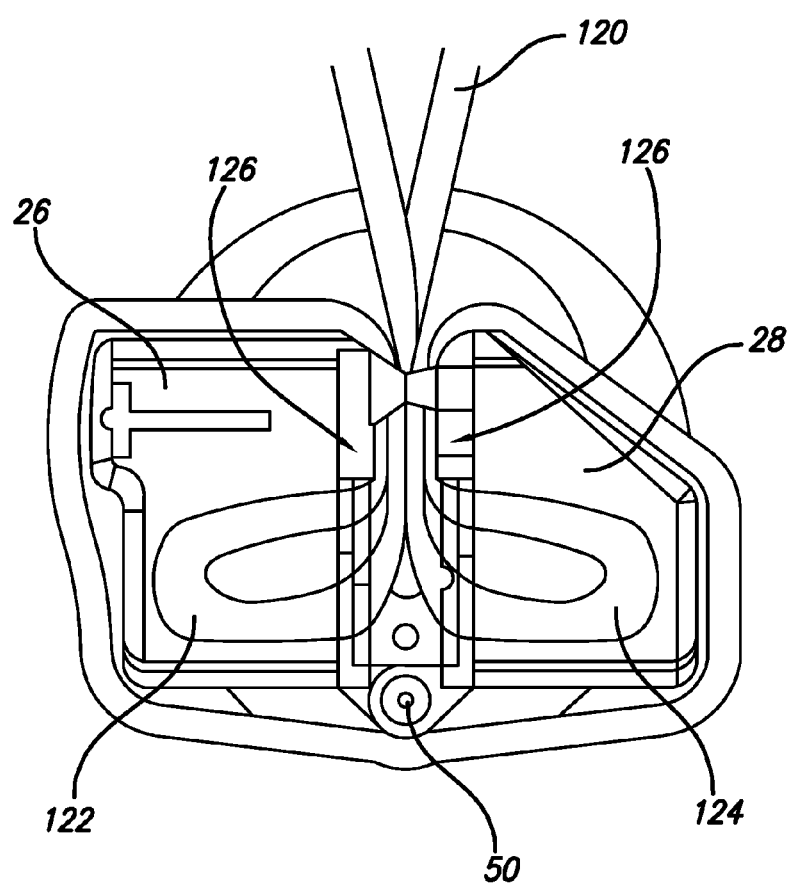
Figure 5E:
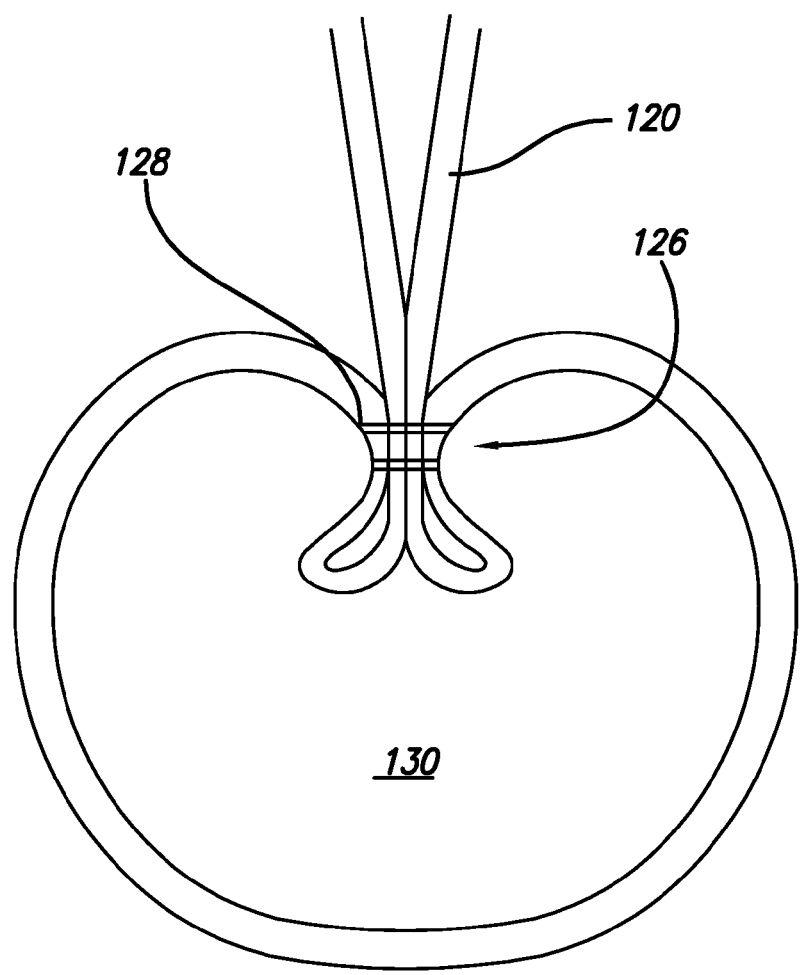
FIG. 5E illustrates a resulting fastened gastric lumen that may be formed using the gastroplasty devices described herein.
Figure 5F:
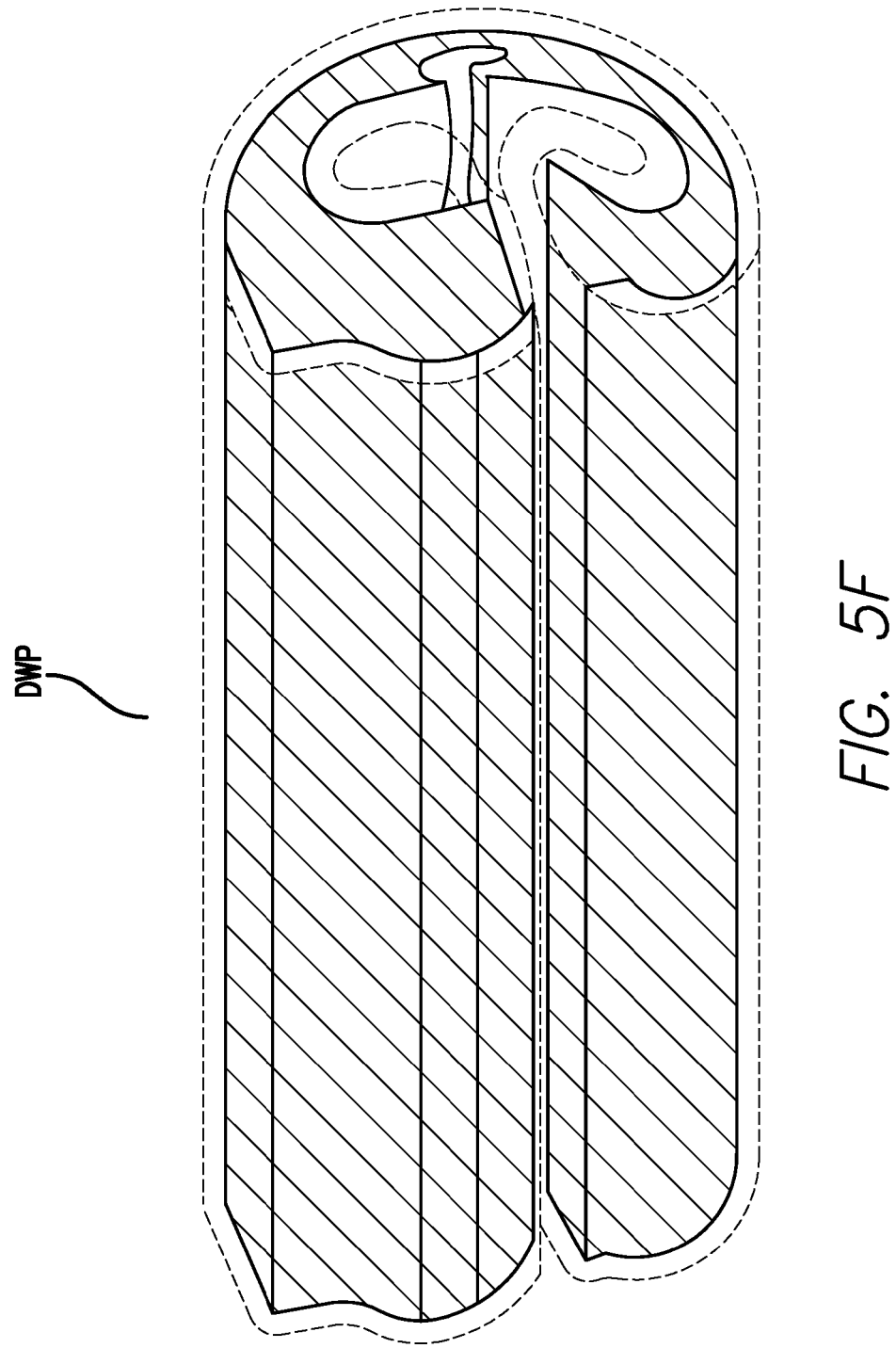
FIGS. 5F and 5G demonstrate how a distal working portion of a gastroplasty device, and an inner volume, respectively, help to define the final configuration of the acquired tissue.
Figure 5G:
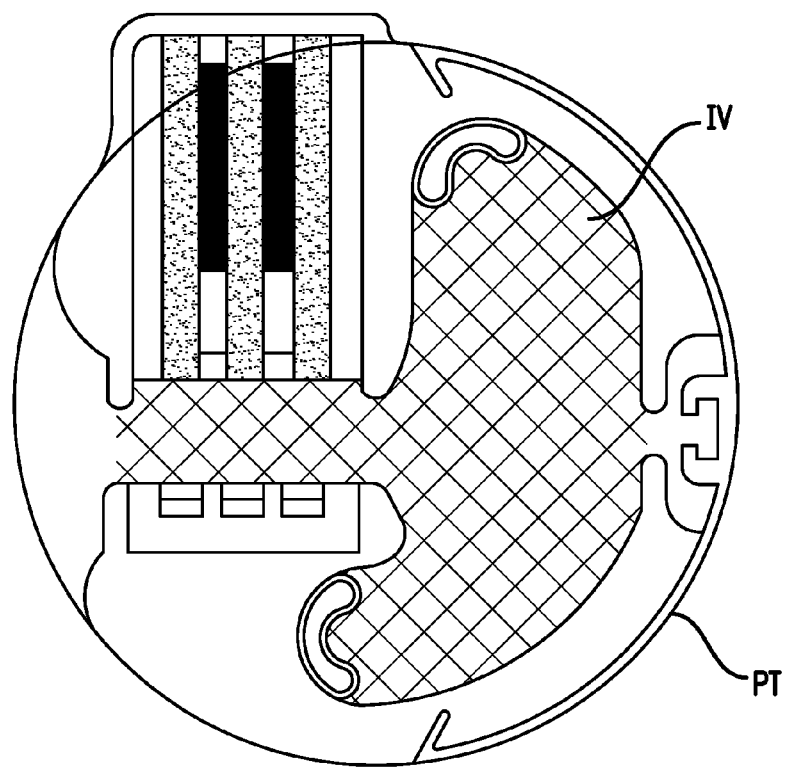

As shown in FIG. 5D, cartridge member 26 and anvil member 28 may be simply clamped over tissue region 126 and fastened by deploying one or several fasteners from within cartridge 52. In acquiring the tissue 122, 124, manipulation of the tissue region 126 or the acquired tissue 122, 124 may be eliminated entirely due to the automatic positioning of the tissue for fastening. Once the clamped tissue has been fastened, the device 24 may be withdrawn entirely from the stomach cavity SC, as shown in FIG. 5E. As seen, one or several fasteners 128, e.g., a line of staples, may hold the tissue in its fastened configuration to result in the creation of a partition, creating a restriction, or when desired, creating a gastric lumen or pouch 130, separate from the remainder of the stomach cavity.

Figure 6A:
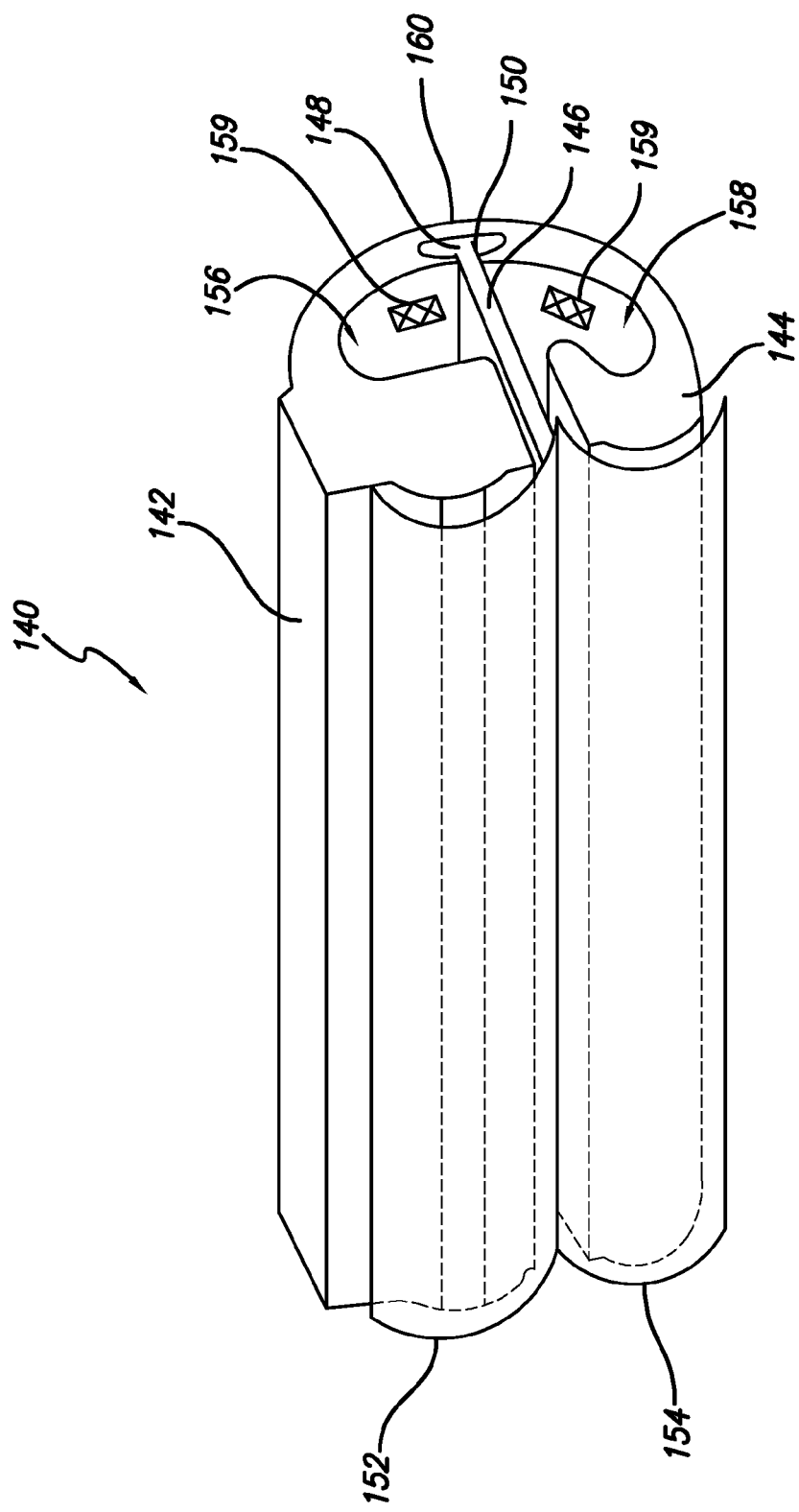
FIGS. 6A and 6B show perspective and end views, respectively, of one variation of a gastroplasty device, wherein the septum is in position.
Figure 6B:
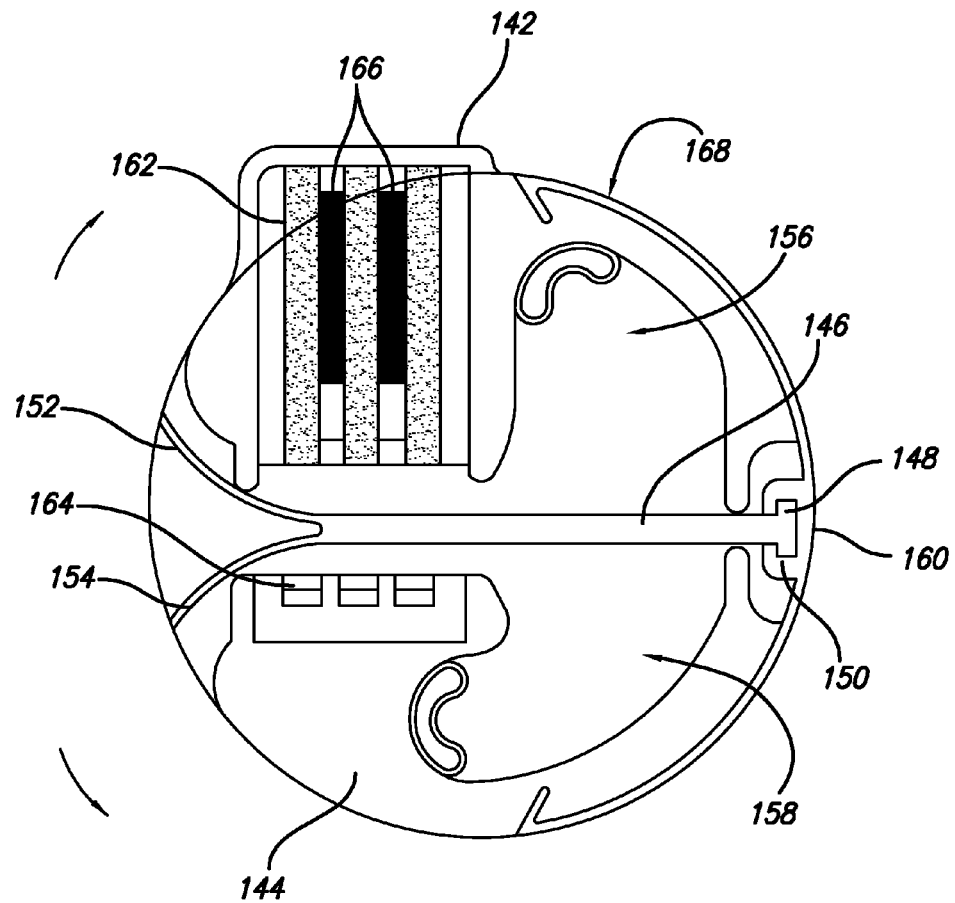

Alternative variations of gastroplasty device 24 may also be utilized. For instance, FIG. 6A shows a perspective view of another variation in device 140 partly cross-sectioned for the sake of clarity. In this variation, cartridge member 142 and anvil member 144 may define a curved or arcuate shape. The septum may also be configured to have a longitudinal barrier portion 146 with a first transverse barrier 152 and a second optional transverse barrier 154. One or both barriers 152, 154 may extend in a curved or arcuate shape from the longitudinal septum 146 such that an atraumatic surface is presented to tissue during advancement within the patient. The septum may be retained between cartridge member 142 and anvil member 144 via septum detent 148 being slidably positioned within septum retaining channel 150, which extends longitudinally between cartridge member 142 and anvil member 144. Longitudinal septum 146 may partition openings 156, 158, which may function in the same manner as described above for adhering tissue. It may be advantageous to house a pressure transducer 159 near or within the pod(s) or opening (s), to allow the device user to accurately gauge measurement of pressure at the site of tissue adhesion. A drop of pressure within the pod or opening signals to the user that the vacuum seal has been compromised, and therefore the amount of tissue adhered to the system is not optimal. Readings from the transducer can serve as feedback to the user that sufficient vacuum pressure has been maintained, and therefore be a "go-nogo" trigger to the user. FIG. 6B shows a cross-sectional end view of the variation 140 from FIG. 6A. As illustrated, cartridge 162 may retain one or several fasteners 166, shown in this variation as staples, in corresponding apposition to anvil 164 when cartridge member 142 and anvil member 144 are in the closed or delivery configuration. It should be noted that while a rectangular staple jaw is depicted, it may be desirable to provide a curved track or wedge to facilitate the placement of a curved line of staples, from the rectangular jaw. Pivoting member or plate 168, which may function to facilitate the pivoting the device, may be seen as placed over the outer surface of cartridge member 142 and anvil member 144.

Figure 7A:
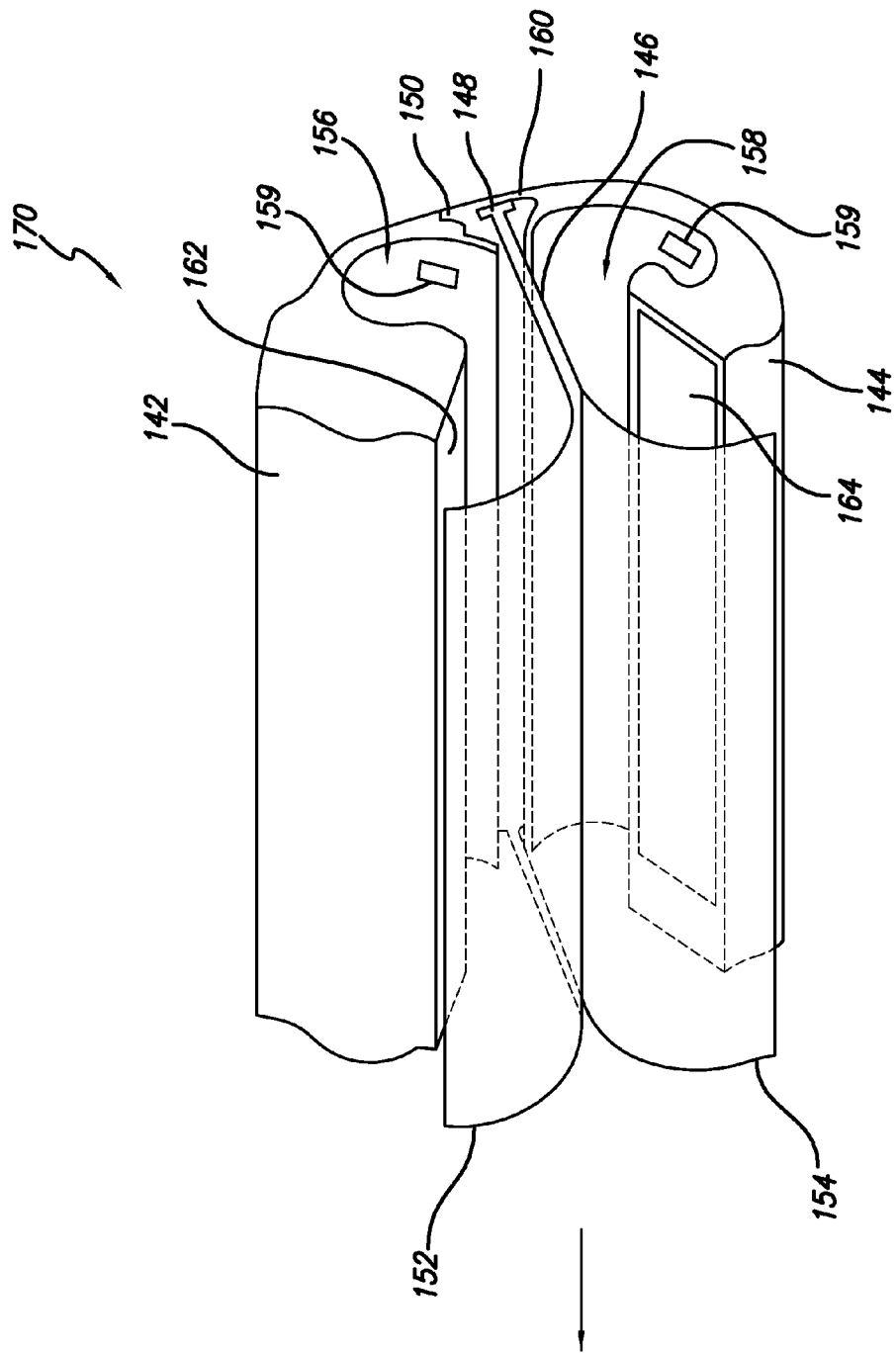
FIGS. 7A and 7B show perspective and end views, respectively, of the device of FIG. 6A in an open configuration.
Figure 7B:
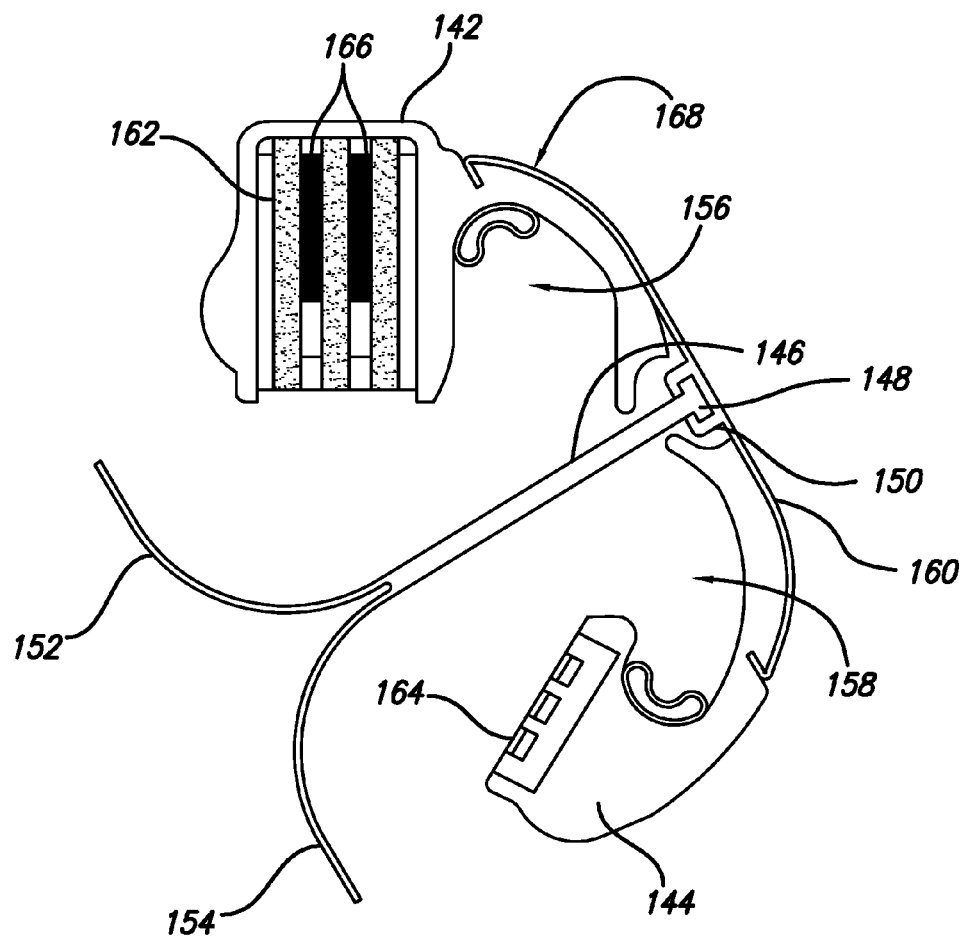
Figure 8A:
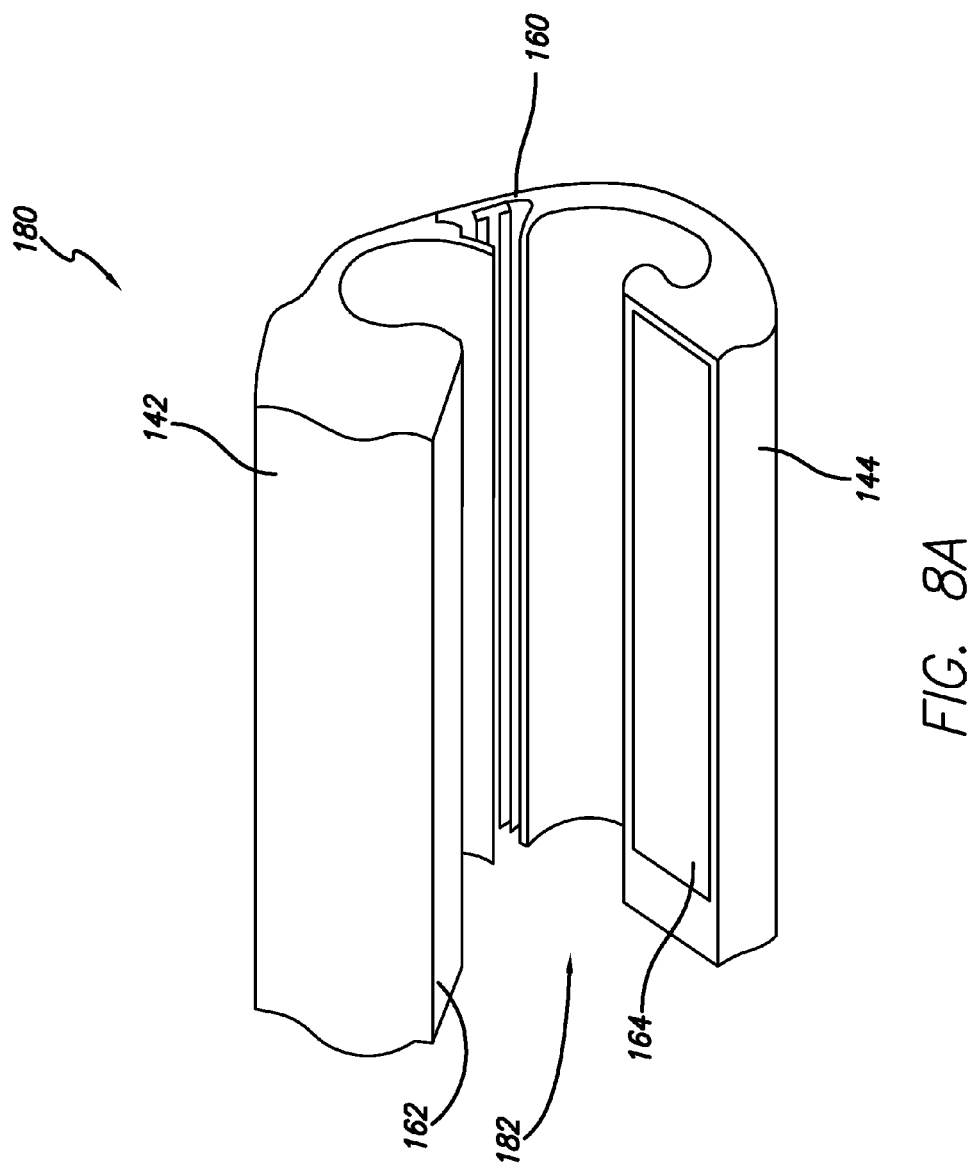
FIGS. 8A and 8B show perspective and end views, respectively, of the device of FIG. 6A in an open configuration with the septum removed.
Figure 8B:
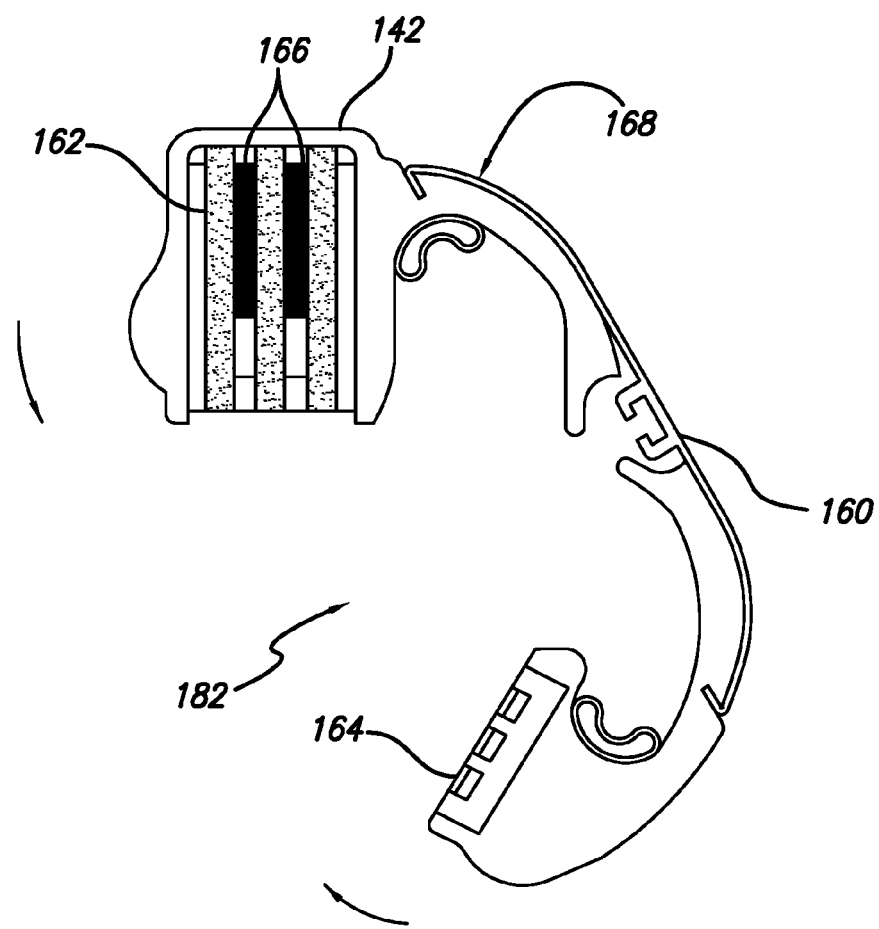
Figure 9A:
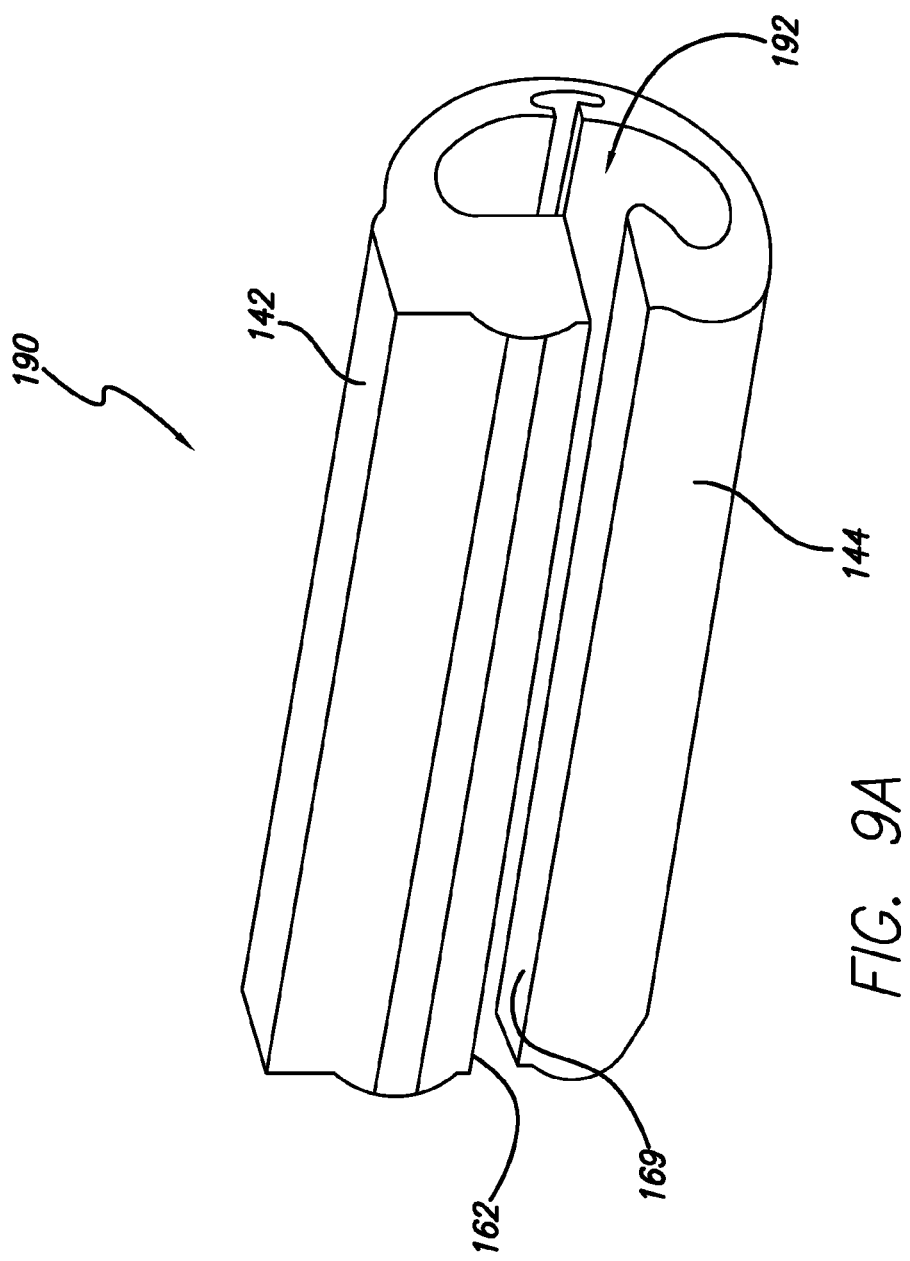
FIGS. 9A and 9B show perspective and end views, respectively, of the device of FIG. 6A in a closed configuration.
Figure 9B:
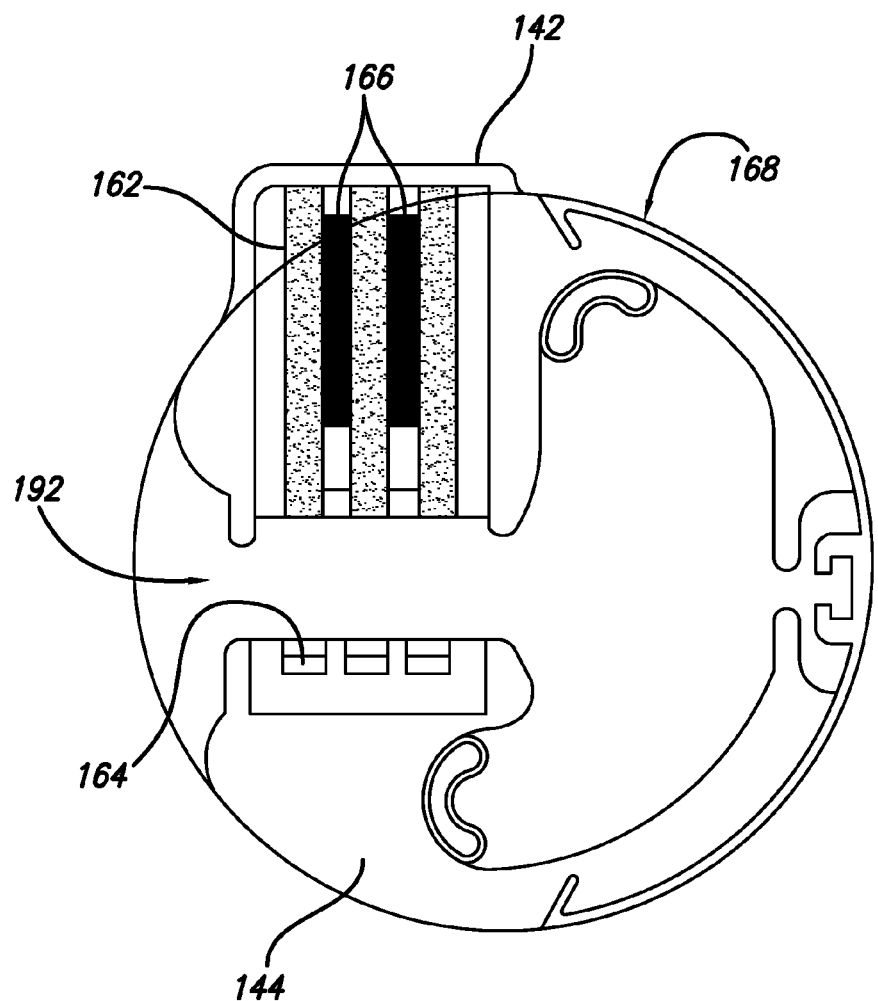

FIG. 7A shows a perspective view of an open configuration 170 of the device of FIGS. 6A and 6B for receiving tissue within openings 156, 158. Septum 146 may be removed from the device by translating the septum 146 longitudinally in the direction of the arrow. As shown in the end view in FIG. 7B, pivoting region 160 may be seen expanded via pivoting plate 168, which may be made from various biocompatible materials, e.g., stainless steel, polymers, etc., and which is sufficiently flexible to enable the device to transition between the open and closed configurations. FIG. 8A shows the open configuration 180 in which the septum 146 has been removed from the device. As described above, the septum may be removed once the tissue has been acquired within their respective openings. FIG. 8B shows an end view of the device with the septum removed. The tissue acquired within open region 182 may be clamped by articulating cartridge member 142 and anvil member 144 in the direction of the arrows to result in the configuration shown in FIG. 9A, which shows the device 190 ready for fastening the clamped tissue within clamping region 192. FIG. 9B shows an end view of the device configured into its closed configuration for fastening the tissue within clamping region 192. As described above, because the stomach tissue may be automatically configured for fastening once the tissue has been acquired, manipulation of the tissue is rendered unnecessary during clamping and fastening of the tissue.

Figure 10A:
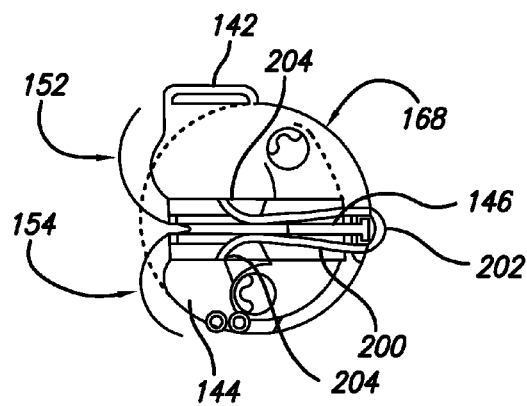
FIGS. 10A to 10C show end views of the cartridge member and anvil member during delivery, during tissue acquisition, and prior to clamping of the tissue, respectively, in one example of how a clamping cable may be routed with respect to an optional septum.
Figure 10B:
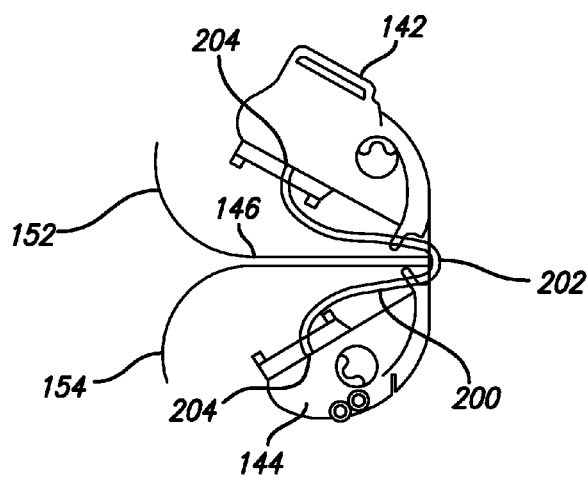
Figure 10C:
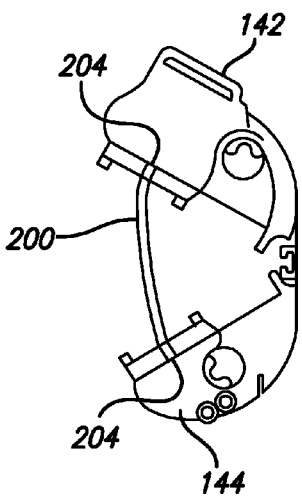

In facilitating the clamping of cartridge member 142 and anvil member 144 onto the tissue, clamping cables may be utilized, as described above. FIGS. 10A to 10C show end views of cartridge member 142 and anvil member 144 during delivery, during tissue acquisition, and prior to clamping of the tissue, respectively, and one example of how clamping cable 200 may be routed with respect to septum 146. FIG. 10A shows septum 146 in position between cartridge member 142 and anvil member 144 with clamping cable 200 routed within a cable constraining slot 202 defined in an adjacent portion of septum 146. The clamping cable 200 may extend between cartridge member 142 and anvil member 144 through clamping cable openings 204 defined in both cartridge member 142 and anvil member 144. Once the septum 146 is removed, as shown in FIG. 10C, the clamping cable 200 may be released from slot 202 and tensioned to bring cartridge member 142 and anvil member 144 towards one another, as described in further detail below. Other mechanisms of clamping are also suitable, for example, the tissue may be clamped using hydraulic, pneumatic, or electropneumatic mechanisms, all of which are well known in the art.

FIGS. 11A and 11B shows perspective and end view of another alternative gastroplasty device 210. This variation shows cartridge member 212 and anvil member 214 in a closed configuration with extension member 218 connected to longitudinal pivot 216. The septum, in this variation, may comprise a longitudinal septum member 220 and a perpendicularly positioned transverse septum member 222, which may extend partially over the openings 228, 230 when cartridge member 212 and anvil member 214 are in an open configuration, as shown in FIG. 11C. Respective vacuum tubing 224, 226 may be fluidly connected to one or both openings 228, 230 defined within their respective members 212, 214. FIG. 11D illustrates the device with the septum translated distally showing a clearer view of opening 230.

Figure 12A:
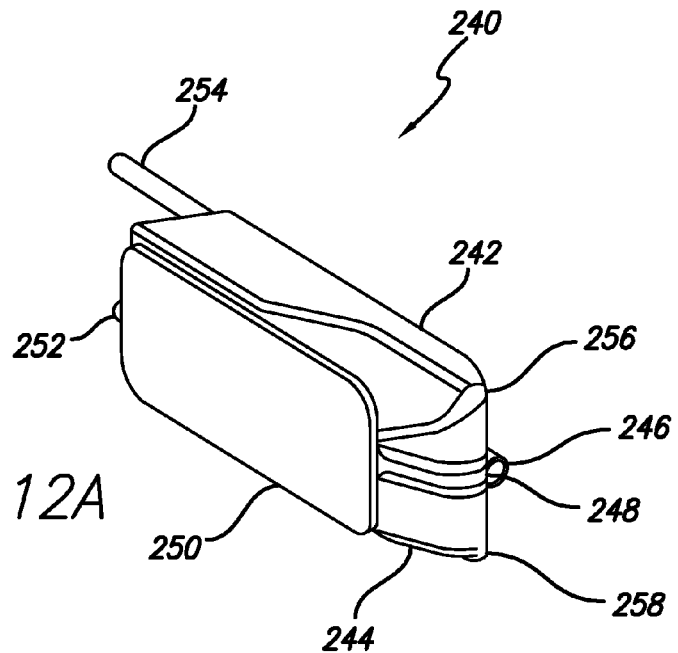
FIGS. 12A to 12C show perspective views of yet another variation of a gastroplasty device.
Figures 12B, 12C:
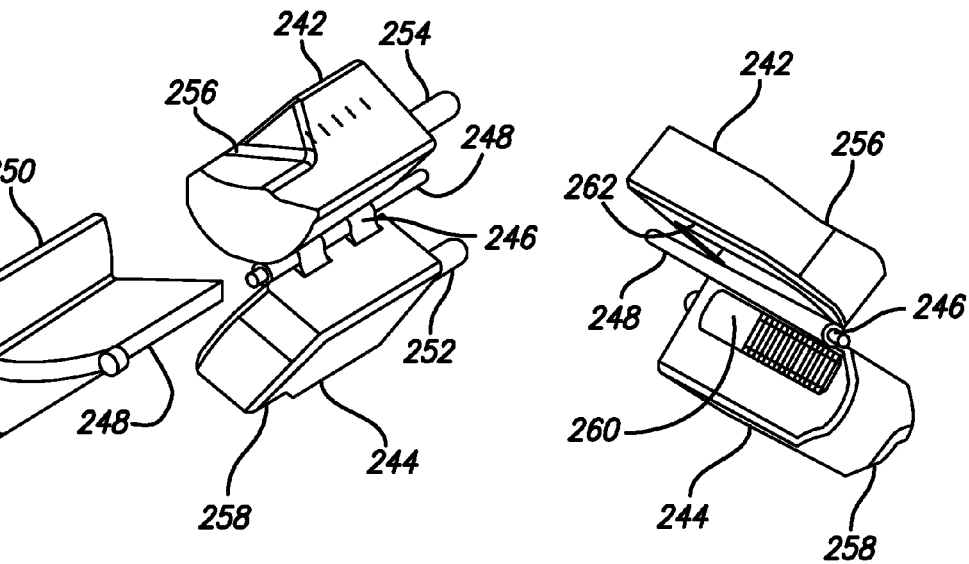

FIGS. 12A to 12C show perspective views of yet another variation of gastroplasty device 240. In this variation, cartridge member 242 and anvil member 244 may be pivotally connected via longitudinally defined pivot 246. Similar to the variation of FIGS. 11A and 11B, the septum may also comprise a longitudinal septum member 248 positionable between members 242, 244 and an optional perpendicularly configured transverse septum member 250. Also seen are vacuum tubing 252, 254 fluidly coupled to their respective openings 260, 262. As discussed above, because the resulting gastric lumen may be defined by the shape and volume of the device, cartridge member 242 and anvil member 244 may each define tapered distal ends 256, 258, respectively, to provide an atraumatic surface for advancement within the patient and to facilitate formation of a gastric lumen having a tapered distal region. The proximal shoulder of the members may also be tapered to facilitate removal of the device once the procedure has been completed. Moreover, this variation also shows openings 260, 262 which may be elongated to extend over a majority of the length of their respective members 244, 242.

Figure 13A:
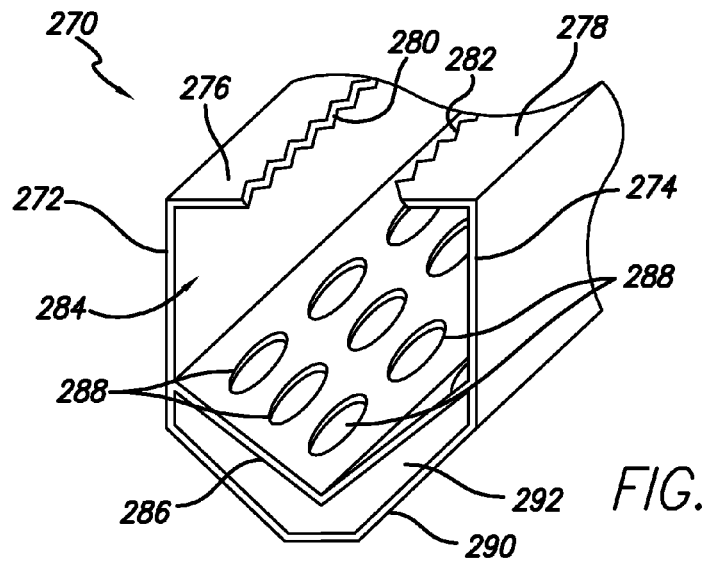
FIGS. 13A and 13B show cross-sectioned perspective and end views, respectively, of alternative acquisition pod assembly.

Yet another variation of an alternative acquisition pod assembly 270 is shown in the cross-sectioned perspective view of FIG. 13A. This variation may generally comprise pod walls 272, 274 each defining an undercut section 276, 278 having projections or serrations 280, 282 along their edges directed or angled towards one another. The assembly 270 may be comprised of a biocompatible material, e.g., polymers, polycarbonates, etc., which has an elastic bending modulus sufficiently low to allow for plastic deformation of the pod assembly 270 to occur. A barrier 286 having a plurality of openings 288 defined over its surface may be positioned between pod walls 272, 274 such that tissue acquisition chamber 284 is defined as shown. A vacuum chamber 290 may be located beneath barrier 286 with vacuum plenum 292 defined by chamber 290 and barrier 286.

Figure 13B:
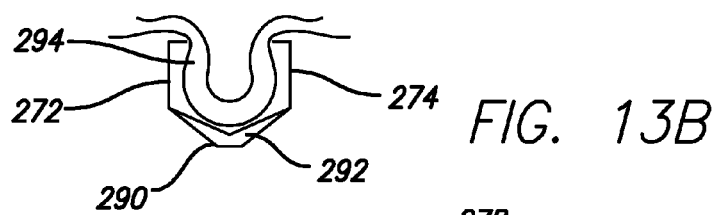
Figure 13C:
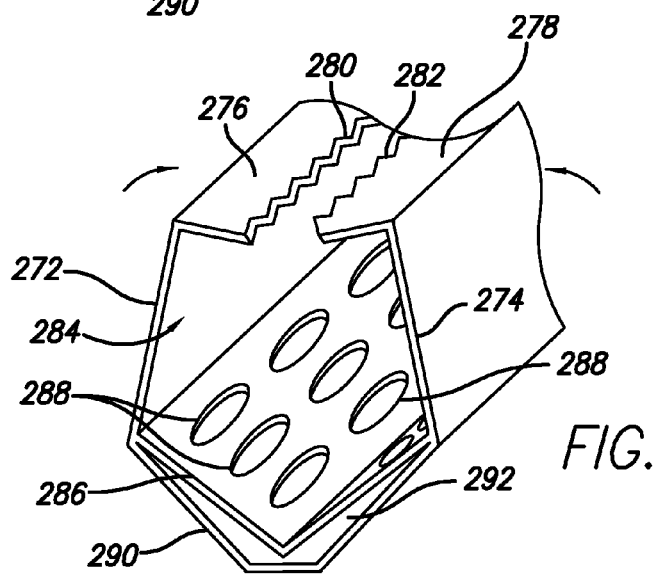
FIGS. 13C and 13D show cross-sectioned perspective and end views, respectively, of the device of FIGS. 13A and 13B under a high vacuum pressure.
Figure 13D:
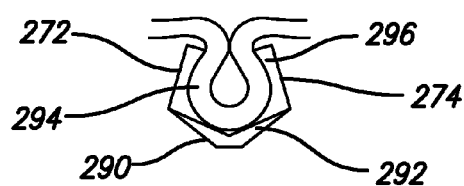

In operation, as shown in FIG. 13B, tissue 294 may be acquired against or within acquisition chamber 284 by the application of a relatively low pressure vacuum force applied through plenum 292, which may create a low vacuum within chamber 284 through openings 288. Once the tissue 294 has been first acquired, a higher pressure vacuum force may be applied through plenum 292 such that pod walls 272, 274 and undercut sections 276, 278, respectively, are plastically deformed and drawn towards one another in the direction of the arrows, as shown in FIG. 13C. As the undercut sections 276, 278 are drawn inwards and shown in FIG. 13D, the acquired tissue 294 may become pinched at retained tissue region 296 resulting in a temporary mechanical fixation of the tissue. A cessation of the high vacuum force may then result in a relaxation of the pod walls 272, 274 and ultimately of the release of the acquired tissue 294 when the vacuum force is ceased altogether. Spearing mechanisms or a plurality of sharp hooks may also be used, in conjunction with, or in lieu of, the undercut sections described above.

Figure 14A:
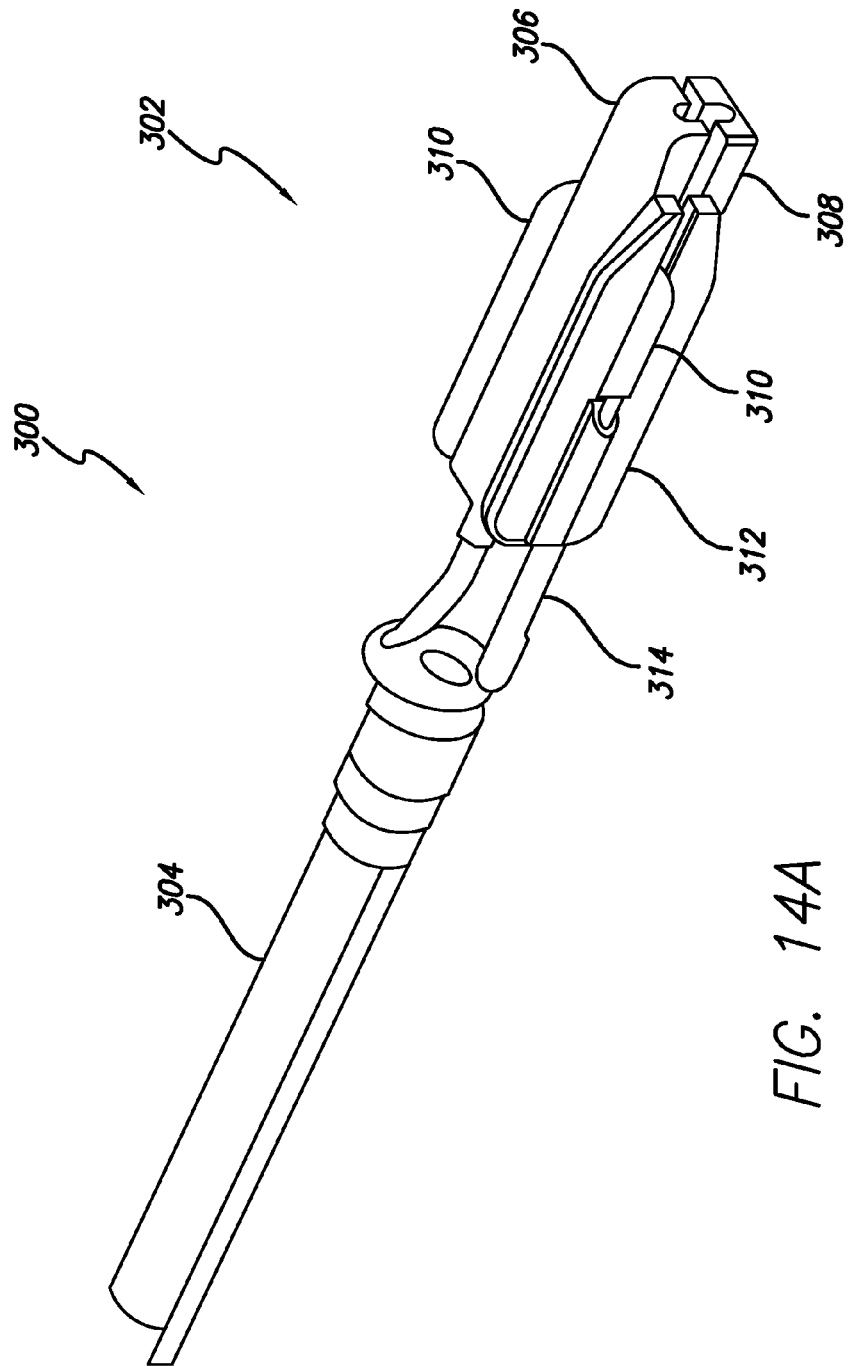
FIGS. 14A to 14D show perspective views of the operation of another variation of a gastroplasty device utilizing parallel pod motion.

Yet another variation of a gastroplasty device 300 is shown in the perspective views of FIGS. 14A to 14D. This particular variation may utilize a parallel translational motion in moving the cartridge member 306 and anvil member 308 between the open and closed configuration rather than a pivoting motion, as described above in other variations. As shown in FIG. 14A, device 300 may comprise pod assembly 302 connected at the distal end of elongate tubular member 304. Septum 310 may be removably positioned between cartridge member 306 and anvil member 308. A groove plate 312 defining a longitudinally extending slot may be positioned adjacent to cartridge member 306 and anvil member 308 on a side opposite to that of septum 310.

Figure 14B:
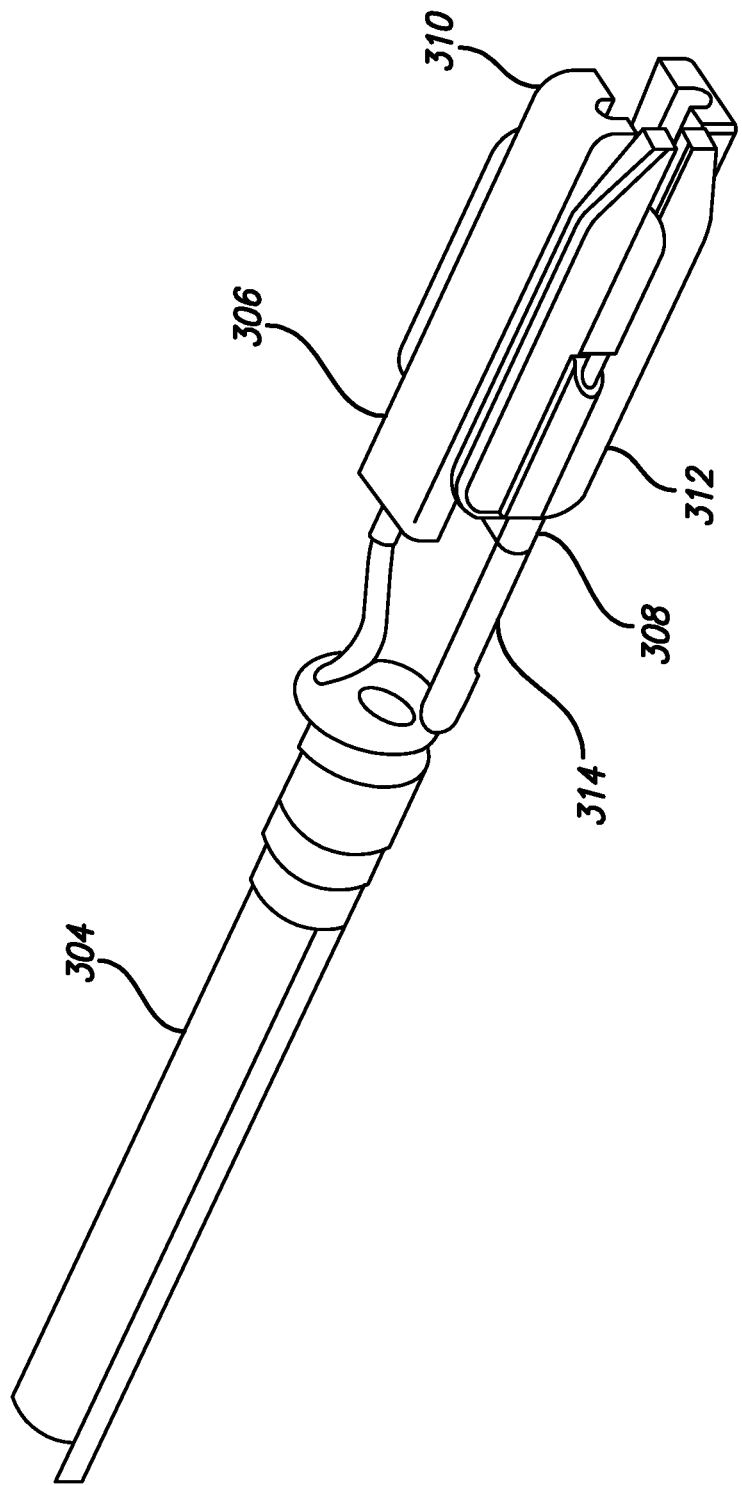
Figure 14C:
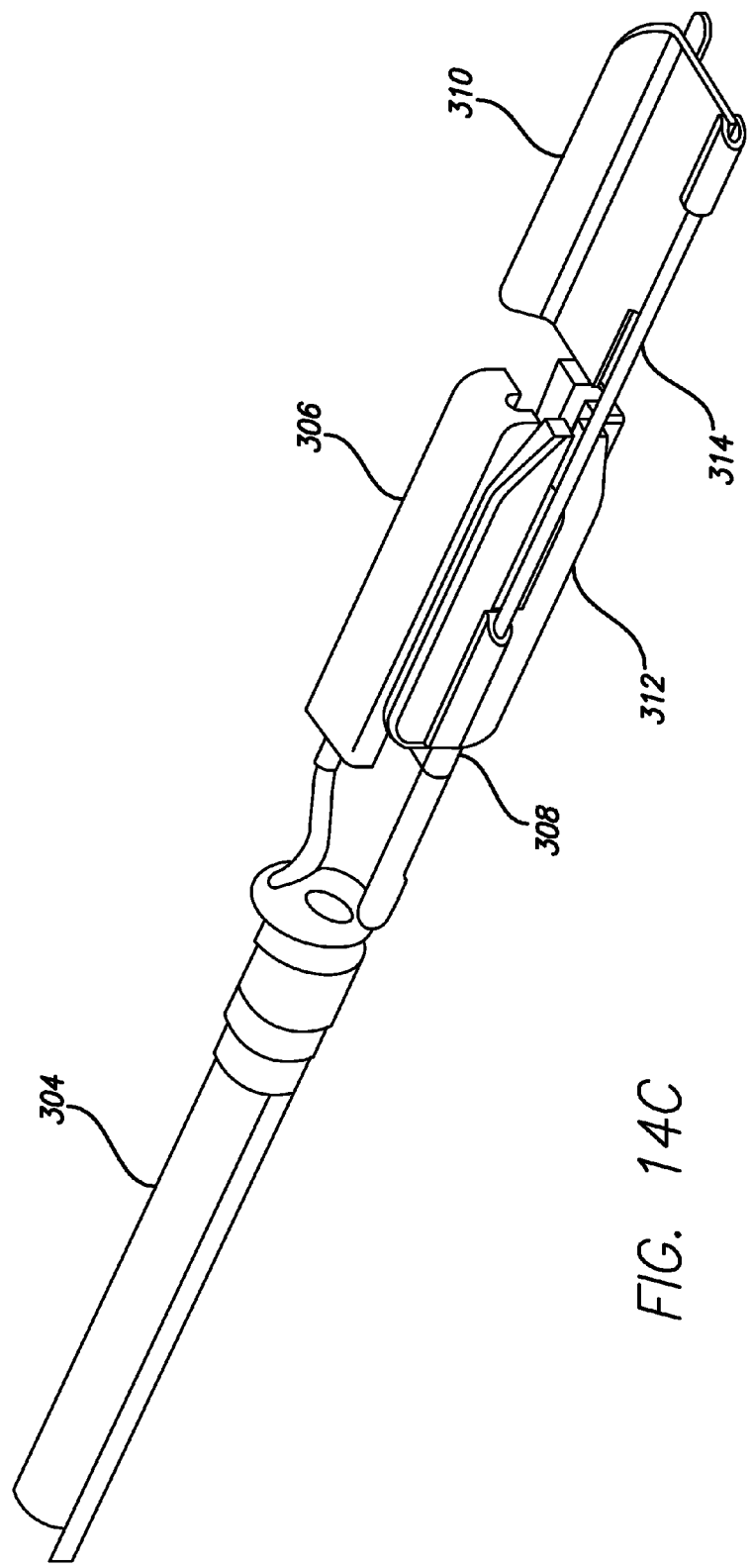
Figure 14D:
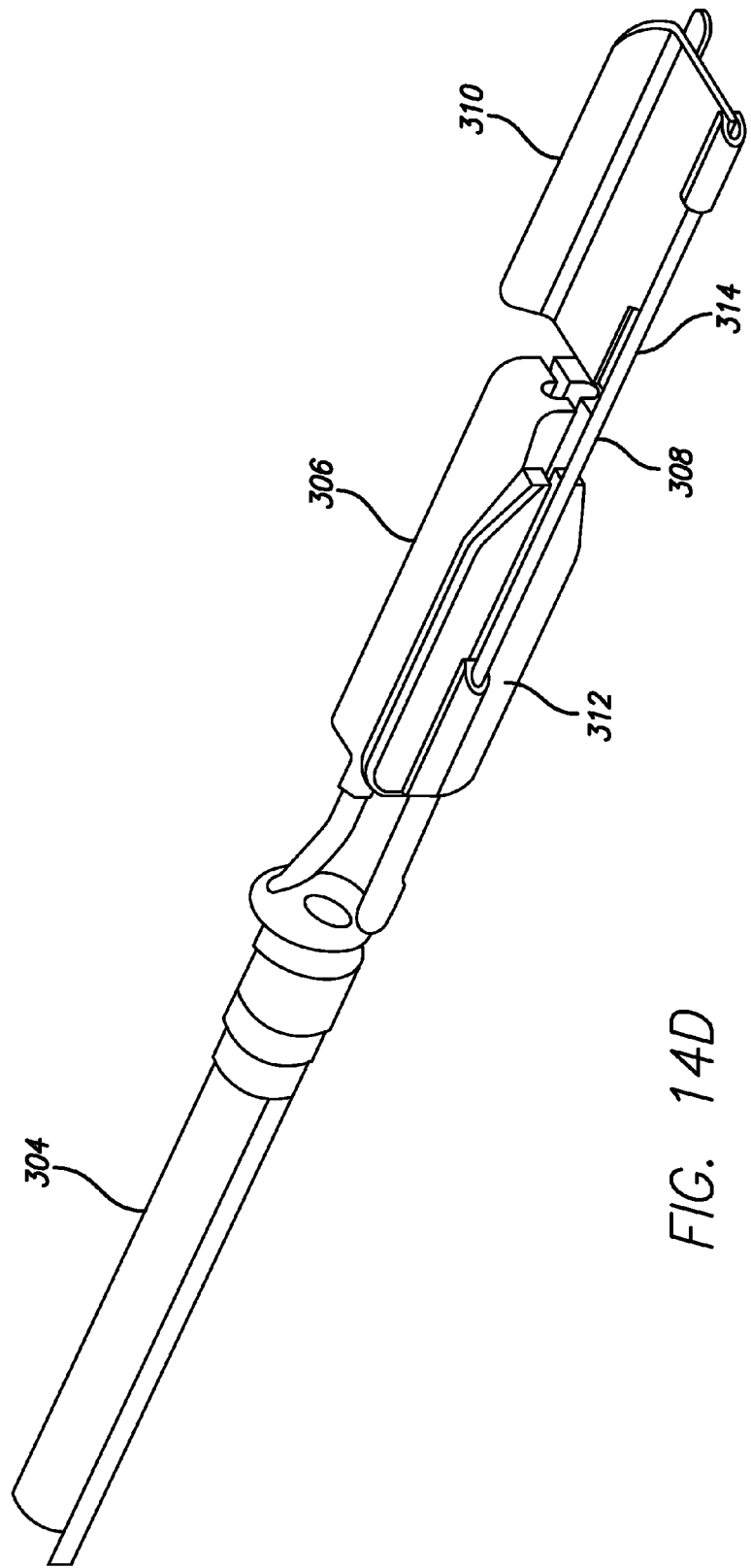
Figure 14E:
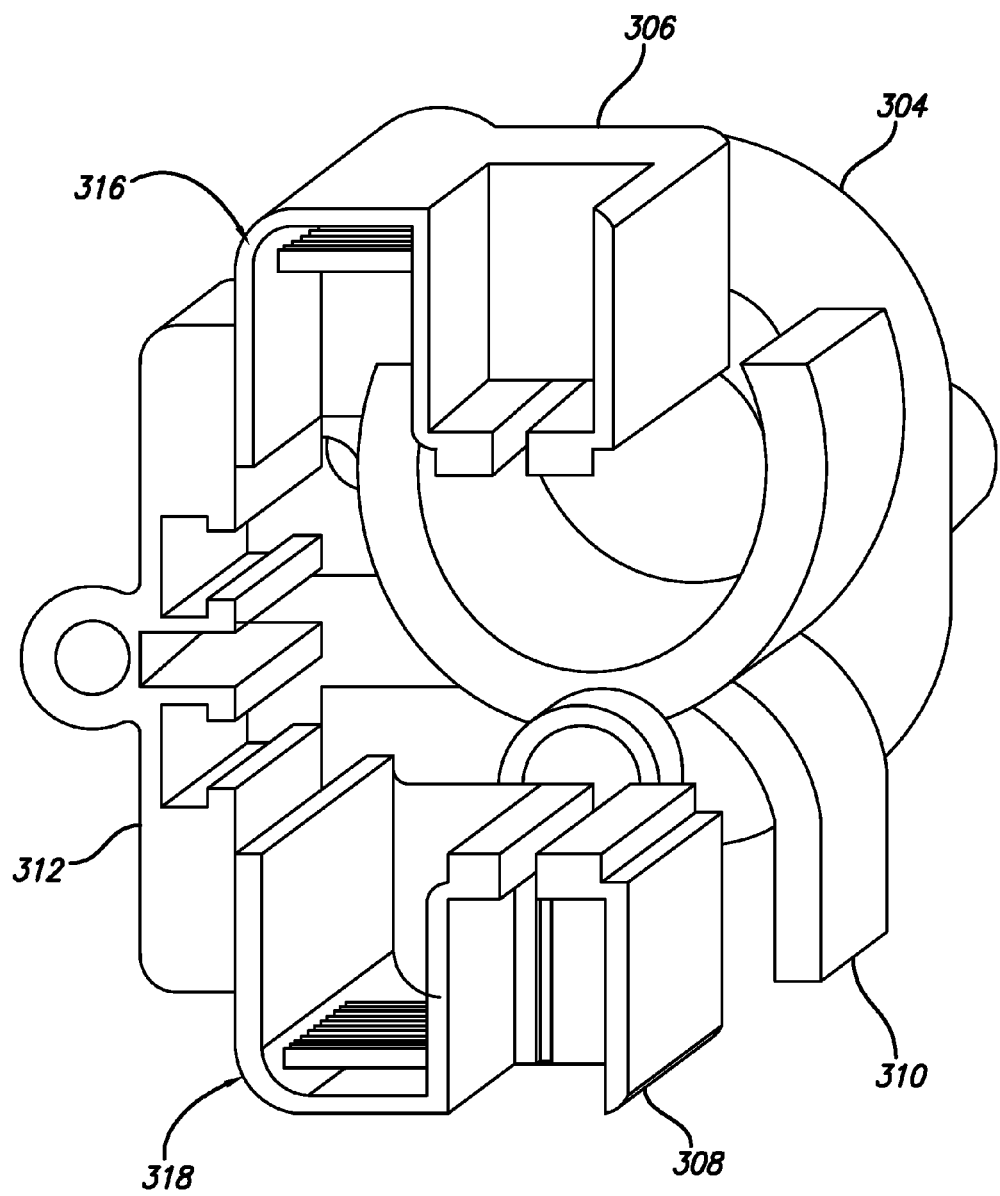
FIG. 14E shows a cross-sectional perspective view of a portion of the pod members in an open configuration with a septum still in place between the cartridge member and anvil member.

FIG. 14B shows cartridge member 306 and anvil member 308 articulated away from one another into an open configuration while maintaining a parallel orientation relative to one another. In this open configuration, tissue may be acquired and drawn into respective pod members 302 on opposite sides of septum 310. Groove plate 312, which may be comprised of various biocompatible materials, e.g., stainless steel, polycarbonate, various polymers, etc., may be held stationary relative to pod assembly 302 and may further help maintain cartridge member 306 and anvil member 308 in their parallel orientation during reconfiguration. FIG. 14C shows septum 310 removed from between cartridge member 306 and anvil member 308 by being translated distally via septum control member 314, which may be articulated from a proximal end of elongate member 304. Once the septum 310 has been removed, cartridge member 306 and anvil member 308 may be articulated to clamp onto the tissue while maintaining their parallel configuration, as shown in FIG. 14D. Once the tissue has been clamped, cartridge member 306 may be actuated to fasten the tissue. FIG. 14E shows a cross-sectional perspective view of a portion of pod members 302 in an open configuration with septum 310 still in place between cartridge member 306 and anvil member 308. As shown, cartridge member 306 and anvil member 308 along with acquisition chambers 316, 318, respectively, may be seen maintaining a parallel configuration relative to one another.

Figure 15:
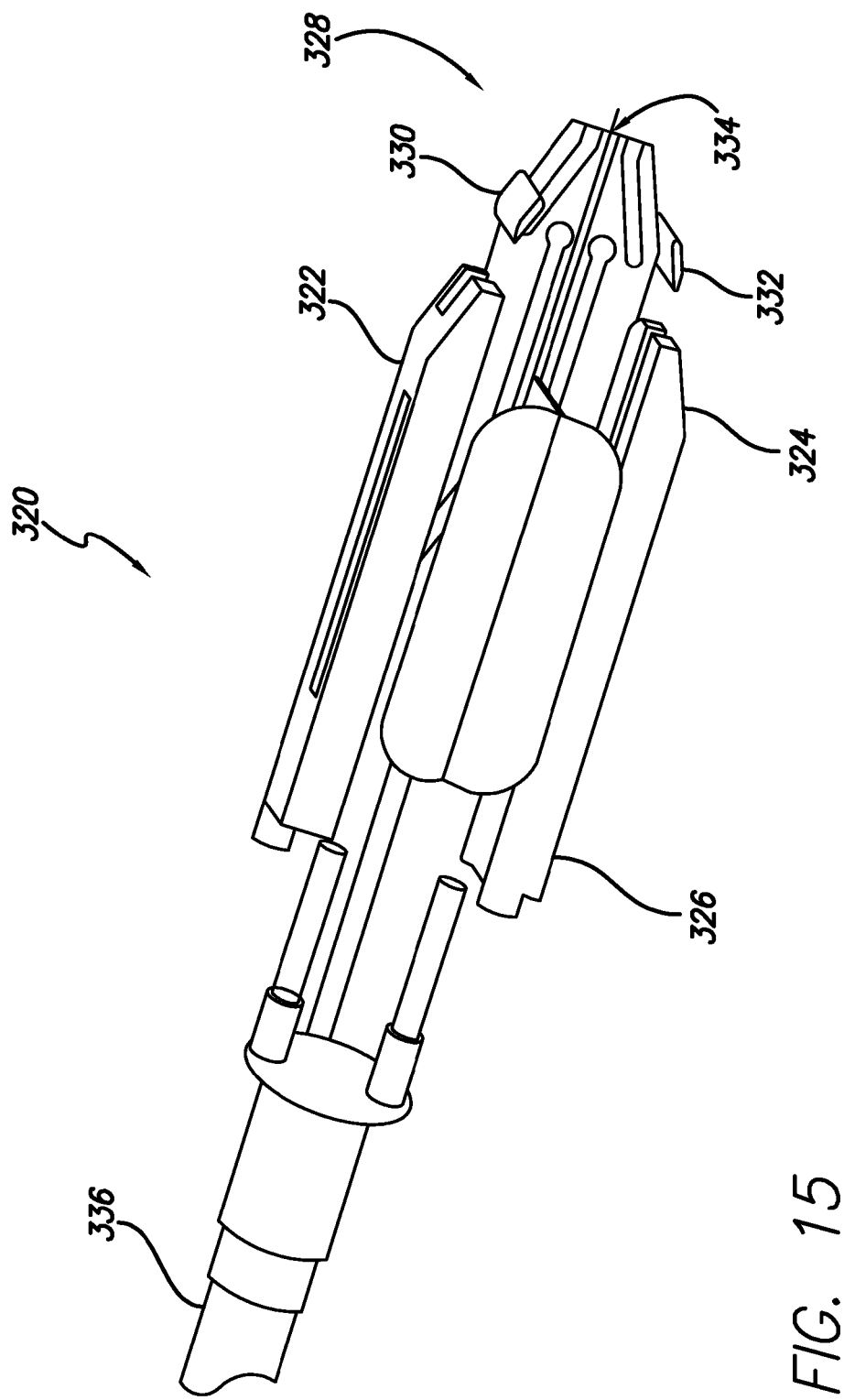
FIG. 15 shows a perspective view of yet another variation of a gastroplasty device utilizing a translational trolley plate.

FIG. 15 shows a perspective view of yet another variation of a gastroplasty device 320 positioned upon the distal end of elongate tubular member 336. Similar to the device of FIG. 14A, cartridge member 322 and anvil member 324 may be configured to open and close while maintaining a parallel configuration relative to one another. Optional septum 326 may also be positionable between members 322, 324. However, device 320 may comprise a translationally movable trolley plate 328 which may be advanced or retracted longitudinally. At least two wedging members 330, 332 may protrude from plate 328 at an angle which correspondingly abuts with the distal ends of members 322, 324 such that when plate 328 is longitudinally translated, wedging members 330, 332 may drive cartridge member 322 and anvil member 324 towards one another in a parallel configuration to clamp onto any tissue which may have been acquired by device 320. A septum groove 334 may be defined longitudinally along the plate 328 so as to enable unhindered movement relative to the septum 326. Cartridge member 322 and anvil member 324 may also be configured such that when trolley plate 328 compresses the members 322, 324 onto tissue, fasteners are automatically deployed into the tissue to fasten it.

Figure 16A:
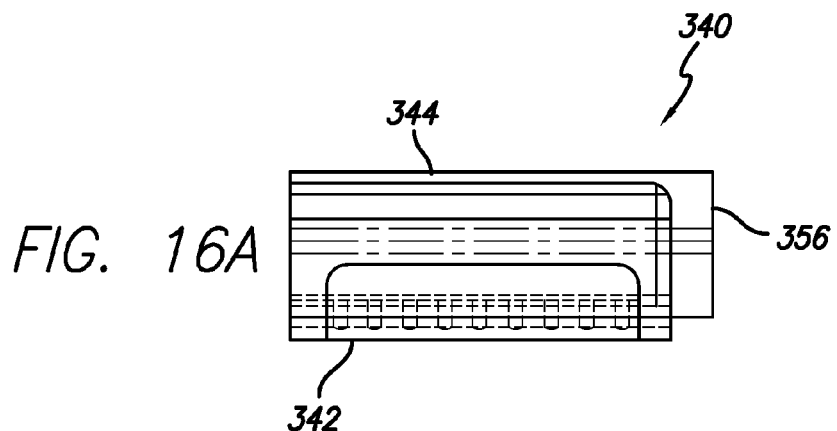
FIGS. 16A to 16D show side, end, bottom, and perspective views, respectively, of a variation of a gastroplasty device, which utilizes a static acquisition pod.
Figure 16C:
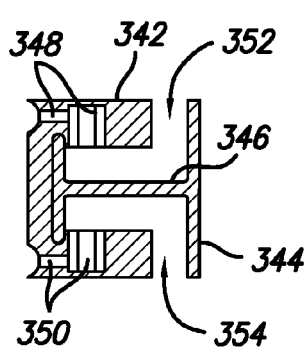
Figure 16B:
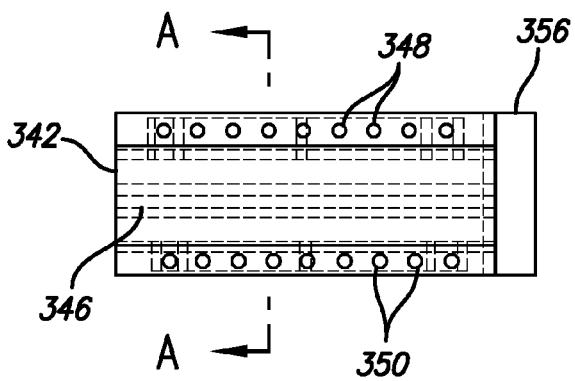

FIGS. 16A to 16C show side, end, and bottom views, respectively, of another variation of gastroplasty device 340. Generally, while other variations have enabled movement of respective pod members, this variation may maintain a static acquisition pod. Vacuum pod 342 may be comprised of a variety of biocompatible materials, e.g., polycarbonate, etc., shaped into opposing walls having vacuum plenums 348, 350 defined along the lengths of the opposing walls. While two vacuum plenums are depicted, it should be understood that any number of vacuum plenums may be employed as well.

Figure 16D:
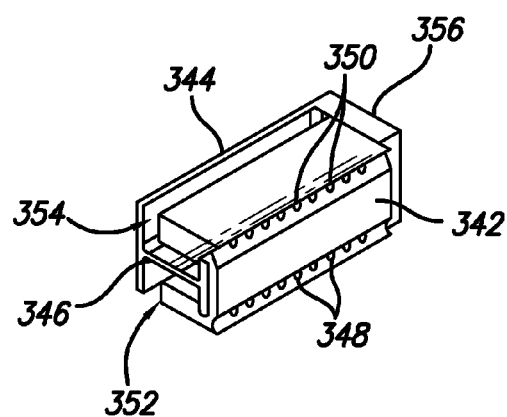
Figure 16E:
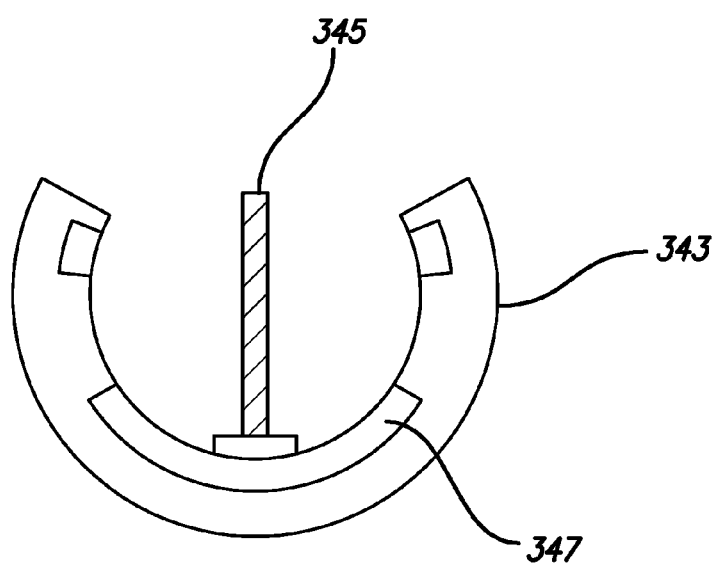
FIG. 16E shows a bottom view of one variation of a gastroplasty device having an arcuate configuration.

For example, a single vacuum plenum may be used. Similarly, three or more vacuum plenums may be used. A septum having a longitudinal member 346 and an optional perpendicularly positioned transverse member 344 may be positioned to fit within vacuum pod 342 such that at least two tissue acquisition chambers 352, 354 are formed along the length of pod 342. Alternatively, the septum may only include longitudinal member 346, and may omit any transverse members entirely, which may aid in reducing the overall profile of the distal working end of the device. The septum may generally be comprised of a similar material as vacuum pod 342 and may be further coated with a layer of a lubricious material, such as Teflon®. Furthermore, the septum may be formed of a bioabsorbable material that may either dissolve upon exposure to gastric fluids after tissue has been acquired, or may be releaseably attached to pods or chambers and fixed in place between tissue folds (e.g. left behind) once device is removed. The septum may also have end member 356 at one end of the septum which may act as a stop for the device 340. FIG. 16D shows a perspective view of acquisition device 340 revealing the vacuum plenum defined along the bottom of pod 342. While rectangular devices are depicted in FIGS. 16A-16D, it should be understood that the device 343 can have a curved or arcuate shape as well, as shown in FIG. 16E. Also depicted there are optional septum 345 and a single vacuum plenums 347.

To facilitate the acquisition of the tissue, various features may be incorporated into any of the variations described herein. For instance, one optional feature may be seen in FIG. 17, which shows a perspective view of gastroplasty device 360 having a plurality of projections or serrations 366, 368 defined along the mating surfaces of cartridge member 362 and/or anvil member 364. Serrations 366, 368 may be positioned adjacent to the cartridge and/or anvil to provide additional mechanical support of the tissue positioned between clamped members of the acquisition device 360 during tissue fixation. Alternatively clearance cuts (not shown) on the cartridge may be included to reduce the surface area and required clamping force for fixation, as well as adding traction to the system. As described above, spearing mechanisms, or sharp projections may be used as well.

Another optional feature which may be integrated with the devices herein is shown in the perspective view of gastroplasty device 370 of FIG. 18A. A single pod member 372 is shown for illustrative purposes as the feature of a rotatable shaft may be integrated into any of the devices described herein. Pod member 372 may define a opening 374 along its length for receiving tissue therein, as described above; however, the device may also comprise at least one rotatable shaft 376 positioned longitudinally within the pod member 372 adjacent to the opening 374. The rotatable shaft 376 may define one or several projections or serrations 378 along its surface such that tissue drawn into the opening 376 via a vacuum force may also be mechanically acquired by rotation of the shaft 376 in a first direction to allow serrations 378 to become affixed to the tissue. The shaft 376 may be rotated in a second opposite direction to release the acquired tissue. Moreover, the pod member 372 may acquire the tissue with the vacuum force alone, as described above, with the rotatable shaft 376 alone, or with a combination of both the vacuum force and shaft 376 operated in conjunction with one another. FIG. 18B shows a cross-section of pod member 372 having a second rotatable shaft 380 also defining projections or serrations 382 along its surface. In the case of two shafts utilized together, they may be configured to be counter-rotating such that the acquired tissue 384 is optimally retained within opening 374. Likewise, to release the acquired tissue 384, the shafts 376, 380 may be counter-rotated in the opposite direction.

Figure 19A:
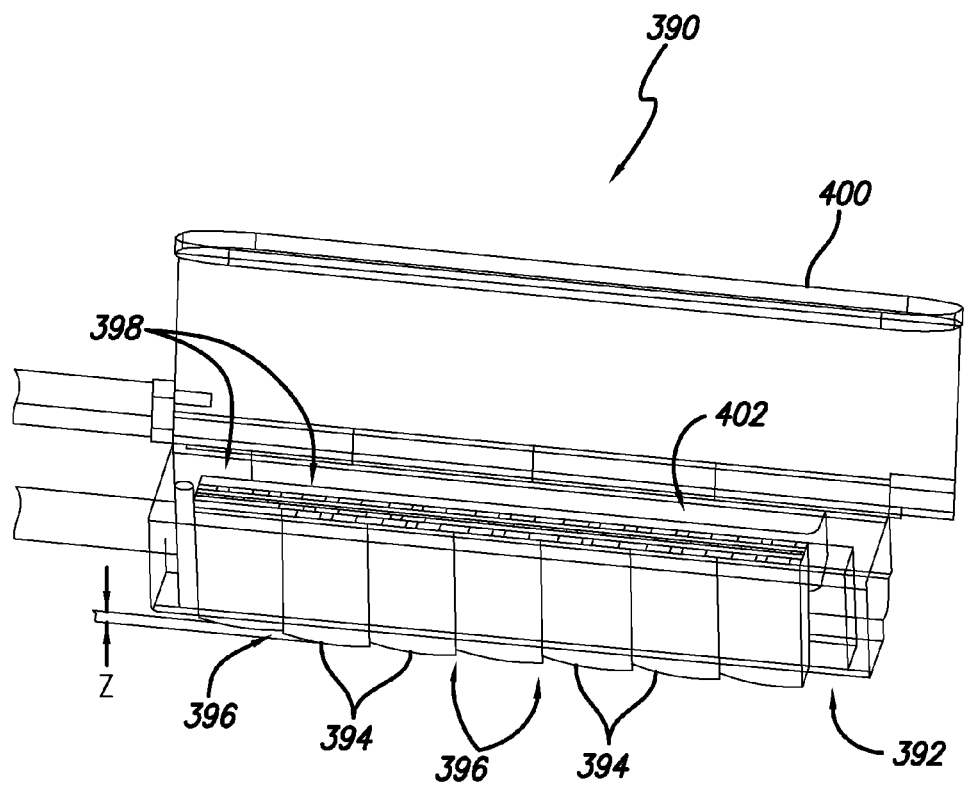
FIGS. 19A and 19B show perspective and detailed perspective views, respectively, of a device having a curved or adjustable segmented staple cartridge.

Yet another feature which may be integrated with the devices herein is shown in the perspective view of FIG. 19A, which illustrates acquisition and fixation device 390 having a single pod member for the sake of clarity. Also shown are septum 400 and opening 402. A segmented staple cartridge 392 having an adjustable curvature and height may be integrated into any number of the devices described above. Cartridge 392 may be comprised of one or more staple cartridge segments 394 which are pivotally connected to one another via joints 396 which may allow not only pivotal side-to-side motion between segments 394 but also height adjustments relative to one another.

Figure 19B:
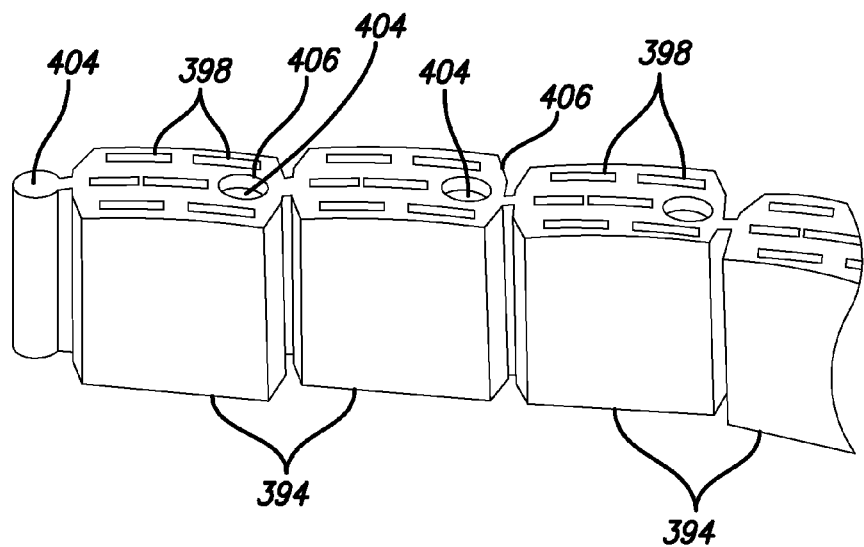

Each staple cartridge segment 394, as seen in the detail perspective view of FIG. 19B, may each define staple openings 398. In connecting with adjacent cartridge segments 394, a radiused pivot member 404 may extend from one side of the segment 394 and a receiving cavity 406 may be defined in the opposite side of the segment 394. Each pivot member 404 may extend away from segment 394 such that when positioned into a corresponding receiving cavity 406, adequate spacing exists between segments 394 such that side-to-side motion is possible between the segments 394 to define a curvature of the resulting cartridge 392. Moreover, because of the translational fit between pivot member 404 and cavity 406, the heights of different segments 394 may be varied to define a curve in the height of cartridge 392, as shown by height differential Z in FIG. 19A and the height differences between adjacent segments 394 in FIG. 19B. Accordingly, cartridge 392 may be varied in length by varying the number of segments utilized, as well as varied in curvature and in height. The corresponding anvil member may be adjusted to accordingly match the curvature of the cartridge 392.

Figure 20A:
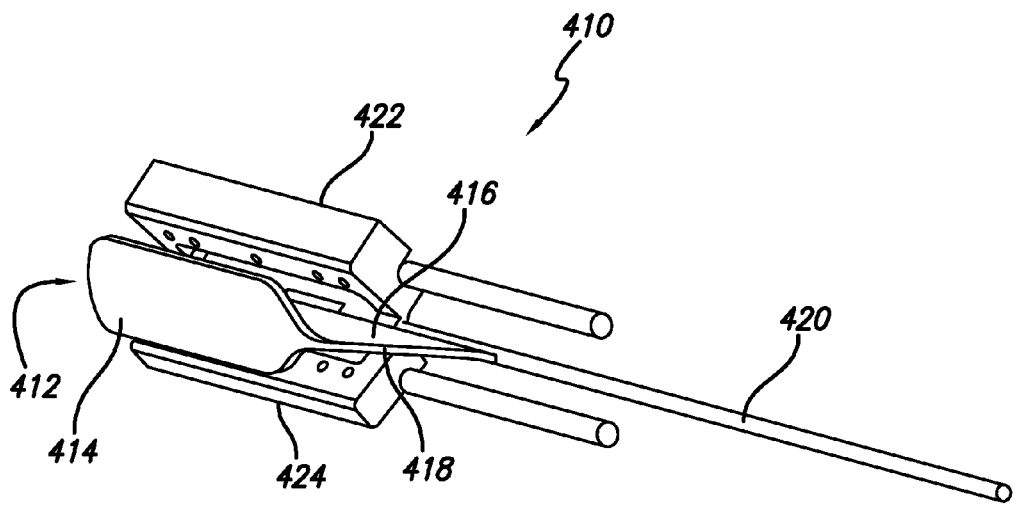
FIGS. 20A and 20B show perspective views of a septum assembly having a tapered edge for facilitating removal of the septum from the hollow body organ.
Figure 20B:
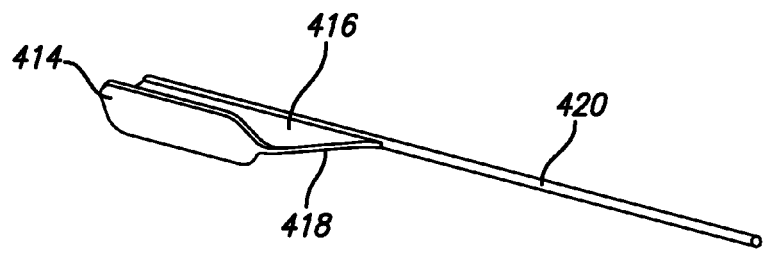

In addition to variations on types of pod members and tissue acquisition enhancements, the septum may also be adjusted in various ways to accommodate different devices and desired results. For instance, gastroplasty device 410 may be seen in the perspective view of FIG. 20A with one variation of septum assembly 412 positioned between pod members 422, 424. Septum assembly 412 may be seen in better detail in the perspective view of FIG. 20B. In this variation, the septum may have a transverse septum member 414 perpendicularly positioned relative to longitudinal septum member 416 extending from extension member 420, as described above. However, this variation may define a tapered edge 418 along the proximal edge of longitudinal septum member 416. This tapered edge 418 may extend at an acute angle from extension member 420 towards transverse septum member 414 to facilitate removal of the septum assembly 412 from within the hollow body organ.

Figure 21A:
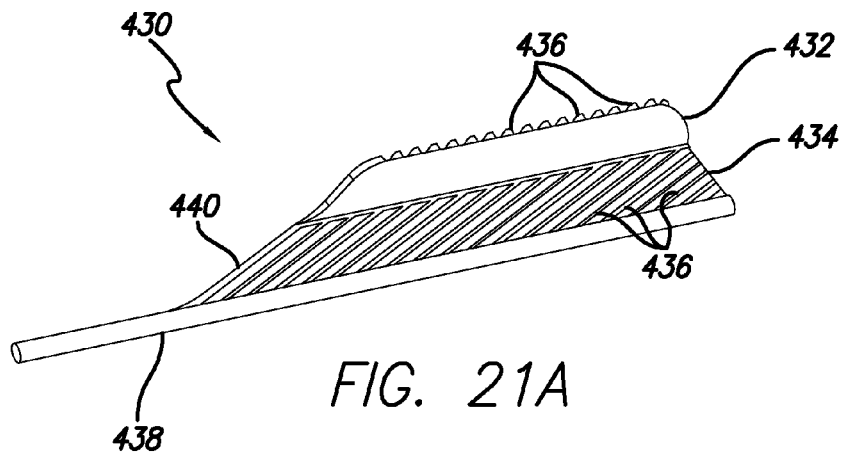
FIGS. 21A and 21B show perspective views of an alternative septum assembly having ribbed surfaces.
Figure 21B:
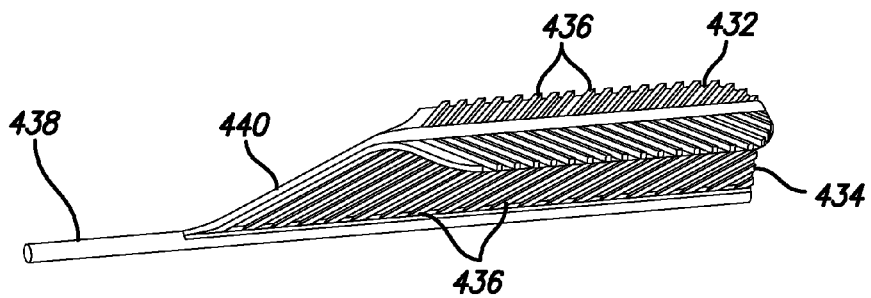
Figure 21C:
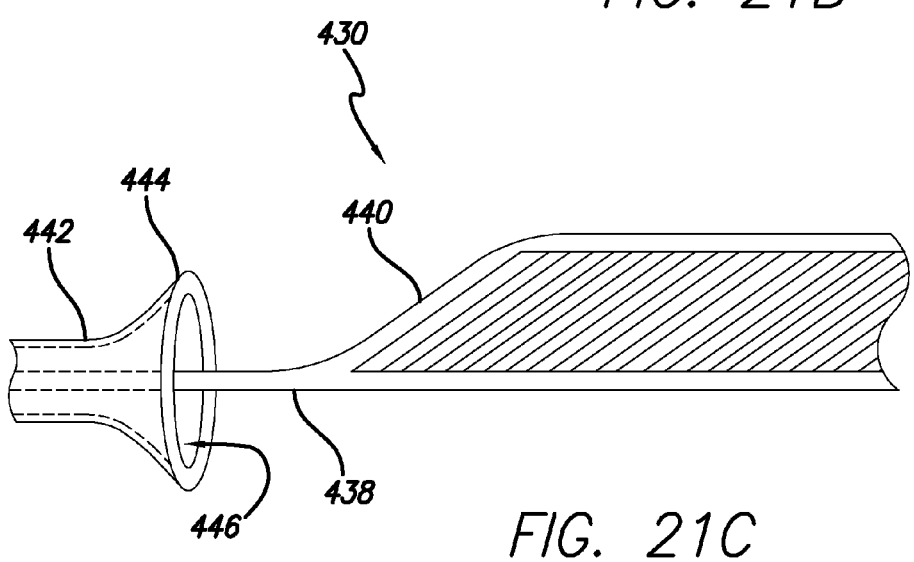
FIG. 21C shows a side view of one example of how collapse of the septum may be facilitated by withdrawing the septum into a receiving member.

Another alternative on septum variations is shown in the perspective views of FIGS. 21A and 21B. Ribbed septum assembly 430 may generally comprise transverse septum member 432, longitudinal septum member 434, tapered edge 440 extending between extension member 438 and transverse septum member 432. However, the septum members 432, 434 may be ribbed 436 to facilitate collapse of the septum assembly 430 when withdrawn from the hollow body organ. The hardness and geometry of the septum assembly 430 may be accordingly configured to provide adequate strength during vacuum-assisted tissue acquisition yet flexible enough to collapse when removed from the patient. FIG. 21C shows one example of how collapse of the septum may be facilitated by withdrawing the septum into a receiving member 442 having a tapered opening 444. As the septum assembly 430 is pulled into channel 446, the ribbed surfaces may collapse into a smaller configuration for withdrawal.

Figure 22A:
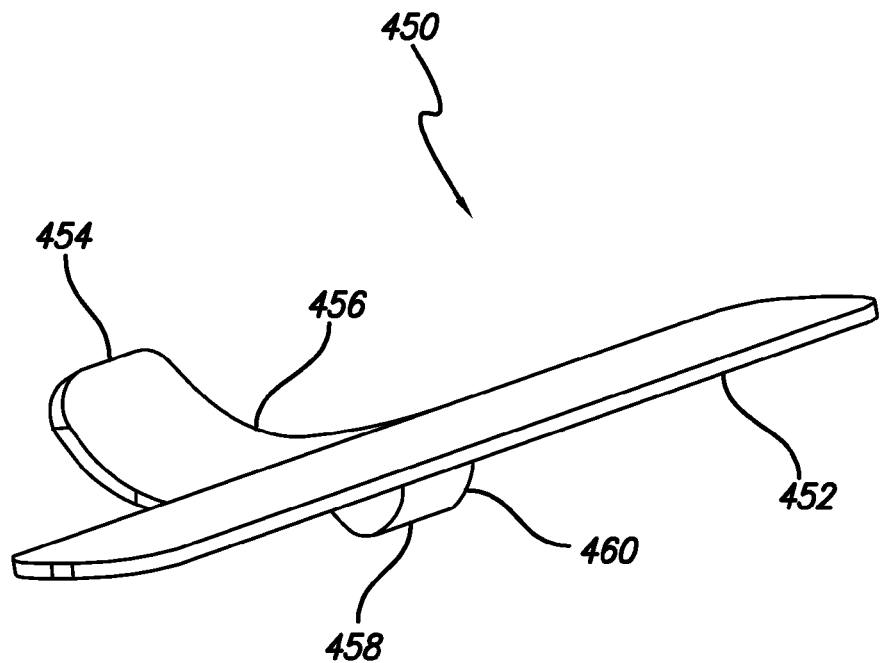
FIGS. 22A and 22B show perspective and end views, respectively, of a septum variation having at least two transverse septum members extending to opposite sides of the longitudinal septum member.
Figure 22B:
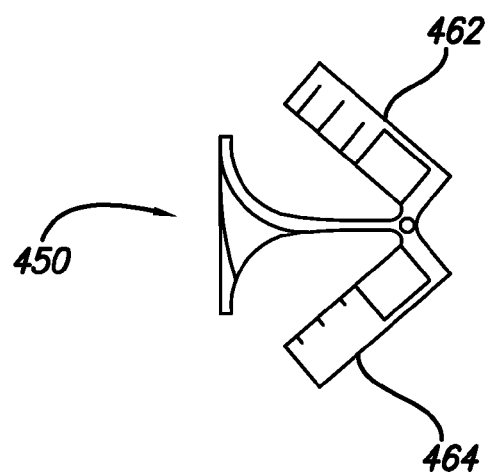

Another alternative septum variation 450 is shown in the perspective view of FIG. 22A. Longitudinal septum member 452 may have at least two transverse septum members 454, 458 extending to opposite sides of longitudinal septum 452. Each of the transverse septum members 454, 458 may define a helical tapered edge 456, 460, respectively, such that removal of the septum assembly 450 from the hollow body organ is facilitated. FIG. 22B shows an end view of the septum assembly 450 positioned between pod members 462, 464.

Figure 23A:
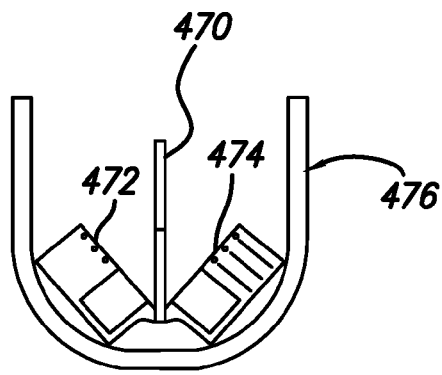
FIG. 23A illustrates an end view of an extendable septum assembly positioned between pod members and placed against stomach tissue.
Figure 23B:
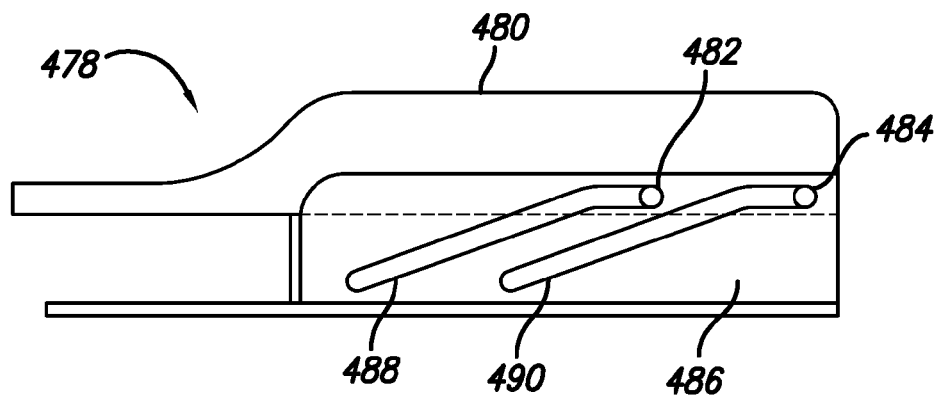
FIGS. 23B and 23C show side views of variations for extending the septum assembly from a low profile delivery to an extended deployed configuration.

Rather than using a perpendicularly-configured septum, an alternative may be to utilize a septum member having only a longitudinally extending member which extends sufficiently high so as to prevent cross-acquisition of tissue into the pod members. FIG. 23A illustrates an end view of an extendable septum assembly 470 positioned between pod members 472, 474 placed against stomach tissue 476. FIG. 23B shows a side view of one variation for extending the septum assembly 478 from a low profile delivery configuration to an extended deployed configuration. Once septum assembly 478 has been advanced into a hollow body organ in its low profile configuration, the assembly 478 may be deployed into its expanded configuration. An extension septum member 480 may have a number of projections 482, 484 protruding from either side of extension 480. A corresponding longitudinal septum base 486 may define channels 488, 490 through which projections 482, 484 located on extension 480, respectively, may be translated within. Moreover, channels 488, 490 may be angled relative to a longitudinal axis defined by septum base 486 such that distally advancing extension 480 relative to septum base 486 raises extension 480 a distance away from base 486, effectively increasing a height of the septum assembly 478. Projections 482, 484 and channels 488, 490 may be covered so that travel of the extension 480 is uninhibited by surrounding tissue.

Figure 23C:
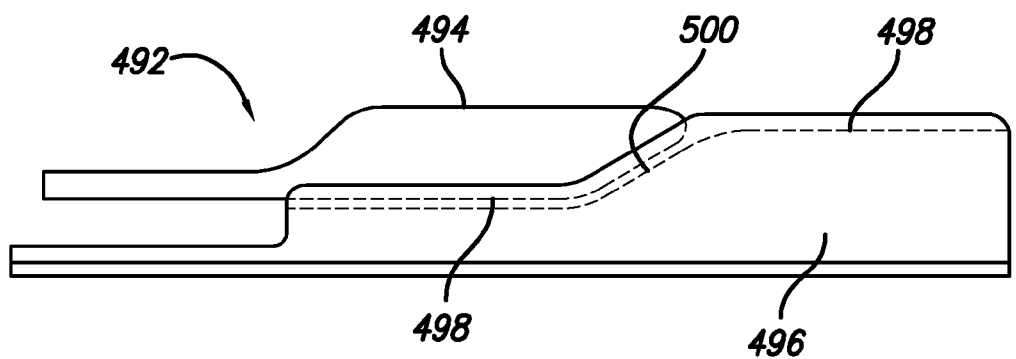

Similarly, FIG. 23C shows a side view of another septum assembly variation 492 in which extension septum member 494 is extendable from base septum member 496. When advanced distally relative to longitudinal septum base 496, extension 494 may travserse channels 498, which form ramped channel portion 500, defined within base 496 to extend into a septum assembly 492 having an increased height.

Figure 24A:
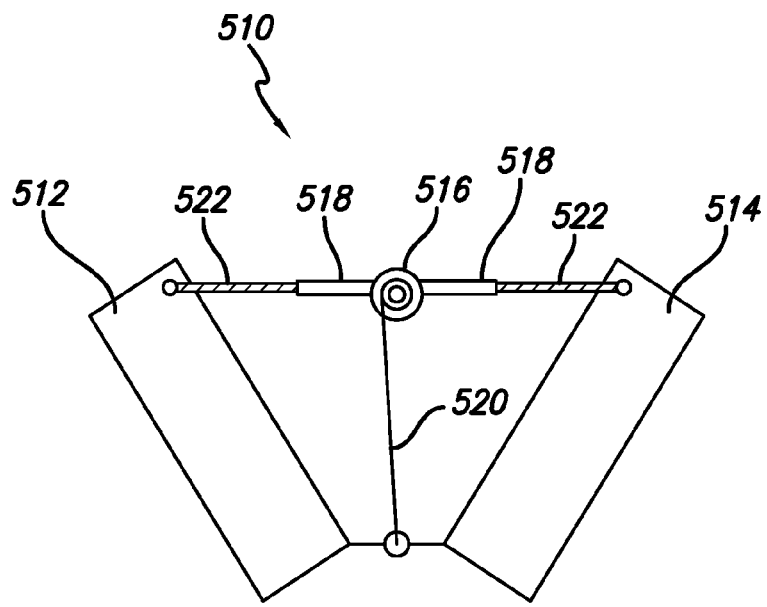
FIGS. 24A and 24B show end views of an alternative septum assembly which may be configured to deploy an extendable septum from a rolled-up configuration.
Figure 24B:
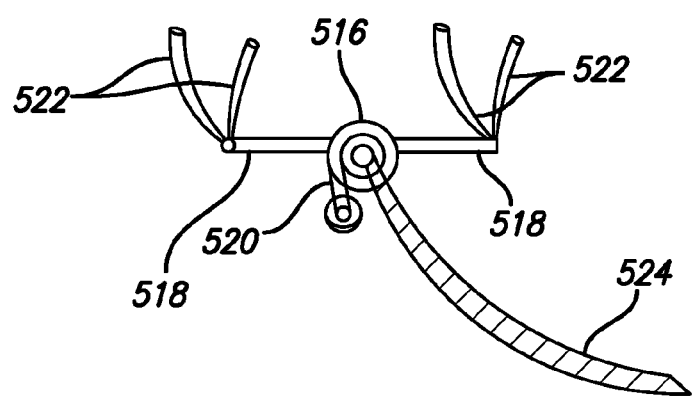

FIG. 24A shows another alternative septum assembly 510 which may be configured to deploy an extendable septum from a rolled-up configuration. As seen in the end view, septum assembly 510 is in a deployed configuration between pod members 512, 514. Retractable septum 520, may be extended from a rolled-up configuration within drum 516, which may be positioned between opposing transverse septum members 518. Cables 522 may extend from transverse septum members 518 for attachment to pod members 512, 514. After the tissue has been acquired, retractable septum 520 may be retracted into drum 516 via manipulation of control cable 524, as seen in FIG. 24B, to assume a low profile for withdrawal from the patient.

Another variation of septum assembly 530 is further shown in the perspective views of FIGS. 25A and 25B. Septum assembly 530 may comprise transverse septum member 532 and collapsible septum member 534, which may be configured between a collapsed configuration and an extended configuration. Transverse septum 532 may be elevated and lowered relative to pod members 548, 550 during delivery and deployment of septum assembly 530, e.g., via cross-members 536, 538 which may be configured into a scissors-type mechanism. Cross-members 536, 538 may have its proximal ends connected to control cable 542, which may be routed through extension member 544, while an intermediate portion of both cross-members 536, 538 may be pivotally connected to one another via pivot 540. Thus, articulation of control cable 542 from its proximal end by the surgeon or physician may actuate the scissors mechanism to either raise or lower transverse septum 532 in the directions of the arrow as shown. Transverse septum 532, when positioned between pod members 548, 550, may be secured via cables 546, as shown in FIG. 25B.

FIGS. 25C and 25D show end views of transverse septum 532 and the collapsible septum member in an expanded or extended configuration 552 and in a collapsed configuration 554. The collapsible septum member may be enclosed by a biocompatible material to prevent pinching of tissue by the cross-members 536, 538. Moreover, the material covering the collapsible septum may also be distensible, if desired. Various materials may be utilized, e.g., nylon, polymeric materials, woven materials made from various polymers, latex, elastomers, etc.

FIGS. 26A to 26C show end, bottom, and perspective views of yet another alternative septum 560. This particular septum 560 may be utilized with the device 340 of FIGS. 16A to 16D. As shown, longitudinal septum 562 may be perpendicularly and integrally connected with transverse septum member 564 at one end and base septum member 566 at an opposing end of longitudinal septum 562. Transverse septum member 564 may define radiused corners 568 at each of its four corners such that an atraumatic surface is presented to the tissue during use within a patient. Moreover, septum 560 may be extruded or formed from a singular piece of biocompatible material (any of the biocompatible materials suitable for such a structure as discussed herein may be utilized) such that a uniform structure is created.

Figure 27A:
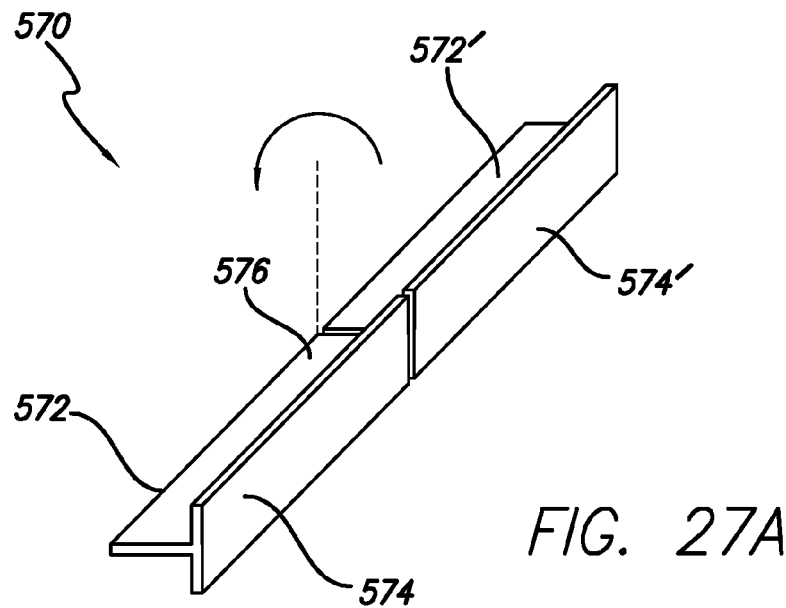
FIGS. 27A and 27B show perspective views of an alternative septum assembly having a low profile delivery configuration where the septum may be comprised of two elongate T-shaped members.
Figure 27B:
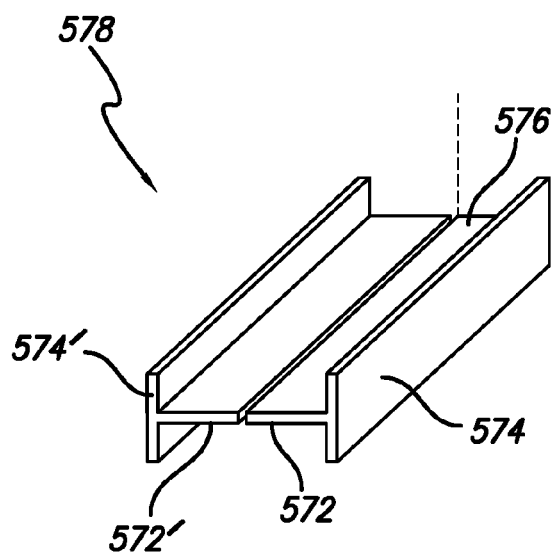

FIGS. 27A and 27B show perspective views of an alternative septum assembly 570 which may also be utilized particularly with the device 340 as discussed above. FIG. 27A shows septum 570 in a low profile delivery configuration where septum 570 may generally be comprised of two elongate T-shaped members. Each of the T-shaped members may be further comprised of longitudinal septum members 572, 572' and transverse septum members 574, 574', respectively. Each of the two elongate T-shaped members need not be uniform with one another depending upon the device into which the septum assembly 570 is placed, but each member may be pivotally connected to one another via pivot 576 at a corner of adjacent longitudinal members 572, 572'. Thus, during delivery of the device and septum 570 into the patient body, the low profile configuration of FIG. 27A may be maintained and prior to or during tissue acquisition and fixation, one of the members, e.g., septum members 572', 574' may be pivoted in the direction of the arrow such that the longitudinal portions of the septum 572, 572' contact one another to form an acquisition configuration 578 for the septum assembly, as shown in FIG. 27B. After tissue acquisition and fixation, the septum may be reconfigured into its low profile configuration for removal from the patient.

The septum in any of the above embodiments may be formed of a bioabsorbable and/or biocompatible material such as polyester (e.g., DACRON® from E. I. Du Pont de Nemours and Company, Wilmington, Del.), polypropylene, polytetrafluoroethylene (PTFE), expanded PTFE (ePTFE), polyether ether ketone (PEEK), nylon, extruded collagen, silicone, polylactic acid (PLA), poly(lactic-co-glycolic acid) (PLGA), or polyglycolic acid (PGA). Furthermore, it may be flexible, biocompatible material which can either be left behind within the partition or expelled distally, and either absorbed within the stomach, or digested and expelled through the patient's gastrointestinal tract.

Figure 28A:
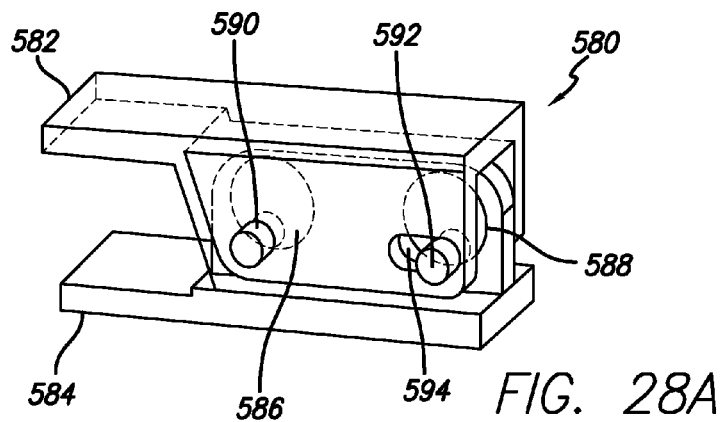
FIGS. 28A to 28C show perspective views of an example of a clamping mechanism having two cam members.
Figure 28B:
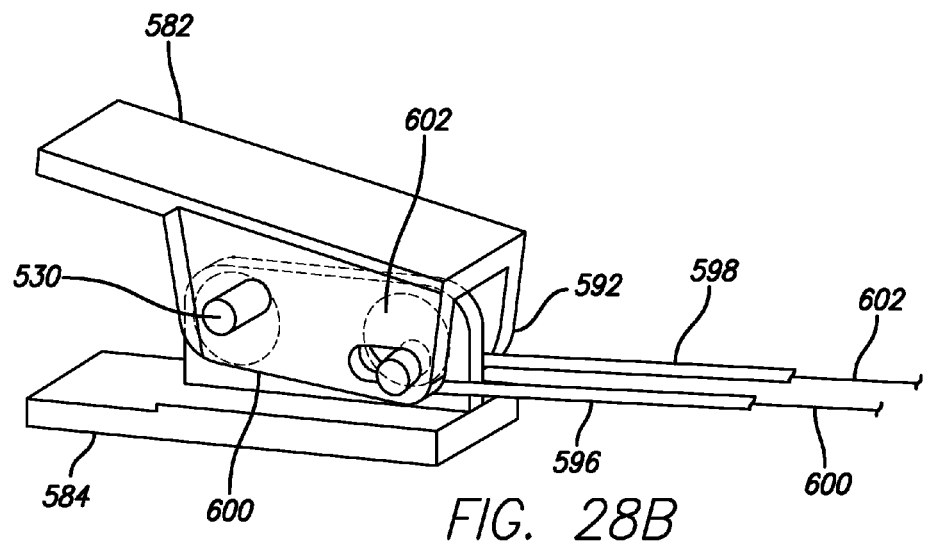
Figure 28C:
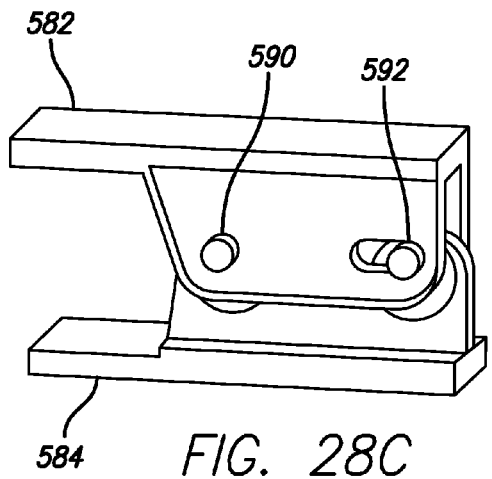

As discussed above, once the gastroplasty device has acquired the appropriate tissue, the device may be clamped upon the tissue to be fastened. Clamping multiple layers of tissue to one another may require a clamping mechanism which is configured to deliver a high degree of clamping pressure. One example of such a clamping mechanism 580 is shown in the perspective views of FIGS. 28A to 28C, which show one variation for opening the clamp. Clamping mechanim 580 may have attachment members 582, 584 for secure connection to each of a pod member. Each of the attachment members 582, 584 may be connected to one another via rotatable cams 586, 588, where each cam may have a rotatable pivot, 590, 592, respectively, protruding therefrom. FIG. 28A shows clamping mechanism 580 in a closed and clamped configuration while FIG. 28B shows the mechanism 580 being initially opened. To open (or close) the mechanism 580, cam 586 may be rotated by actuating a control cable 600, which may be routed, for instance, through a tubular member 596 positioned within the elongate member 12, from its proximal end. Cam 588 may then be rotated by actuating control cable 602, which may be routed within tubular member 598 also through tubular member 596. Because attachment members 582, 584 rotate about pivot 590, a channel 594 may be defined in member 582 within which pivot 592 may translate when cam 588 is rotated to effectuate clamping or opening of the pod members.

Figure 29A:
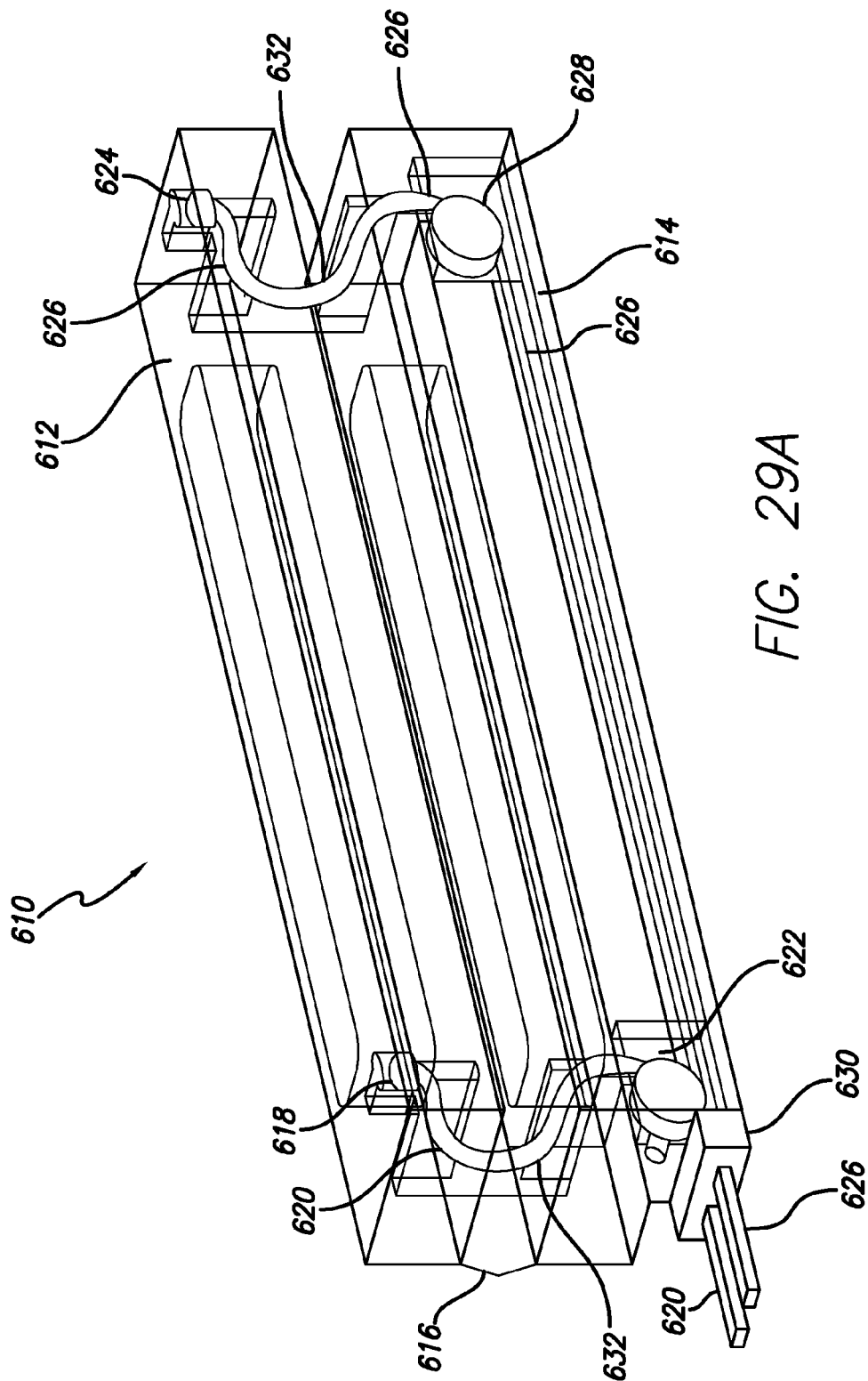
FIG. 29A shows a perspective view of one example of how clamping cables may be routed through a gastroplasty device described herein.

In addition to a cam mechanism 580, clamping cables may also be utilized, as discussed above. FIG. 29A shows a perspective view of one example of how clamping cables may be routed through an acquisition and fixation device 610. As seen, device 610 having pod members 612, 614 may be pivotable about longitudinal pivot 616. Although a pivoting device is shown in this variation, the routing of cables may be utilized in any of the other acquisition and fixation devices utilizing pivoting motion as well as parallel clamping. A first clamping cable 620 may be routed into one of the pod members, e.g., pod member 614, through positioning member 630 mounted on pod member 614 and routed over pulley or radiused member 622, also contained within pod member 614. First cable 620 may be looped 632 adjacent to pivot 616 to allow for placement of the septum (not shown for clarity) and then anchored to clamping cable anchor 618. Likewise, second clamping cable 626 may be routed through positioning member 630 adjacent to first clamping cable 620 and through pod member 614 and over pulley or radiused member 628, also contained within pod member 614. Second cable 626 may also be looped 632 adjacent to pivot 616 to allow for placement of the septum and then anchored to clamping cable anchor 624.

Figure 29B:
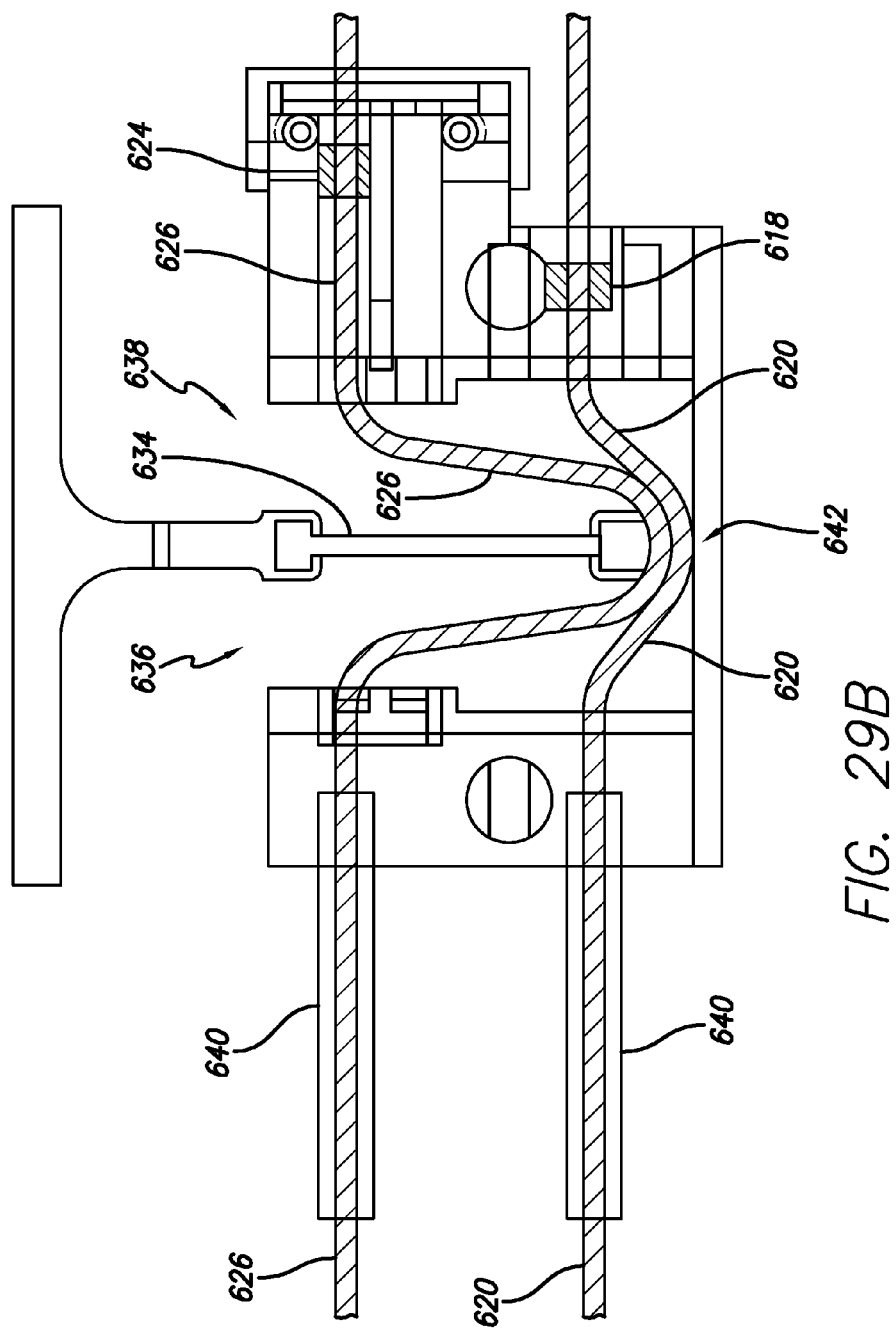
FIG. 29B shows a cross-sectioned end view of a parallel clamping device with the septum shown.

FIG. 29B shows a cross-sectioned end view of a parallel clamping device with the septum 634 shown. Like features are similarly numbered as corresponding features from FIG. 29A. As in the pivoting variation, first 620 and second 626 clamping cables may be routed through corresponding tubular members 640 and the cables may be looped through one or more slots 642 defined in septum 634 and subsequently routed into the opposing pod member for anchoring. Clamping cables 620, 626 are preferably routed to facilitate the unhindered translation of septum 634 as well as to ensure unobstructed access to openings 636, 638 for the tissue to be acquired and fastened.

In yet another clamping variation, FIGS. 30A and 30B show side and edge views of an alternative gastroplasty device 650 utilizing linked pod members. Cartridge member 652 and anvil member 654 may be connected to one another via linking arms 656, 658 pivotally attached to one another via pivot 660 at one end of the device 650 and via linking arms 662, 664 also pivotally attached to one another via pivot 666 at the opposite end of the device 650. Clamping cables 672 may be routed through tubular member 670 into the device 650 and over pulleys 674, 676, as described above, for moving anvil member 654 between an open and closed configuration when acquiring tissue within acquisition region 668. Firing cable 678 may be manipulated to deploy the fasteners from within cartridge member 652 when anvil member 654 is clamped over the acquired tissue. Deployment of the fasteners from cartridge member 652 may be achieved by incorporation of the firing wedge and other mechanisms as taught in U.S. Pat. No. 4,610,383, which is hereby incorporated by reference in its entirety. In addition, clamping may be accomplished via hydraulic, pneumatic, or electropneumatic mechanisms, as discussed above.

In describing the system and its components, certain terms have been used for understanding, brevity, and clarity. They are primarily used for descriptive purposes and are intended to be used broadly and construed in the same manner. Having now described the invention and its method of use, it should be appreciated that reasonable mechanical and operational equivalents would be apparent to those skilled in this art. Those variations are considered to be within the equivalence of the claims appended to the specification.

What is claimed is:

1. A gastroplasty device, comprising:
a cartridge assembly having a longitudinal axis, the cartridge assembly having a first tissue acquisition member pivotable about the longitudinal axis in relation to a second tissue acquisition member, the first tissue acquisition member including a first mating surface that faces a second mating surface of the second tissue acquisition member when the cartridge assembly is in a closed configuration, each tissue acquisition member including a tissue receiving cavity including an opening disposed in the respective first and second mating surfaces, the tissue receiving cavity being coupled to a vacuum source located opposite said opening to draw a first tissue fold into the first acquisition member cavity and a second tissue fold into the second acquisition member cavity; and
a stapler disposed on the first tissue acquisition member and the second tissue acquisition member for stapling the first tissue fold and the second tissue fold together; and
a septum removably positioned between the first tissue acquisition member and the second tissue acquisition member and between the first tissue fold and the second tissue fold.

2. The gastroplasty device of claim 1, wherein the vacuum source of the first tissue acquisition member is actuatable separately from the vacuum source of the second tissue acquisition member.

3. The gastroplasty device of claim 1, wherein the cartridge assembly includes an expandable element selected from the group consisting of a scope, a balloon, and a wire form.

4. The gastroplasty device of claim 1, wherein the septum comprises a bioabsorbable material.

5. The gastroplasty device of claim 4, wherein the bioabsorbable material is selected from the group consisting of polylactic acid (PLA), poly(lactic-co-glycolic acid) (PLGA), and polyglycolic acid (PGA).

6. The gastroplasty device of claim 1, wherein, when the cartridge assembly is in the closed configuration, the first and second mating surfaces face the longitudinal axis of the cartridge assembly.

7. The gastroplasty device of claim 1, wherein the first mating surface is configured to mate with the first tissue fold and the second mating surface is configured to mate with the second tissue fold.

8. The gastroplasty device of claim 1, wherein the septum includes a longitudinal barrier and first and second transverse barrier portions.

9. The gastroplasty device of claim 8, wherein the first and second transverse barrier portions have an arcuate shape and extend from the longitudinal barrier.

* * * * *